US010974235B2

(12) United States Patent
Groves et al.

(10) Patent No.: US 10,974,235 B2
(45) Date of Patent: *Apr. 13, 2021

(54) TARGETED, METAL-CATALYZED FLUORINATION OF COMPLEX COMPOUNDS WITH FLUORIDE ION VIA DECARBOXYLATION

(71) Applicant: The Trustees of Princeton University, Princeton, NJ (US)

(72) Inventors: John T. Groves, Princeton, NJ (US); Xiongyi Huang, Plainsboro, NJ (US)

(73) Assignee: TRUSTEES OF PRINCETON UNIVERSITY, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/702,014

(22) Filed: Dec. 3, 2019

(65) Prior Publication Data
US 2020/0108380 A1  Apr. 9, 2020

Related U.S. Application Data

(60) Division of application No. 15/019,673, filed on Feb. 9, 2016, now Pat. No. 10,543,481, which is a continuation-in-part of application No. 14/239,719, filed as application No. PCT/US2012/051628 on Aug. 20, 2012, now abandoned.

(60) Provisional application No. 62/113,847, filed on Feb. 9, 2015, provisional application No. 61/525,301, filed on Aug. 19, 2011, provisional application No. 61/639,523, filed on Apr. 27, 2012, provisional application No. 61/679,367, filed on Aug. 3, 2012.

(51) Int. Cl.
| | |
|---|---|
| C07B 59/00 | (2006.01) |
| C07D 213/643 | (2006.01) |
| B01J 31/18 | (2006.01) |
| A61K 51/04 | (2006.01) |
| C07C 41/22 | (2006.01) |
| C07D 319/20 | (2006.01) |
| C07C 49/80 | (2006.01) |
| C07D 209/48 | (2006.01) |
| C07C 69/65 | (2006.01) |
| B01J 31/22 | (2006.01) |
| C07C 67/287 | (2006.01) |
| B01J 31/02 | (2006.01) |
| B01J 31/04 | (2006.01) |
| C07J 1/00 | (2006.01) |
| C07B 39/00 | (2006.01) |
| C07C 17/363 | (2006.01) |
| C07C 45/67 | (2006.01) |
| C07C 49/813 | (2006.01) |
| C07C 43/225 | (2006.01) |

(52) U.S. Cl.
CPC .......... *B01J 31/183* (2013.01); *A61K 51/0423* (2013.01); *A61K 51/0446* (2013.01); *A61K 51/0455* (2013.01); *A61K 51/0493* (2013.01); *B01J 31/0231* (2013.01); *B01J 31/0239* (2013.01); *B01J 31/04* (2013.01); *B01J 31/2243* (2013.01); *C07B 39/00* (2013.01); *C07B 59/00* (2013.01); *C07C 17/363* (2013.01); *C07C 41/22* (2013.01); *C07C 43/225* (2013.01); *C07C 45/676* (2013.01); *C07C 49/80* (2013.01); *C07C 49/813* (2013.01); *C07C 67/287* (2013.01); *C07C 69/65* (2013.01); *C07D 209/48* (2013.01); *C07D 213/643* (2013.01); *C07D 319/20* (2013.01); *C07J 1/0059* (2013.01); *B01J 31/0209* (2013.01); *B01J 2231/40* (2013.01); *B01J 2231/70* (2013.01); *B01J 2531/025* (2013.01); *B01J 2531/0252* (2013.01); *B01J 2531/72* (2013.01); *C07B 2200/05* (2013.01); *C07C 2601/08* (2017.05); *C07C 2603/74* (2017.05)

(58) Field of Classification Search
CPC ...... B01J 31/04; B01J 31/183; B01J 31/0059; A61K 51/04; C07B 59/00; C07D 209/48; C07D 213/643; C07C 41/22
See application file for complete search history.

(56) References Cited

U.S. PATENT DOCUMENTS

| | | |
|---|---|---|
| 3,812,116 A | 5/1974 | Takano et al. |
| 4,046,553 A | 9/1977 | Takahashi et al. |
| 4,133,675 A | 1/1979 | Schurter |
| 4,233,054 A | 11/1980 | Szczepanski et al. |
| 4,233,055 A | 11/1980 | Martin |
| 4,233,056 A | 11/1980 | Maier |

(Continued)

FOREIGN PATENT DOCUMENTS

| | | |
|---|---|---|
| JP | 51-139627 | 2/1976 |
| JP | 51-142536 | 8/1976 |
| JP | 51-142537 | 8/1976 |

OTHER PUBLICATIONS

Karimipour et al. Oxidative Decarboxylation of Carboxylic Acids with Tetrabutylammonium Periodate Datalyzed by Manganese (III) Meso-Tetraarylporphyrins: Effect of Metals, Meso-substitutents, and Anionic Axial Ligands, Chin. J. Catal, vol. 28(11), 940-946. (Year: 2007).*

(Continued)

*Primary Examiner* — Michael G. Hartley
*Assistant Examiner* — Jagadishwar R Samala
(74) *Attorney, Agent, or Firm* — Volpe Koenig

(57) ABSTRACT

Methods of preparing fluorinated compounds by carboxylative fluorination using fluoride are contained herein. Fluorinated compounds are provided. Methods of using fluorinated compounds are contained herein.

8 Claims, 35 Drawing Sheets

(56) References Cited

U.S. PATENT DOCUMENTS

| | | | |
|---|---|---|---|
| 4,233,306 | A | 11/1980 | Boger et al. |
| 4,233,308 | A | 11/1980 | Kunz et al. |
| 4,244,962 | A | 1/1981 | Hubele et al. |
| 4,253,866 | A | 3/1981 | Schurter |
| 4,704,484 | A | 11/1987 | White |
| 6,723,874 | B1 | 4/2004 | Braun et al. |

OTHER PUBLICATIONS

Takamatsu etal. Improved synthesis of 9-(2,3-dideoxy-2-fluoro-D-threo-pentofuranosyl)adenine (FddA) using triethylamine trihydrofluoride, Tetrandron Letters, 42, 2321-2324. (Year: 2001).*
Adler et al., "Mechanistic Investigations of Porphyrin Syntheses. I. Preliminary Studies on ms-Tetraphenylporphin"; J. Am. Chem. Soc., (1964) vol. 86, pp. 3145-3149.
Adler et al., "On the preparation of metalloporphyrins"; J. of Inorg. & Nucl. Chem., (1970) vol. 32, pp. 2443-2445.
Althaus et al., "Asymmetric oxidative α-fluorination of 2-alkylphenylacetaldehydes with AgHF2 and ruthenium/PNNP catalysts"; Journal of Fluorine Chemistry, (2009) 130, pp. 702-707.
Althaus et al., "Ruthenium-Catalyzed Asymmetric Electrophilic Fluorination of 1,3-Dicarbonyl Compounds"; Organometallics, (2007) 26, pp. 5902-5911.
Ametamey et al., "Molecular Imaging with PET"; Chem. Rev., (2008) 108, pp. 1501-1516.
Casitas et al., "Nucleophilic Aryl Fluorination and Aryl Halide Exchange Mediated by a CuI /CuIII Catalytic Cycle"; J. Am. Chem. Soc. (2011) 133, 19386-19392.
Beeson and MacMillan, "Enantioselective Organocatalytic α-Fluorination of Aldehydes"; J. Am. Chem. Soc., (2005) 127, pp. 8826-8828.
Zhang et al., "Copper-Catalyzed Regioselective Fluorination of Allylic Halides"; Angew. Chem. Int. Ed. (2013) 52, pp. 7549-7553.
Bloom et al., "A Polycomponent Metal-Catalyzed Aliphatic, Allylic, and Benzylic Fluorination"; Angew. Chem. Int. Ed., (2012) 51, pp. 10580-10583.
Bloom et al., "A photocatalyzed aliphatic fluorination"; Chem. Sci., (2014) 5, pp. 1175-1178.
Bobbio and Gouvemeur, "Catalytic asymmetric fluorinations"; Org. Biomol. Chem., (2006) 4, pp. 2065-2075.
Braun and Doyle, "Palladium-Catalyzed Allylic C—H Fluorination"; J. Am. Chem. Soc., (2013) 135, pp. 12990-12993.
Brooks et al., "Late-stage [18F] fluorination: new solutions to old problems"; Chem. Sci., (2014) 5, pp. 4545-4553.
Bruns and Haufe, "Enantioselective introduction of fluoride into organic compounds First asymmetric ring opening of epoxides by Hydrofluorinating reagents"; Journal of Fluorine Chemistry, (2000) 104, pp. 247-254.
Campbell and Ritter, "Late-Stage Formation of Carbon—Fluorine Bonds"; Chem. Rec., (2014) 14, pp. 482-491.
Campbell and Ritter, "Late-Stage Fluorination: From Fundamentals to Application"; Org. Process Res. Dev., (2014) 18, pp. 474-480.
Che et al., "Selective functionalisation of saturated C—H bonds with metalloporphyrin catalysts"; Chem. Soc. Rev., (2011)40, pp. 1950-1975.
Dang et al., "Mild Copper-Catalyzed Fluorination of Alkyl Inflates with Potassium Fluoride"; Angew. Chem. Int. Ed., (2014) 53, pp. 6473-6476.
Daniels et al., "Potent enzyme-activated irreversible inhibitors for α-Chymotrypsin"; J. Biol. Chem., (1983) 258, pp. 5046-5053.
Emsley, "Very Strong Hydrogen Bonding"; Prog. Inorg. Chem., (1968) 9, 161.
Essersi et al., "Diastereoselective Synthesis of γ-Phthalimido-β-Hydroxy Esters and N-Protected 4-Amino-1,3-Diols Starting from Natural α-Amino Acids"; Lett. Org. Chem., (2010) 7, 69-72.
Fier and Hartwig, "Copper Mediated Fluorination of Aryl Iodides"; J. Am. Chem. Soc., (2012) 134: (26), pp. 10795-10798.

Fier and Hartwig, "Selective C—H Fluorination of Pyridines and Diazines Inspired by a Classic Amination Reaction"; Science, (2013) vol. 342, pp. 956-960.
Fier et al., "Copper-Mediated Fluorination of Arylboronate Esters. Identification of a Copper(III) Fluoride Complex"; J. Am. Chem. Soc., (2013) 135, pp. 2552-2559.
Zalatan and Du Bois, "Understanding the Differential Performance of Rh2(esp)2 as a Catalyst for C—H Amination"; J. Am. Chem.Soc. (2009) 131, pp. 7558-7559.
Frisch et al., Google Scholar Citations, J. A. Pople, Gaussian 09 (Revision C.01), Gaussian Inc., Wallingford, CT, 2010.
Furuya et al., "Catalysis for fluorination and trifluoromethylation"; Nature (2011) 473, pp. 470-477.
Gorske et al., "Regio- and Stereoselective Synthesis of Fluoroalkenes by Directed Au(I) Catalysis"; Org. Lett. (2009) 11, pp. 4318-4321.
Graham et al., Enantioselective Radiosynthesis of Positron Emission Tomography (PET) Tracers Containing [18F] Fluorohydrins; J. Am. Chem. Soc. (2014) 136, pp. 5291-5294.
Grakauskas, "Aqueous Fluorination of Carboxylic Acid Salts"; J. Org. Chem. (1969) 34, pp. 2446-2450.
Groves and Stern, "Olefin Epoxidation by Manganese(IV) Porphyrins: Evidence for Two Reaction Pathways"; J. Am. Chem. Soc. (1987) 109, pp. 3812-3814.
Groves et al., "Hydrocarbon Oxidations with Oxometalloporphinates. Isolation and Reactions of a (Porphinato) manganese(V) Complex"; J. Am. Chem. Soc. (1980) 102, pp. 6375-6377.
Groves, "Reactivity and mechanisms of metalloporphyrincatalyzed oxidations"; J. Porphyrins Phthalocyanines (2000) 4, pp. 350-352.
Halperin et al., "A Convenient Photocatalytic Fluorination of Unactivated C—H Bonds"; Angew. Chem. Int. Ed. (2014) 53, pp. 4690-4693.
Hamashima and Sodeoka, "Enantioselective Fluorination Reactions Catalyzed by Chiral Palladium Complexes"; Synlett (2006) pp. 1467-1478.
Hamashima et al., "An Efficient Enantioselective Fluorination of Various β-Ketoesters Catalyzed by Chiral Palladium Complexes"; J. Am. Chem. Soc. (2002) 124, pp. 14530-14531.
Yin et al., "Silver-Catalyzed Decarboxylative Fluorination of Aliphatic Carboxylic Acids in Aqueous Solution"; J. Am. Chem. Soc. (2012) 134, pp. 10401-10404.
Hintermann and Togni, "Catalytic Enantioselective Fluoration of β-Ketoesters"; Angew. Chem. Int. Ed. (2000) vol. 39 No. 23, pp. 4359.
Hollingworth et al., :Palladium-Catalyzed Allylic Fluorination; Angew. Chem. Int. Ed. (2011) 50, pp. 2613-2617.
Hollingworth et al., "Transition metal catalysis and nucleophilic fluorination"; Chem. Commun. (2012) 48, pp. 2929-2942.
Ye et al., "Cu(OTf)2-Mediated Fluorination of Aryltrifluoroborates with Potassium Fluoride"; J. Am. Chem. Soc. (2013) 135, pp. 16292-16295.
Huang et al., "Late Stage Benzylic C—H Fluorination with [18F]Fluoride for PET Imaging"; J. Am. Chem. Soc. (2014) 136, pp. 6842-6845.
Huiban et al., "A broadly applicable [18F]trifluoromethylation of aryl and heteroaryl iodides for PET imaging"; Nat. Chem. (2013) 5, pp. 941-944.
Hull et al., "Palladium-Catalyzed Fluorination of Carbon—Hydrogen Bonds"; J. Am. Chem. Soc. (2006) 128, pp. 1134-7135.
Ichiishi et al., "Copper-Catalyzed [18F]Fluorination of (Mesityl)(aryl)iodonium Salts"; Org. Lett. (2014) 16, pp. 3224-3227.
Jeschke, "The Unique Role of Fluorine in the Design of Active Ingredients for Modem Crop Protection"; ChemBioChem (2004) 5, pp. 570-589.
Kalow and Doyle, "Enantioselective Ring Opening of Epoxides by Fluoride Anion Promoted by a Cooperative Dual-Catalyst System"; J. Am. Chem. Soc. (2010) 132, pp. 3268-3269.
Kee et al., "Selective fluorination of alkyl C—H bonds via photocatalysis"; Chem. Commun. (2014) 50, pp. 8211-8214.
Komuro et al., "Application of Chemical P-450 Model Systems to Studies on Drug Metabolism"; J. Pharmacobio-Dyn. (1992) vol. 15, pp. S89-S89.

(56) References Cited

OTHER PUBLICATIONS

Komuro et al., "Oxidative Decarboxylation of carboxylic Acids by Iron Porphyrin—Iodosylbenzene System"; Tetrahedron Lett. (1992) vol. 33, No. 34, pp. 4949-4952.

Laitar et al., "A Carbene-Stabilized Gold(I) Fluoride: Synthesis and Theory"; Organometallics (2005) 24, pp. 4503-4505.

Lauer and Wu, "Palladium-Catalyzed Allylic Fluorination of Cinnamyl Phosphorothioate Esters"; Org. Lett. (2012) vol. 14, No. 19, pp. 5138-5141.

Lee et al., "Nickel-Mediated Oxidative Fluorination for PET with Aqueous [18F] Fluoride"; J. Am. Chem. Soc. (2012) 134, pp. 17456-17458.

Lee et al., "A Fluoride-derived Electrophilic Late-Stage Fluorination Reagent for PET Imaging"; Science (2011) 334 (6056), pp. 639-642.

Leffler et al., "Substituent Effects on the Rate and Mechanism of the Decomposition of Phenyliodine Dicarboxylates"; J. Am. Chem. Soc. (1972) 94:15, pp. 5339-5341.

Leung et al., "Photo-fluorodecarboxylation of 2-Aryloxy and 2-Aryl Carboxylic Acids"; Angew. Chem. Int. Ed. (2012) 51, pp. 10804-10807.

Li et al., "Convergent 18F radiosynthesis: A new dimension for radiolabelling"; Chem. Sci. (2011) 2, pp. 123-131.

Liang et al., "Introduction of Fluorine and Fluorine-Containing Functional Groups"; Angew. Chem. Int. Ed. (2013) 52, pp. 8214-8264.

Lindsey and Wagner, "Investigation of the Synthesis of Ortho-Substituted Tetraphenylporphyrins"; J. Org. Chem. (1989) 54, 828-836.

Liu and Groves, "Manganese-Catalyzed Oxidative Benzylic C—H Fluorination by Fluoride Ions"; Angew. Chem. Int. Ed. (2013) 52, pp. 6024-6027.

Liu et al., "Oxidative aliphatic C—H fluorination with manganese catalysts and fluoride ion"; Nat. Protoc. (2013) vol. 8, No. 12, pp. 2348-2354.

Liu et al., "Oxidative Aliphatic C—H Fluorination with Fluoride Ion Catalyzed by a Manganese Porphyrin"; Science (2012) vol. 337, pp. 1322-1325.

Liu et al., "A simple method for chemoselective phenol alkylation"; ScienceDirect, Tetrahedron Lett. (2007) 48, pp. 7380-7382.

Lozano et al., "Organocatalyzed Enantioselective Fluorocyclizations"; Angew. Chem. Int. Ed. (2011) 50, pp. 8105-8109.

Macneil and Burton, "Generation of trifluoromethylcopper from chlorodifluoroacetate"; J. Fluorine Chem. (1991) 55, pp. 225-227.

Mathew and Warkentin, "Rate constants for abstraction of bromine from bromotrichloromethane by butyl, cyclopropylmethyl, and phenyl radicals in solution" Can. J. Chem. (1988) 66, pp. 11-16.

Mazzotti et al., "Palladium(III)-Catalyzed Fluorination of Arylboronic Acid Derivatives"; J. Am. Chem. Soc. (2013) 135 (28), pp. 14012-14015.

McMurtrey et al., "Pd-Catalyzed C—H Fluorination with Nucleophilic Fluoride"; Org. Lett. (2012) vol. 14, No. 16, pp. 4094-4097.

Miller et al., "Synthesis of 11C, 18F, 15O, and 13N Radiolabels for Positron Emission Tomography"; Angew. Chem. Int. Ed. (2008) 47, pp. 8998-9033.

Mizuta et al., "Catalytic Decarboxylative Fluorination for the Synthesis of Tri- and Difluoromethyl Arenes"; Org. Lett. (2013) 15, pp. 2648-2651.

Muller et al., "Fluorine in Pharmaceuticals: Looking Beyond Intuition"; Science (2007) 317, pp. 1881-1886.

Neese, "Importance of Direct Spin—Spin Coupling and Spin-Flip Excitations for the Zero-Field Splittings of Transition Metal Complexes: A Case Study"; J. Am. Chem. Soc. (2006) 128, pp. 10213-10222.

O'Hagan, "Understanding organofluorine chemistry. An introduction to the C—F bond"; Chem. Soc. Rev. (2008) 37, pp. 308-319.

Patrick et al., "Fluorodecarboxylation with Xenon Difluoride"; J. Org. Chem. (1983) 48, pp. 4158-4159.

Pitts et al., "Direct, Catalytic Monofluorination of sp3 C—H Bonds: A Radical-Based Mechanism with Ionic Selectivity"; J. Am. Chem. Soc. (2014) 136, pp. 9780-9791.

Prager and Schafer, "Potential GABAB Receptor Antagonists. X*The Synthesis of Further Analogues of Baclofen, Phaclofen and Saclofen"; Aust. J. Chem. (1997) 50, pp. 813-823.

Purser et al., "Fluorine in medicinal chemistry"; Chem. Soc. Rev. (2008) 37, pp. 320-330.

Qiao et al., "Decarboxylative Fluorination Strategies for Accessing Medicinally-relevant Products"; Curr. Top. Med. Chem. (2014) 14, pp. 966-978.

Rauniyar et al., "Asymmetric Electrophilic Fluorination Using an Anionic Chiral Phase-Transfer Catalyst"; Science (2011) 334, pp. 1681-1684.

Ye and Sanford, "Mild Copper-Mediated Fluorination of Aryl Stannanes and Aryl Trifluoroborates"; J. Am. Chem. Soc. (2013) 135, pp. 4648-4651.

Roberts and Selby, "The Influence of Substituent Groups on Ring Scission. Part 1. The Ring Scission of Some Unsymmetrically Substituted Glutaric Anhydrides"; J. Chem. Soc. (1951) pp. 2335-2339.

Roxburgh et al., "An Efficient New Synthesis of Racemic Cetiedil and a Novel Route to α-Ketocarboxylic Acids Utilising Mild Conditions"; Synlett (2007) pp. 1211-1214.

Rueda-Becerril et al., "Fluorine Transfer to Alkyl Radicals"; J. Am. Chem. Soc. (2012) 134, pp. 4026-4029.

Rueda-Becerril et al., "Direct C—F Bond Formation Using Photoredox Catalysis"; J. Am. Chem. Soc. (2014) 136, pp. 2637-2641.

Ruhl et al., "Cu(I)-mediated 18F-trifluoromethylation of arenes: Rapid synthesis of 18F-labeled trifluoromethylarenes"; Chem. Commun. (2014) 50, pp. 6056-6059.

Shi et al., "A Theoretical Study on C—COOH Homolytic Bond Dissociation Enthalpies"; J. Phys. Chem. A (2010) 114, pp. 6263-6272.

Shibata et al., "A Fundamentally New Approach to Enantioselective Fluorination Based on Cinchona Alkaloid Derivatives/Selectfluor Combination"; J. Am. Chem. Soc. (2000) 122, pp. 10728-10729.

Smart, "Fluorine substituent effects (on bioactivity)"; J. Fluorine Chem. (2001) 109, pp. 3-11.

Stang et al., "Acetylenic Esters. Preparation and Characterization of Alkynyl Carboxylates via Polyvalent Iodonium Species"; J. Am. Chem. Soc. (1988) 110, pp. 3272-3278.

Steiner et al., "Direct Asymmetric α-Fluorination of Aldehydes"; Angew. Chem. Int. Ed. (2005) 44, pp. 3706-3710.

Tang et al., "Silver-Catalyzed Late-Stage Fluorination"; J. Am. Chem. Soc. (2010) 132, pp. 12150-12154.

Tangestaninejad and Mirkhani, "Efficient and Mild Oxidative Decarboxylation of Aryl-substituted Carboxylic Acids by Iron and Manganese Porphyrin Periodate Systems"; J. Chem. Res. (1998) pp. 820-821.

Topczewski et al., "Iridium-Catalyzed Allylic Fluorination of Trichloroacetimidates"; J. Am. Chem. Soc. (2011) 133, pp. 19318-19321.

Tredwell et al., "A General Copper-Mediated Nucleophilic 18F Fluorination of Arenes"; Angew. Chem. Int. Ed. (2014) 53, pp. 7751-7755.

Truong et al., "Copper-Catalyzed, Directing Group-Assisted Fluorination of Arene and Heteroarene C—H Bonds"; J. Am. Chem. Soc. (2013) 135, pp. 9342-9345.

Umemoto and Tomita, "N-Fluoropyridinium Triflate and its Analogs, the First Stable 1:1 Salts of Pyridine Nucleus and Halogen Atom"; Tetrahedron Lett. (1986) 27, pp. 3271-3274.

van der Born et al., "A Universal Procedure for the [18F] Trifluoromethylation of Aryl Iodides and Aryl Boronic Acids with Highly Improved Specific Activity"; Angew. Chem. Int. Ed. (2014) 53, pp. 11046-11050.

Yang et al., "Synthesis and Immunosuppressive Activity of New Artemisinin Derivatives. 1. [12(β or α)-Dihydroartemisininoxy]phen(ox)yl Aliphatic Acids and Esters"; J. Med. Chem. (2005) 48, pp. 4608-4617.

Watson et al., "Formation of ArF from LPdAr(F): Catalytic Conversion of Aryl Triflates to Aryl Fluorides"; Science (2009) 325, pp. 1661-1664.

(56) References Cited

OTHER PUBLICATIONS

Wu, "Review of recent advances in nucleophilic C—F bond-forming reactions at sp3 centers"; Tetrahedron Lett. (2014) 55, pp. 4289-4294.
Banks et al., "1-Alkyl-4-fluoro-1, 4-diazoniabicyclo[2.2.2] octane Salts: a Novel Family of Electrophilic Fluorinating Agents"; J. Chem. Soc., Chem. Commun. (1992), pp. 595-596.
Benedetto et al., "Asymmetric 18 F-fluorination for applications in positron emission tomography"; Chem. Sci. (2013) 4, pp. 89-96.
R. Franz, "Ueber Trishydrofluoride Tertiaerer Amine and Ihren Einsatz Als Fluorierungsmittel" (English Translation: "About Trihydrofluoride Tertiary Amines and Your Use as Fluorinating") with English Translation of the summary.
Hazari et al., "Palladium-Catalyzed Substitution of Allylic Fluorides"; Angew. Chem. Int. Ed. 2009, 48, pp. 1296-1299.
Hooker, "Synthesis and Evaluation of Methylated Arylazepine Compounds for PET Imaging of 5 HT2c Receptors"; Curr. Opin. Chem. BGiol. (2010) 14, pp. 105-111.
Katcher and Doyle, "Palladium-Catalyzed Asymmetric Synthesis of Allylic Fluorides"; J. Am. Chem. Soc., (2010) vol. 132, pp. 17402-17404.
Wang et al., "Versatile Pd(Otf)2 2H2O-Catalyzed Ortho-Fluorination Using NMP as a Promotor"; J. Am. Chem. Soc. (2009) 131, pp. 7520-7521.
Xia et al., "Visible Light-Promoted Metal-Free sp3-C—H Fluorination"; Chem. Commun. (2014) 50, pp. 11701-11704.
Xia et al., "Visible Light-Promoted Metal-Free C—H Activation: Diarylketone-Catalyzed Selective Benzylic Mono- and Difluorination"; J. Am. Chem. Soc. (2013) 135, pp. 17494-17500.
Xiong et al., "Improved Anti-Osteoporosis Potency and Reduced Endometrial Membrane Hyperplasia During Hormone Replacement Therapy with Estrogen-RGD Peptide Conjugates"; J. Med. Chem. (2007) 50, pp. 3340-3353.
Yang et al., "Synthesis and immunosuppressive activity of new artemisinin derivatives. Part 2: 2-[12(β or α)-Dihydroartemisinoxymethyl-(or 1'-ethyl)] phenoxyl propionic acids and esters"; Bioorg. Med. Chem. (2006) 14, pp. 8043-8049.
Karimipour et al., Oxidative Decarboxylation of Carboxylic Acids with Tetrabutylammonium Periodate Datalyzed by Manganese (III) Meso-Tetraarylporphyrins: Effects of Metals, Meso-substitutents, and Anionic Axial Ligands, Chin. J. Catal, vol. 28(11), 940-946. (2007).
Takamatsu et al., Improved synthesis of 9-(2,3-dideoxy-2-fluoro-D-threo-pentofuranosyl)adenine (FddA) using triethylamine trihydrofluoride, Tetrandron Letters, 42, 2321-2324. (2001).
Wei et al., Oxidative Aliphatic C—H Fluorination with Fluoride Ion Catalyzed by a Manganese Porphyrin, Science, 337, 1322-1325. (2012).

* cited by examiner

US 10,974,235 B2

TARGETED, METAL-CATALYZED FLUORINATION OF COMPLEX COMPOUNDS WITH FLUORIDE ION VIA DECARBOXYLATION

CROSS REFERENCE TO RELATED APPLICATIONS

This application is a divisional of U.S. patent application Ser. No. 15/019,673, which was filed Feb. 9, 2016 as a continuation-in-part of U.S. patent application Ser. No. 14/239,719, which was filed Apr. 8, 2014 and was a 35 U.S.C § 371 national stage of International Patent Application No. PCT/US2012/051628, which was filed Aug. 20, 2012. U.S. patent application Ser. No. 14/239,719 claimed the benefit of U.S. Provisional Application No. 62/113,847, which was filed Feb. 9, 2015. International Patent Application No. PCT/US2012/051628 claimed the benefit of U.S. Provisional Application No. 61/525,301, which was filed Aug. 19, 2011, U.S. Provisional Application No. 61/639,523, which was filed Apr. 27, 2012 and U.S. Provisional Application No. 61/679,367, which was filed Aug. 3, 2012. All of the above applications are incorporated herein by reference as if fully set forth.

This invention was made with government support under Grant No. CHE-0616633 awarded by the National Science Foundation. The government has certain rights in this invention.

FIELD

The disclosure relates to methods for decarboxylative fluorination of compounds, compositions that include the fluorinated compounds thus produced and uses thereof.

BACKGROUND

Organofluorine compounds are of significant importance for the agrochemical and pharmaceutical industries as well as for PET imaging applications.[1] Despite the broad impact of organofluorine compounds and the intrinsic strength of the C—F bond, the incorporation of fluorine into organic molecules remains challenging.[1e, 2] Conventional fluorination methods typically involve harsh reaction conditions, displaying poor functional group tolerance and low selectivity.[2b] These limitations have inspired the development of a number of new methods, especially catalytic approaches, for constructing a C—F bond.

The majority of these newly-developed methods are based on electrophilic fluorination reagents (F$^+$), such as Selectfluor and other N-fluoroammonium analogs,[4] N-fluoropyridinium salts (NFPs),[5] and N-fluorosulfonamides.[6]

For catalytic fluorinations with fluoride-based reagents (F$^-$),[3a] only a handful of reactions have been developed for the synthesis of aryl and heteroaryl fluorides,[7] alkenyl fluorides,[8] allylic fluorides,[9] fluorohydrins,[10] $^{18}$F-labeled trifluoromethyl aromatics,[11] and benzylic fluorides.[12]

A general catalytic method for constructing aliphatic C—F bonds with simple nucleophilic fluoride remains a challenging task.[13] An efficient aliphatic C—H fluorination reaction that employed manganese tetramesitylporphyrin, Mn(TMP)Cl, as the catalyst and silver fluoride/tetrabutylammonium fluoride trihydrate (TBAF.3H$_2$O) as the fluoride source was reported.[14] The reaction was shown to proceed through a trans-difluoromanganese(IV) porphyrin complex that served as the fluorine transfer agent. Insights gained from the facile capture of substrate carbon radicals by F—Mn(IV)—F species led to the development of benzylic C—H fluorination reactions using manganese salen catalysts.[15] The first $^{18}$F labelling reaction of aliphatic C—H bonds with no-carrier-added [$^{18}$F]fluoride and Mn(salen) catalysts was also reported.[16]

SUMMARY

In an aspect, the invention relates to a method of targeted fluorination. The method comprises combining a monofluoro-aryl iodine-(III) carboxylate and a manganese catalyst.

In an aspect, the invention relates to a method of targeted fluorination of a compound containing a carboxyl group. The method includes combining the compound, a nucleophilic fluoride source, a manganese catalyst, a solvent and an iodine (III) oxidant.

In an aspect, the invention relates to a method of direct radioactive labeling of a compound containing a carboxyl group. The method includes combining a compound containing a carboxyl group, a nucleophilic, radioactive fluoride source, a manganese catalyst, a solvent and an iodine (III) oxidant.

In an aspect, the invention relates to a method of visualization. The method comprises radioactively labeling a compound containing a carboxylic group by any one of the methods described herein. The fluorine radioisotope includes $^{18}$F and a product produced by the method is an $^{18}$F imaging agent. The method also comprises administering the imaging agent to a patient and performing positron emission tomography on the patient.

In an aspect, the invention relates to a method of targeted fluorination. The method comprises combining a monofluoro-aryl iodine-(III) carboxylate and a manganese catalyst.

BRIEF DESCRIPTION OF THE DRAWINGS

The following detailed description of embodiments of the present invention will be better understood when read in conjunction with the appended drawings. For the purpose of illustrating the invention, there are shown in the drawings particular embodiments. It is understood, however, that the invention is not limited to the precise arrangements and instrumentalities shown. In the drawings:

FIG. 2A illustrates fluorination of compound 29: bis(α-methylbenzeneacatato)(phenyl)-λ$^3$-iodane. FIG. 2B illustrates the $^{19}$F-NMR spectrum of a solution of Mn(TMP)Cl, Et$_3$N.3HF and compound 30a: 2-phenylpropanoic acid. FIG. 2C illustrates potential energy surfaces (kcal/mol) for the formation of carboxyl radicals through the interaction of an iodine(III) carboxylate complex and a manganese(III) porphyrin. T and Q refer to triplet and quintet states, respectively.

FIG. 3A illustrates $^{19}$F NMR of a solution created by addition of PhIO (0.3 equiv.) into the CD$_2$Cl$_2$ solution of acid 30a (1.0 equiv.) and Et$_3$N.3HF (1.0 equiv). FIG. 3B illustrates $^{19}$F NMR of the solution upon titration of the CD$_2$Cl$_2$ solution of iodobenzene dicarboxylate 29 (1.0 equiv.) with Et$_3$N.3HF (0.1 equiv.). FIG. 3C illustrates $^{19}$F NMR of the solution upon titration of the CD$_2$Cl$_2$ solution of iodobenzene dicarboxylate 29 (1.0 equiv.) with Et$_3$N.3HF (0.4 equiv.). FIG. 3D illustrates ¹⁹F NMR of the solution upon titration of CD₂Cl₂ solution of iodobenzene dicarboxylate 29 (1.0 equiv.) with Et₃N.3HF (1.5 equiv.).

FIG. 6A illustrates the ¹H NMR spectrum of 1-(1-fluoroethyl)-4-isobutylbenzene. FIG. 6B illustrates the ¹³C NMR spectrum of 1-(1-fluoroethyl)-4-isobutylbenzene. FIG. 6C illustrates the ¹⁹F NMR spectrum of 1-(1-fluoroethyl)-4-isobutylbenzene.

FIG. 7 illustrates the radio-TLC scan of compound ¹⁸F-18. FIG. 8 illustrates the radio-TLC scan of compound ¹⁸F-14. FIG. 9 illustrates the radio-TLC scan of compound ¹⁸F-25. FIG. 10 illustrates the radio-TLC scan of compound ¹⁸F-19. FIG. 11 illustrates the radio-TLC scan of compound ¹⁸F-8. FIG. 12 illustrates the radio-TLC scan of compound ¹⁸F-17. FIG. 13 illustrates the radio-TLC scan of compound ¹⁸F-15. FIG. 14 illustrates the radio-TLC scan of compound ¹⁸F-5.

DETAILED DESCRIPTION OF EMBODIMENTS

Figure 1:
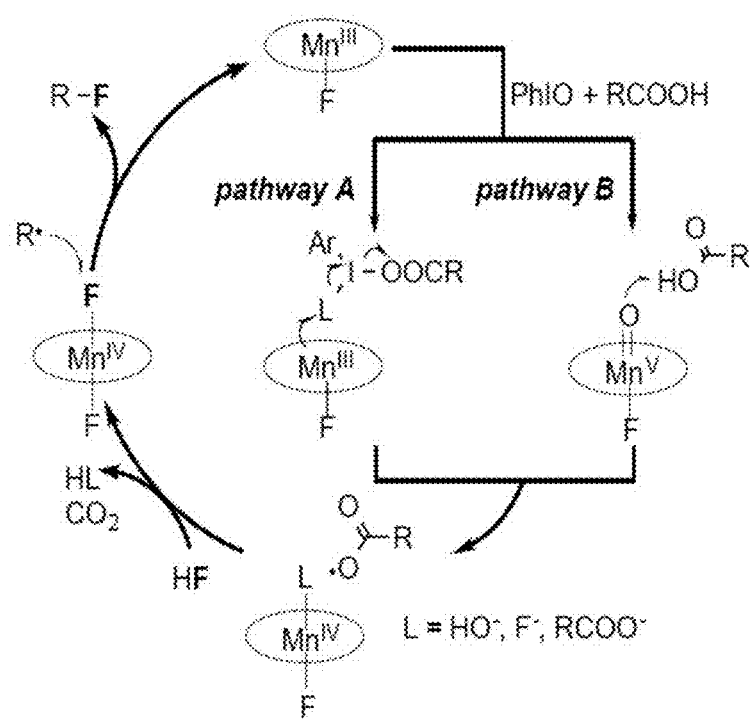
FIG. 1 illustrates mechanistic probes of fluorine transfer.

Certain terminology is used in the following description for convenience only and is not limiting. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B, or C as well as any combination thereof.

A catalytic decarboxylative fluorination reaction based on nucleophilic fluoride is provided. The method may allow facile replacement of various aliphatic carboxylic acid groups with fluorine. Moreover, the potential of this method for PET radiochemistry has been demonstrated by the successful ¹⁸F labelling of a variety of carboxylic acids with radiochemical conversions (RCCs) up to 50%, representing a targeted decarboxylative ¹⁸F labelling method with no-carrier-added [¹⁸F]fluoride. Mechanistic probes suggest that the reaction proceeds through the interaction of the manganese catalyst with iodine(III) carboxylates formed in situ from iodosylbenzene and the carboxylic acid substrates.

The method may allow the introduction of fluorine from fluoride ion into complex molecules via targeted decarboxylation of a previously existing or installed carboxylic acid group. The method may be particularly advantageous for ¹⁸F labeling of functionally complex molecules for PET scanning applications in pharmacokinetics and in vivo imaging. The method may allow selective incorporation of fluorine, including [¹⁸F]fluorine, into compounds, drug candidates, and biomolecules that contain other easily oxidizable groups.

An embodiment provides a method of targeted fluorination of a compound containing a carboxyl group. The method may comprise combining the compound, a nucleophilic fluoride source, a manganese catalyst, a solvent and an oxidant. In an embodiment, combining can be done in any order. The manganese catalyst may be a manganese porphyrin or a manganese salen. The manganese porphyrin may be in a manganese(III) porphyrin. The manganese(III) porphyrin may be but is not limited to Mn(TMP)Cl, Mn(TTP), and Mn(TDCPP)Cl. The nucleophilic fluoride source may be but is not limited to trialkyl amine trihydrofluoride designated as R₃N(HF)₃. R— may be ethyl group. The nucleophilic fluoride source may be triethylamine trihydrofluoride. The solvent may be or may include but is not limited to acetonitrile, acetone, dichloromethane, or 1,2-dichloroethane. The oxidant may be an iodine (III) oxidant. The iodine (III) oxidant may be or comprise at least one of iodosylbenzene (PhIO), iodobenzene (PhI(OPiv)₂), or iodobenzene diacetate (PhI(OAc)₂). The iodine (III) oxidant may be at least one of dichloroiodobenzene, Bis(tert-butylcarbonyloxy)iodobenzene, iodosylmesitylene, [Bis(trifluoroacetoxy) iodo]benzene, [Hydroxy(tosyloxy)iodo]benzene, iodomesitylene diacetate, iodosylpentafluorobenzene, [Bis(trifluoroacetoxy) iodo] pentafluoro benzene, 3,3-dimethyl-1-fluoro-1,2 benziodoxole, or (2-tert-butylsulfonyl) iodobenzene. The iodine (III) oxidant may be any one of the oxidants having chemical structures shown below:

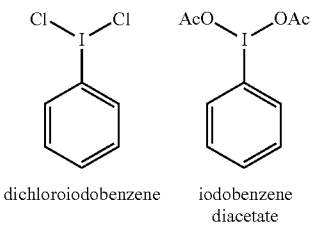

dichloroiodobenzene   iodobenzene diacetate

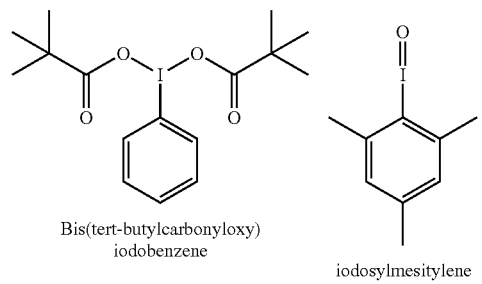

Bis(tert-butylcarbonyloxy) iodobenzene iodosylmesitylene

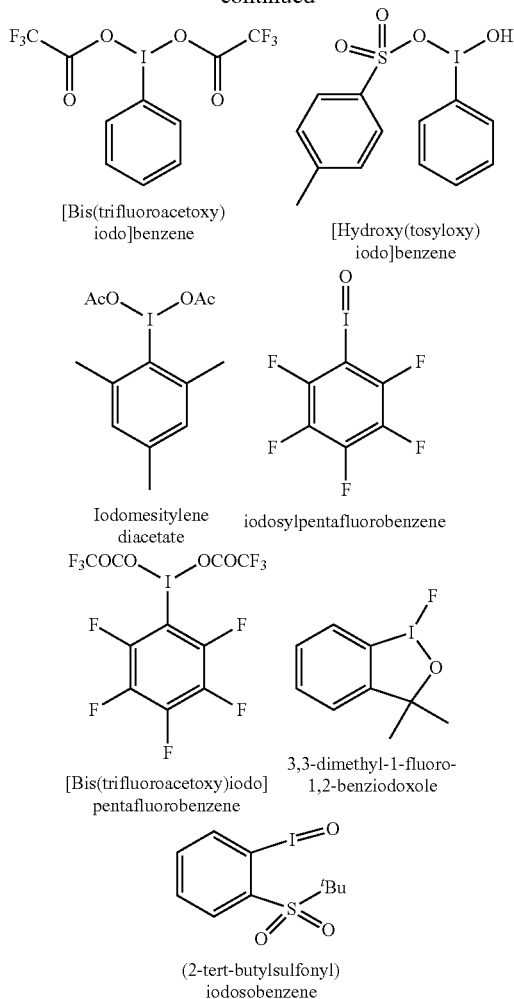

In an embodiment, the step of combining may comprise mixing the manganese catalyst, the nucleophilic fluoride source, the compound and the solvent under an inert atmosphere to form a first mixture. The step of combining may comprise adding an iodine (III) oxidant to the first mixture to form a second mixture. The molar ratio of the iodine (III) oxidant to the nucleophilic fluoride source may be adjusted to one of 4 eq.:1 eq., 3 eq.:1 eq., 2 eq.:1 eq., 1 eq.:1 eq. or 0.5 eq.:1 eq., or any ratio in a range between any two of the foregoing (endpoints inclusive). For example, the iodine (III) oxidant to the nucleophilic source molar ratio may be a value less than any integer or non-integer number selected from 4 eq.:1 eq. to 0.5 eq.:1 eq. The iodine (III) oxidant to the nucleophilic source molar ratio may be equal to 4 eq.:1 eq., 3 eq.:1 eq., 2 eq.:1 eq., 1 eq.:1 eq. or 0.5 eq.:1 eq. or any ratio in a range between any two of the foregoing (endpoints inclusive). For example, the iodine (III) oxidant to the nucleophilic source ratio may be a value equal to any integer or non-integer number in the range from 4 eq.:1 eq. to 0.5 eq:1 eq. The iodine (III) oxidant may be solid and added to the first mixture over a period of time. The volume of the solvent added to the mixture may be 1 mL, or any volume needed to dissolve other components of the mixture. As used herein, "eq." or "equivalent" refers to the number of moles of fluoride in comparison to the number of moles of substrate. In case of the triethylamine trihydrofluoride TREAT-HF (Et$_3$N.3HF), this compound has three equivalents of fluoride per molecule. In alternate embodiments, the oxidant may be in vast excess to the nucleophilic fluoride source.

In an embodiment, the step of adding the iodine (III) oxidant may occur over a period of 45 minutes to 90 minutes. The step of adding may occur over a period from 45 minutes to 50 minutes, from 50 minutes to 55 minutes, from 55 minutes to 60 minutes, from 60 minutes to 65 minutes, from 65 minutes to 70 minutes, from 70 minutes to 75 minutes, from 75 minutes to 80 minutes, from 80 minutes to 85 minutes and from 85 minutes to 90 minutes. The time period for the step of adding the iodine (III) oxidant may be in a range between any two integer value between 45 minutes and 90 minutes. The time period for the step of adding the (iodine III) oxidant may be 45 minutes.

The manganese catalyst may be added to the mixture at a concentration from 2.0 mol. % to 10 mol. %. As used herein, molar % refers to (moles of manganese catalyst/moles of substrate)×100%. The concentration of the manganese catalyst may be in a range from 2.0 mol. % to 10 mol. %. The concentration may be 2.0 mol. %, 2.5 mol. %, 3.0 mol. %, 3.5 mol. %, 4.0 mol. %, 4.5 mol. %, 5.0 mol. %, 5.5 mol. %, 6.0 mol. %, 6.5 mol. %, 7.0 mol. %, 7.5 mol. %, 8.0 mol. %, 8.5 mol. %, 9.0 mol. %, 9.5 mol. %, or 10 mol. %, or any value between any two of the foregoing concentration points. The concentration of the manganese catalyst may be at least 2.0 mol. %, at least 2.5 mol. %, at least 3.0 mol. %, at least 3.5 mol. %, at least 4.0 mol. %, at least 4.5 mol. %, at least 5.0 mol. %, at least 5.5 mol. %, at least 6.0 mol. %, at least 6.5 mol. %, at least 7.0 mol. %, at least 7.5 mol. %, at least 8.0 mol. %, at least 8.5 mol. %, at least 9.0 mol. %, at least 9.5 mol. %, or at least 10 mol. %, or at least any value between any two of the foregoing concentration points.

The compound containing a carboxyl group may be added to the mixture at a concentration from 0.25 mmol to 1.00 mmol. The concentration of the manganese catalyst may be in a range from 0.25 mmol to 1.00 mmol. The concentration may be 0.25 mmol, 0.30 mmol, 0.35 mmol, 0.40 mmol, 0.45 mmol, 0.50 mmol, 0.55 mmol, 0.60 mmol, 0.65 mmol, 0.70 mmol, 0.75 mmol, 0.80 mmol, 0.85 mmol, 0.90 mmol, 0.95 mmol, or 1.00 mmol, or any value between any two of the foregoing concentration points. The concentration of the manganese catalyst may be at least 0.25 mmol, at least 0.30 mmol, at least 0.35 mmol, at least 0.40 mmol, at least 0.45 mmol, at least 0.50 mmol, at least 0.55 mmol, at least 0.60 mmol, at least 0.65 mmol, at least 0.70 mmol, at least 0.75 mmol, at least 0.80 mmol, at least 0.85 mmol, at least 0.90 mmol, at least 0.95 mmol, or at least 1.00 mmol, or at least any value between any two of the foregoing concentration points. The concentration may be 0.5 mmol.

In an embodiment, the step of combining may further comprise adding benzoic acid. The concentration of the benzoic acid may be in a range from 0.125 M to 0.5 M. The concentration may be 0.125 M, 0.15 M, 0.175 M, 0.2 M, 0.225M, 0.25 M, 0.275 M, 0.3 M, 0.325M, 0.35 M, 0.375 M, 0.4 M, 0.425 M, 0.45 M, 0.475 M, or 0.5 M, or any value between any two of the foregoing concentration points. The concentration of the manganese catalyst may be in a range from 0.125 M to 0.5 M. The concentration may be at least 0.125 M, at least 0.15 M, at least 0.175 M, at least 0.2 M, at least 0.225 M, at least 0.25 M, at least 0.275 M, at least 0.3 M, at least 0.325M, at least 0.35 M, at least 0.375 M, at least 0.4 M, at least 0.425 M, at least 0.45 M, at least 0.475 M, or at least 0.5 M, or at least any value between any two of the foregoing concentration points. The benzoic acid may be added at a concentration of 0.25 M.

In an example, 11 mg of Mn(TMP)Cl Catalyst (0.0125 mmol, 2.5 mol %) was combined with acid substrate (0.5 mmol), and 0.1 mL of Et$_3$N.3HF (0.61 mmol, 1.2 equiv.) in a 5 mL vial that was placed under an atmosphere of N$_2$ and stirred. Thirty milligram of benzoic acid 0.25 mmol, 0.5 equiv.) and 1.0 mL of 1,2-dichloroethane (DCE) were sequentially added to the solution. The resulting solution was heated to 45° C. Under a stream of N$_2$, 370 mg of iodosylbenzene (1.6 mmol, 3.3 equiv.) were added to the solution for a period from 45 minutes to 1.5 hours. The reaction was monitored by GC/MS analysis with 25 mg naphthalene (0.195 mmol, 0.39 equiv.) added as internal standard. After the addition of iodosylbenzene, the solution was cooled to room temperature and the product was separated from the reaction residue by silica gel column chromatography.

In an embodiment, the step of combining may comprise adding a phase transfer catalyst. The phase transfer catalyst may be 18-crown-6. The phase transfer catalyst may be one or more of other crown ethers. The one or more of other crown ethers may be dibenzo-18-crown-6 or diaza-18-crown-6. The phase transfer catalysts may be one or more phase transfer catalysts of the cryptand family. The phase transfer catalyst of the cryptand family may be kryptofix 222 or kryptofix 222B.

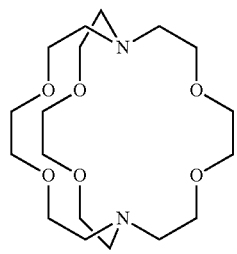

Kryptofix 222

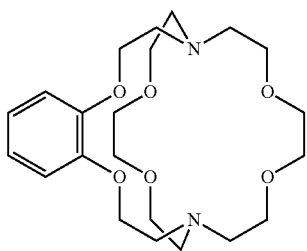

Kryptofix 222B

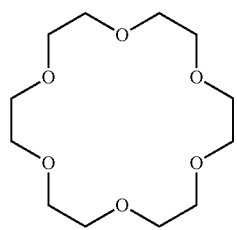

18-crown-6

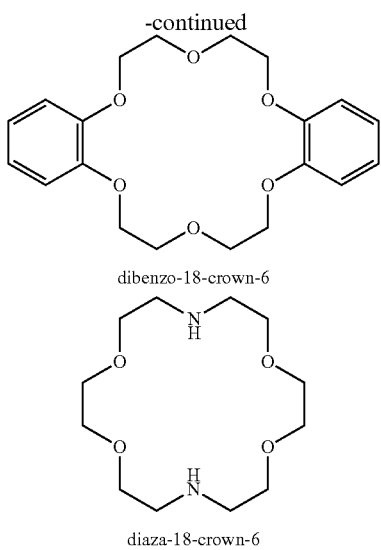

dibenzo-18-crown-6 diaza-18-crown-6

In an embodiment, the step of combining may comprise mixing the nucleophilic fluoride source, the phase transfer catalyst, the solvent, the compound and an iodine (III) oxidant under an anaerobic atmosphere to form a first mixture. The anaerobic atmosphere may be an inert atmosphere. The inert atmosphere may be an N$_2$ or Ar atmosphere. The step of combining may comprise adding the manganese catalyst to the first mixture to form a second mixture. In an alternate embodiment, the foregoing mixing may occur in atmospheric air.

In another example, 1 mg of KF (17.0 µmol, 1 equiv.) was combined with 16 mg of 18-crown-6 (30.2 µmol, 1.8 equiv.) in a 4 ml vial and stirred. Two milliliters of acetonitrile (ACN) were added to the solution before sonication for 2 minutes. After sonication, 83 mg of 2,3-diphenylpropionic acid (367.2 µmol, 21 equiv.) and 38 mg of iodosylbenzene (PhIO) (172.7 µmol, 10 equiv.) were added to the vial and the solution therein was stirred for 2 minutes at room temperature. Six mg of Mn(TMP)Cl (6.8 µmol, 0.4 equiv.) were then added to the solution to catalyze the reaction. The resulted solution was stirred at 45° C. for 8 minutes. After cooling to room temperature, the solvent was evaporated and 10 µL fluorobenzene was added as internal standard. The yield was determined by $^{19}$F NMR.

In an embodiment, the method may include reacting the compound containing a carboxylic group, the oxidant, the nucleophilic fluorine source and the solvent for a reaction time of 2 minutes to 30 minutes. The reaction may be allowed to proceed from 2 minutes to 5 minutes, from 5 minutes to 10 minutes, from 10 minutes to 15 minutes, from 15 minutes to 20 minutes, from 20 minutes to 25 minutes, and from 25 minutes to 30 minutes. The time period for reaction may be in a range between any two integer value between 10 minutes and 30 minutes. The reaction may be allowed to proceed for 2 minutes.

In an embodiment, the method may include reacting the compound, the nucleophilic fluorine source, the solvent, the iodine (III) oxidant and the manganese catalyst for a reaction time of 10 minutes to 30 minutes. The reaction may be allowed to proceed from 5 minutes to 10 minutes, from 10 minutes to 15 minutes, from 15 minutes to 20 minutes, from 20 minutes to 25 minutes, and from 25 minutes to 30 minutes. The time period for reaction may be in a range between any two integer value between 5 minutes and 30 minutes. The reaction may be allowed to proceed for 10 minutes.

The reaction may be allowed to proceed from 10 minutes to 15 minutes, from 15 minutes to 20 minutes, from 20 minutes to 25 minutes, from 25 minutes to 30 minutes, from 30 minutes to 35 minutes, from 35 minutes to 40 mintutes, from 40 minutes to 45 minutes, from 45 minutes to 50 minutes, from 50 minutes to 55 minutes, and from 55 minutes to 60 minutes. The time period for reaction may be in a range between any two integer value between 10 minutes and 60 minutes. The reaction may be allowed to proceed for 10 minutes.

In an embodiment, the method may comprise maintaining the first mixture at a temperature from 10° C. to 50° C. The temperature may be 45° C.

The method may comprise reaction temperatures between and including 10° C. and 50° C. The temperature may be in a range between any two integer value temperatures selected from 10° C. to 50° C. The temperature may be in a range between and including 10° C. and 20° C., 20° C. and 30° C., 30° C. and 40° C., 40° C. and 50° C. The temperature may be any one integer value temperature selected from those including and between 10° C. and 50° C. Temperatures between 25° C. and 50° C. may be used. The temperature may be any temperature including and between 25° C. and 50° C. The temperature ranges in this paragraph may also be provided in a method of radioactive labeling herein.

The compound containing a carboxyl group is also referred to as a substrate or target herein. Examplary compounds containing a carboxyl group include but are not limited to 2-(4-isobutylphenyl)propanoic acid, 2-(naphthalen-1-yloxy)acetic acid, 2,3-dihydrobenzo[b][1,4]dioxine-2-carboxylic acid, 2-(3-benzoyl phenyl)propanoic acid, 2-(1, 3-dioxoisoindolin-2-yl)-2-phenylacetic acid, 2-cyclo pentyl-2-phenylacetic acid, 2-(naphthalen-1-yl)pent-4-ynoic acid, 4-cyano-2-phenyl butanoic acid, 2-(4-(1-oxoisoindolin-2-yl)phenyl)propanoic acid, 2-(4-(bromomethyl) phenyl)propanoic, 2-(4-(allyloxy)phenoxy) acetic acid, 2-(4-(benzyloxy)phenyl) acetic acid, 2-(4-(5-(trifluoromethyl)pyridin-2-yloxy)phenoxy)propanoic acid, 2-(2,4-dichloro phenoxy) propanoic acid, 2-(naphthalen-2-yloxy)acetic acid, 2,3-diphenylpropanoic acid, 2-(1,3-dioxoisoindolin-2-yl)-3-phenylpropanoic acid, 2-phenylbutanoic acid, 2-(biphenyl-4-yl)acetic acid, 2,2-bis(4-chlorophenyl) acetic acid, 4-phenyl-2-(thiophen-3-yl)butanoic acid, 1-adamantanecarboxylic acid, (E)-2-(cinnamoyloxy)-2-phenylacetic acid, 2-((8R,9S,13S,14S)-13-methyl-17-oxo-7,8,9,11,12,13,14, 15,16,17-decahydro-6H-cyclopenta[α]phenanthren-3-yloxy)propanoic acid, or 2-[4-[[(3R,5aS, 6R,8aS,9R,10S, 12R, 12aR)-decahydro-3,6,9-trimethyl-3,12-epoxy-12H-pyrano[4,3-j]-1,2-benzodioxepin-10-yl]oxy]phenoxy]propanoic acid or derivatives, or analogs thereof. The term "derivative" or "analog" as used herein means the compound having one or several modifications in the structure of the precursor compound. One or several modifications in the structure of the precursor compound may include installment of a carboxyl group or a chemical group containing the carboxyl group on the structure of the precursor compound. One or several modifications in the structure of the precursor compound may include protection of one or several functional groups in the precursor compound with protecting groups. One or several modifications in the structure of the precursor compound may include replacement of one or several substituents in the precursor compound with other chemical groups.

In an embodiment, the compound containing a carboxyl group may be any one of the compounds 1-28 illustrated in Table 1 and Scheme 2, in which the fluorine moiety is replaced by a —COOH group. The compounds may be 1a: 2-(4-isobutylphenyl)propanoic acid; 2a: 2-(naphthalen-1-yloxy)acetic acid; 3a: 2,3-dihydrobenzo[b][1,4]dioxine-2-carboxylic acid; 4a: 2-(3-benzoylphenyl) propanoic acid; 5a: 2-(1,3-dioxoisoindolin-2-yl)-2-phenylacetic acid; 6a: 2-cyclopentyl-2-phenyl acetic acid; 7a: 2-(naphthalen-1-yl)pent-4-ynoic acid; 8a: 4-cyano-2-phenylbutanoic acid; 9a: 2-(4-(1-oxoisoindolin-2-yl)phenyl) propanoic acid; 10a: 2-(4-(bromomethyl) phenyl)propanoic acid; 11a: 2-(4-(allyloxy)phenoxy)acetic acid; 12a: 2-(4-(benzyloxy) phenyl)acetic acid; 13a: 2-(4-(5-(trifluoromethyl)pyridin-2-yloxy)phenoxy)propanoic acid; 14a: 2-(2,4-dichlorophenoxy)propanoic acid; 15a: 2-(naphthalen-2-yloxy)acetic acid; 16a: 2,3-diphenylpropanoic acid; 17a: 2-(1,3-dioxoisoindolin-2-yl)-3-phenyl propanoic acid; 18a: 2-phenylbutanoic acid; 19a: 2-(biphenyl-4-yl)acetic acid; 20a: 2,2-bis(4-chlorophenyl)acetic acid; 21a: 4-phenyl-2-(thiophen-3-yl)butanoic acid; 22a: 1-adamantanecarboxylic acid; 23a: 3-phenylpropanoic acid; 24a: 2-methyl-3-phenylpropanoic acid; 25a: 2,2-dicyclohexylacetic acid; 26a: (E)-2-(cinnamoyloxy)-2-phenylacetic acid; 27a: 2-((8R,9S,13S,14S)-13-methyl-17-oxo-7,8,9,11,12,13,14, 15,16,17-decahydro-6H-cyclopenta[α]phenanthren-3-yloxy)propanoic acid; 28a: 2-[4-[[(3R, 5aS,6R,8aS,9R,10S, 12R, 12aR)-decahydro-3,6,9-trimethyl-3,12-epoxy-12H-pyrano[4,3-j]-1,2-benzodioxepin-10-yl]oxy]phenoxy]propanoic acid.

The method may include manganese (III) porphyrin catalyzed decarboxylative fluorination where the nucleophilic fluoride source is trimethylamine trihydrofluoride ($Et_3N.3HF$). The method may include fluorinating a compound containing a carboxyl group in the presence of catalytic amount of Mn(TMP)Cl. An iodine (III) oxidant may be used. The iodine (III) oxidant may be at least one of iodosylbenzene (PhIO), iodobenzene ($PhI(OPiv)_2$) or iodobenzene diacetate ($PhI(OAc)_2$). Any other iodine (III) oxidant described herein may be used. For example, reaction of ibuprophen employing 1,2-discloroethane as a solvent by decarboxylative fluorination results in fluoro-ibuprophen in 50% conversion. When benzoic acid is added to the reaction, 65% of ibuprophen molecules are converted to fluoro-ibuprophen.

An embodiment provides a composition comprising a fluorinated product by any one of the methods described herein.

An embodiment provides a composition comprising 1-(1-fluoroethyl)-4-isobutylbenzene, fluoro(phenyl)methyl cinnamate, (8R,9S,13S,14S)-3-(1-fluoro ethoxy)-13-methyl-7, 8,9,11,12,13,15,16-octahydro-6H-cyclopenta[α]phenanthren-17(14H)-one, or decahydro-3,6,9-trimethyl-10-(4-(1-fluoroethoxy)phenoxy)-,(3R,5aS, 6R,8aS,9R,10S, 12R, 12aR)-3,12-Epoxy-12H-pyrano[4,3-j]-1,2-benzodioxepin).

An embodiment provides a composition comprising any one of the compounds 1-28 illustrated in Table 1 and Scheme 2. An embodiment provides a composition comprising any other compound, in which a carboxyl group is replaced by fluorine moiety.

The methods of carboxylative fluorination described herein are applicable to $^{18}F$ labeling of compounds containing a carboxyl group with [$^{18}F$]fluoride.

An embodiment provides a method of direct radioactive labeling of a compound containing a carboxyl group. The method may comprise combining the compound, a nucleophilic radioactive fluoride source, a manganese catalyst, a solvent and an iodine (III) oxidant. The method may be as described herein for any method herein of targeted fluorination of a compound containing a carboxyl group where the nucleophilic fluoride source comprises radioactive flouride. The radioactive fluoride may be [$^{18}$F]-fluoride. The [$^{18}$F]-fluoride may be a carrier-free [$^{18}$F]-fluoride. As used herein, the term "carrier-free" refers to the fluoride that is essentially free from stable isotopes of $^{19}$F. In carrier-free $^{18}$F fluoride, the radioactivity of the fluoride undiluted by non-radioactive $^{19}$F is higher. The carrier free [$^{18}$F-fluoride may be [$^{18}$F-fluoride having a specific activity higher than 1 Ci/µmol.

Embodiments include combining the compound containing a carboxyl group, the nucleophilic radioactive fluoride source, the manganese catalyst, the solvent and the iodine (III) oxidant in any order. In the method of direct radioactive labeling, the step of combining may include mixing the compound containing a carboxyl group and the iodine (III) oxidant to form a first mixture. The step of combining may also include mixing the nucleophilic radioactive fluoride source and the solvent to form the second mixture. The first mixture and the second may be combined; for example, by being added to the vial. The manganese catalyst may be subsequently added; for example, to the same vial. The step of combining may be carried out under open air.

The method of direct radioactive labeling may comprise obtaining [$^{18}$F]fluoride from a cyclotron as an aqueous [$^{18}$F] fluoride. The method may also comprise loading the aqueous [$^{18}$F] fluoride solution onto an ion exchange cartridge. The ion exchange cartridge may be an anion exchange cartridge. The method may also comprise releasing the [$^{18}$F] fluoride from the ion exchange cartridge before mixing the [$^{18}$F] fluoride with a solvent to form the second mixture. The solvent may be but is not limited to acetonitrile. The solvent may be part of a solution comprising a manganese catalyst.

In an embodiment, the method may include maintaining the compound, the iodine (III) oxidant, the nucleophilic fluorine source, the solvent and the manganese catalyst at a temperature of 25° C. to 100° C. The temperature may be in a range between any two integer value temperatures selected from 25° C. to 100° C. The temperature may be in a range and including 25° C. and 30° C., 30° C. and 40° C., 40° C. and 50° C., 50° C. and 60° C., 60° C. and 70° C., 70° C. and 80° C., 80° C. and 90° C., 90° C. and 100° C. The temperature may be any one integer value temperature selected from those including and between 25° C. to 100° C. Temperatures between 25° C. to 100° C. may be used. The temperature may be any temperature including and between 25° C. to 100° C. The temperature may be 45° C.

In an embodiment, the compound containing a carboxyl group may be added to a concentration from 0.02 mol/L to 0.40 mol/L. The nucleophilic fluorine source may be added to a concentration 20 µCi/ml to 500 mCi/ml. The manganese catalyst may be added to a concentration from 0.0004 mol/L to 0.01 mol/L. The solvent may be added to a volume from 0.05 mL to 1 mL. The oxidant may be added to a concentration from 0.01 mol/L to 0.2 mol/L. In an embodiment, the oxidant may be solid. Each of the foregoing concentration ranges may be subdivided. The concentration of the compound containing a carboxyl group may be subdivided between any two values chosen from 0.1 increments within the described range (endpoints inclusive). The concentration of the nucleophilic fluorine source may be subdivided between any two values chosen from 20 µCi increments within the described range (endpoints inclusive). The volume of the solvent may be subdivided between any two values chosen from 0.1 increments within the described range (endpoints inclusive). The concentration of the oxidant may be subdivided between any two values chosen from 0.05 increments within the described range (endpoints inclusive). The concentration of any one reactant may be a specific value within its respective ranges.

The methods of direct radioactive labeling herein may be compatible with typical "dry-down" procedures used in $^{18}$F chemistry. Embodiments of the method include "dry-down" procedures. Typically, the [$^{18}$F]fluoride solution obtained from a cyclotron is a very dilute aqueous solution. For large-scale (100 milli Curies to several Curies) radio-synthesis, removing water and redissolving the [$^{18}$F]fluoride in organic solution is generally required. As used herein, the term "dry-down procedure" refers to the procedure that includes iterative azeotropic evaporation of water from the very dilute [$^{18}$F]fluoride solution derived from a cycltron to obtain anhydrous [$^{18}$F]fluoride, which can be later dissolved in organic solution. Generally, 3 cycles of azeotropic evaporation are required to obtain anhydrous [$^{18}$F]fluoride. Each cycle may include adding 1 mL of anhydrous acetonitrile to the [$^{18}$F]fluoride source containing an inorganic base; e.g., K$_2$CO$_3$, and heating the resulting mixture to dryness at 108° C.

An embodiment includes a "dry-down free" method of direct radioactive labeling, wherein "dry-down" is not required but may be employed if desired. The term "dry-down free" procedure herein refers to the procedure, wherein the [$^{18}$F]fluoride loaded onto the ion exchange cartridge can be directly extracted by the solution of the manganese catalyst due to the strong binding between the catalyst and [$^{18}$F]fluoride, therefore bypassing the time-consuming azeotropic evaporation cycles ("dry-down" step). The method of direct radiolabeling may, thus, comprise loading the nucleophilic radioactive fluorine source onto an ion exchange cartridge. The ion exchange cartridge may be an anion exchange cartridge. The method may comprise releasing the nucleophilic radioactive fluorine source from the ion exchange cartridge by applying a solvent to the ion exchange cartridge. The solvent may be water. The solvent may be organic solution. The solvent me be part of a solution comprising a manganese catalyst. The manganese catalyst may be any manganese catalyst herein.

In an example, substrate or any compound containing a carboxyl group described herein (0.22 mmol) was combined with iodosylbenzene (0.068 mmol) in a 4 ml vial and stirred before labeling. An aqueous [$^{18}$F] fluoride solution was obtained from the cyclotron. A portion of this solution (40-50 µL, 4-5 mCi) was loaded on to an CHROMAFIX® PS cartridge to obtain a washed, purified and diluted [$^{18}$F] fluoride solution. Twenty five milliliters of the resulting washed [$^{18}$F]fluoride solution (125-150 µCi) was diluted with 3.0 mL acetonitrile to obtain [$^{18}$F]fluoride acetonitrile solution. 0.6 mL of this [$^{18}$F]fluoride acetonitrile solution was added to the vial containing the substrate and the oxidant. The resulting solution was stirred for 2 min at 50° C. Then 2 mg Mn(TMP)Cl catalyst (0.0023 mmol) was added to the solution. The vial was capped and stirred at 50° C. for 10 minutes. After 10 minutes, an aliquot of the reaction mixture was taken and spotted on a silica gel TLC plate. The plate was developed in an appropriate eluent and scanned with a Bioscan AR-2000 Radio TLC Imaging Scanner.

An embodiment provides a method of targeted fluorination. The method may comprise combining a mono-fluoro-aryl iodine-(III) carboxylate and a manganese catalyst. The manganese catalyst may be any one of the manganese catalysts described herein. The method may further comprise mixing a compound containing a carboxyl group, a nucleophilic fluoride source, a solvent and an iodine (III) oxidant to form the mono-fluoro-aryl iodine-(III) carboxylate prior to the step of combining. As used herein, the mono-fluoro-aryl iodine-(III) carboxylate refers to an intermediate compound. The compound, the solvent, or the iodine(III) oxidant may be any one of the compounds, solvents or the iodine (II) oxidants described herein.

In an embodiment, the nucleophilic fluoride source may be trialkyl amine trihydrofluoride. The trialkyl amine trihydrofluoride may be triethylamine trihydrofluoride. The step of combining may be performed under an inert atmosphere. The method of fluorination may be performed as the method of targeted decarboxylative fluorination.

In an embodiment, the nucleophilic fluoride source may be [$^{18}$F]-fluoride. The step of combining may be performed under air. The method of fluorination may be performed as the method of radioactive labeling.

An embodiment includes a composition comprising the product of any method of direct radiolabeling of a compound containing a carboxyl group herein. The product may be from the method as it is conducted on any target contained herein, or an analog thereof. The composition may comprise one or more of fluoro-ibuprofen (1-(1-fluoroethyl)-4-isobutylbenzene), fluoro-benzyl cinnamate (fluoro (phe nyl)methyl cinnamate), fluoro-estrone ((8R,9S,13S, 14S)-3-(1-fluoroethoxy)-13-me-thyl-7,8,9,11,12,13,15, 16-octahydro-6H-cyclopenta[α] phenanthren-17(14H)-one), or fluoro-artemisinin (decahydro-3,6,9-trimethyl-10-(4-(1-fluoroethoxy)phenoxy)-,(3R,5aS,6R,8aS,9R,10S, 12R, 12aR)-3,12-Epoxy-12H-pyrano[4,3-j]-1,2-benzo dioxe pin)). See Scheme 2 for examples. Pharmaceutically acceptable salts that may be included in embodiments herein can be found in Handbook of Pharmaceutical Salts: Properties, Selection, and Use, Stahl and Wermuth (Eds.), VHCA, Verlag Helvetica Chimica Acta (Zurich, Switzerland) and WILEY-VCH (Weinheim, Federal Republic of Germany); ISBN: 3-906390-26-8, which is incorporated herein by reference as if fully set forth. The pharmaceutically acceptable salts may or include at least one of the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, mandelate, mesylate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate, triethiodide, and trifluoroacetate salts. The pharmaceutically acceptable salts may or include salts of the compounds containing an acidic functional group that can be prepared by reacting with a suitable base. The pharmaceutically acceptable salts may be or include alkali metal salts (especially sodium and potassium), alkaline earth metal salt (especially calcium and magnesium), aluminum salts and ammonium salts, salts made from physiologically acceptable organic bases including trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N'-bisdehydroabietylamine, glucamine, N-methylglucamine, collidine, quinine, quinoline, and basic amino acids, lysine and arginine.

A composition herein may comprise a pharmaceutically acceptable carrier, which may be selected from but is not limited to one or more in the following list: ion exchangers, alumina, aluminum stearate, lecithin, serum proteins, human serum albumin, buffer substances, phosphates, glycine, sorbic acid, potassium sorbate, partial glyceride mixtures of saturated vegetable fatty acids, water, salts or electrolytes, protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, waxes, polyethylene glycol, starch, lactose, dicalcium phosphate, microcrystalline cellulose, sucrose, talc, magnesium carbonate, kaolin, non-ionic surfactants, edible oils, physiological saline, bacteriostatic water, Cremophor ELTM (BASF, Parsippany, N.J.) and phosphate buffered saline (PBS). The $^{18}$F radioactively labeled drug molecules created by methods herein may have nearly the same steric size as the parent drug.

In an embodiment, the $^{18}$F-labeled drugs may be used as PET imaging agents. The $^{18}$F-drug molecules disclosed herein are inhibitors of certain biological targets, and may be used as PET imaging agents. Ibuprofen, nabumetone and celecoxib are inhibitors of COX-2, which is a major contributor to the inflammatory response and cancer progression. The $^{18}$F-ibuprofe, $^{18}$F-Nabumetone, $^{18}$F-celecoxib analog may be used as PET imaging agents. It has been reported that the $^{18}$F-labeled COX-2 inhibitors can be useful probe for early detection of cancer and for evaluation of the COX-2 status of premalignant and malignant tumors. Examples of compounds in compositions herein follow.

An embodiment comprises a method of visualization. The method may comprise radioactively labeling a compound containing a carboxylic group by a method herein to create an imaging agent, administering the imaging agent to a patient and performing positron emission tomography on the patient. The patient may be an animal. The patient may be human. The step of the radioactive labeling may include at least one of separating the radioactively labeled compound from non-labeled compounds by HPLC and purifying the separated radioactively labeled compound by a cartridge. Purifying by a cartridge may comprise diluting a crude reaction mixture with a solvent that contains the radioactively labeled compound and one or more contaminants, passing the crude reaction mixture through the cartridge and eluting the radiolabeled compound with a solvent. The solvent may be water or any suitable organic solvent. The method may comprise adding the purified radioactively labeled compound to a saline solution prior to administering the imaging agent to a subject. Administering may be by injection. A dose of 200 µCi of $^{18}$F per mouse may be used in animal experiments. The skilled artisan would understand scaling of this amount to other patient species.

EMBODIMENTS

The following list includes particular embodiments of the present invention. The list, however, is not limiting and does not exclude alternate embodiments, as otherwise described herein or as would be appreciated by one of ordinary skill in the art.

1. A method of targeted fluorination of a compound containing a carboxyl group, the method comprising combining the compound, a nucleophilic fluoride source, a manganese catalyst, a solvent and an iodine (III) oxidant.

2. The method of embodiment 1, wherein the manganese catalyst is a manganese porphyrin or a manganese salen.

3. The method of any one or both embodiments 1 or 2, wherein the manganese porphyrin in a manganese(III) porphyrin.

4. The method of any one or more of the preceding embodiments, wherein the manganese(III) porphyrin is selected from the group consisting of: Mn(TMP)Cl, Mn(TTP) and Mn(TDCPP)Cl.

5. The method of anyone or more of the preceding embodiments, wherein the nucleophilic fluoride source comprises trialkyl amine trihydrofluoride.

6. The method of any one or more of the preceding embodiments, wherein the nucleophilic fluorides source is triethylamine trihydrofluoride.

7. The method of any one or more of the preceding embodiments, wherein combining comprises: mixing the manganese catalyst, the nucleophilic fluoride source, the compound and the solvent under an inert atmosphere to form a first mixture; and adding the iodine (III) oxidant to the first mixture to form a second mixture.

8. The method of embodiment 7 further comprising maintaining the first mixture at a temperature from 25° C. to 80° C.

9. The method of embodiment 8, wherein the temperature is 45° C.

10. The method of any one or more of the preceding embodiments, wherein the step of adding the oxidant occurs over a period of 45 minutes to 90 minutes.

11. The method of any one or more of embodiments 7-9, wherein combining further comprises adding benzoic acid.

12. The method of any one or more of the preceding embodiments, wherein the solvent is selected from the group consisting of: acetonitrile, dichloromethane, and 1,2-dichloroethane.

13. The method of any one or more of the preceding embodiments, wherein the iodine (III) oxidant is at least one of iodosylbenzene, iodobenzene, iodobenzene diacetate, dichloroiodobenzene, Bis(tert-butylcarbonyloxy)iodobenzene, iodosyl mesitylene, [Bis(trifluoroacetoxy)iodo]benzene, [Hydroxy(tosyloxy) iodo]benzene, iodomesitylene diacetate, iodosylpentafluorobenzene, [Bis(trifluoroacetoxy)iodo]pentafluorobenzene, 3,3-dimethyl-1-fluoro-1,2-benziodoxole, or (2-tert-butylsulfonyl) iodobenzene.

14. The method of any one or more of the preceding embodiments, wherein the compound is selected from the group consisting of: 2-(4-isobutylphenyl) propanoic acid; 2-(naphthalen-1-yloxy)acetic acid; 2,3-dihydrobenzo[b][1,4]dioxine-2-carboxylic acid; 2-(3-benzoylphenyl) propanoic acid; 2-(1,3-dioxoisoindolin-2-yl)-2-phenylacetic acid; 2-cyclopentyl-2-phenylacetic acid; 2-(naphthalen-1-yl)pent-4-y noic acid; 4-cyano-2-phenylbutanoic acid; 2-(4-(1-oxoisoindolin-2-yl)phenyl)propanoic acid; 2-(4-(bromomethyl)phenyl)propanoic acid; 2-(4-(allyloxy)phenoxy) acetic acid; 2-(4-(benzyloxy)phenyl)acetic acid; 2-(4-(5-(trifluoromethyl) pyridin-2-yloxy) phenoxy)propanoic acid; 2-(2,4-dichlorophenoxy) propanoic acid; 2-(naphthalen-2-yloxy)acetic acid; 2,3-diphenylpropanoic acid; 2-(1,3-dioxoisoindolin-2-yl)-3-phenyl propanoic acid; 2-phenyl butanoic acid; 12-(biphenyl-4-yl)acetic acid; 2,2-bis(4-chlorophenyl) acetic acid; 4-phenyl-2-(thiophen-3-yl)butanoic acid; 1-adamantane carboxylic acid; 23a: 3-phenylpropanoic acid; 2-methyl-3-phenylpropanoic acid; 2,2-dicyclohexylacetic acid; (E)-2-(cinnamoyloxy)-2-phenylacetic acid; 2-((8R,9S,13S,14S)-13-methyl-17-oxo-7,8,9,11,12,13,14,15,16,17-decahydro-6H-cyclopenta[α]phe-nanthren-3-yloxy)propanoic acid; and 2-[4-[[(3R,5aS,6R,8aS,9R,10S,12R,12aR)-de-cahydro-3,6,9-trimethyl-3,12-epoxy-12H-pyrano[4,3-j]-1,2-benzodioxepin-10-yl]oxy]phenoxy] propanoic acid.

15. A composition comprising a fluorinated product produced by the method of any one or more of the preceding embodiments.

16. A composition comprising a fluorinated product that includes at least one compound selected from the group consisting of:

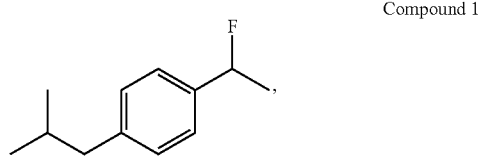
Compound 1

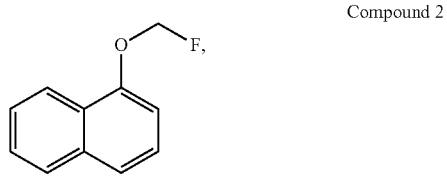
Compound 2

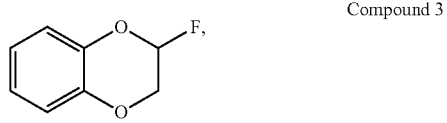
Compound 3

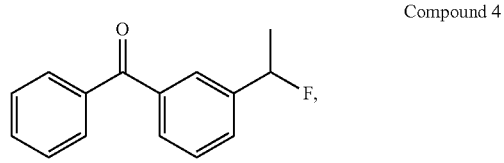
Compound 4

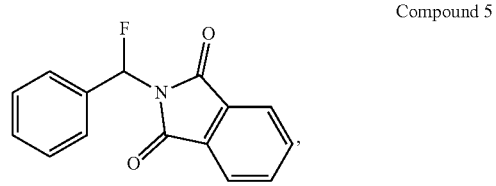
Compound 5

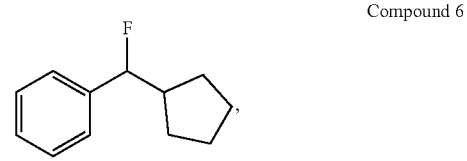
Compound 6

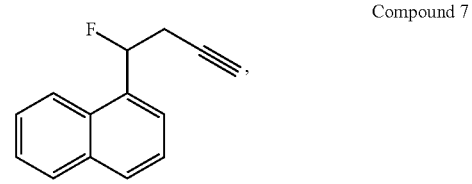
Compound 7

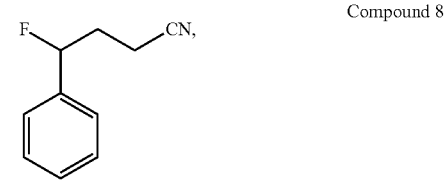
Compound 8

Compound 9
Compound 10
Compound 11
Compound 12
Compound 13
Compound 14
Compound 15
Compound 16
Compound 17
Compound 18
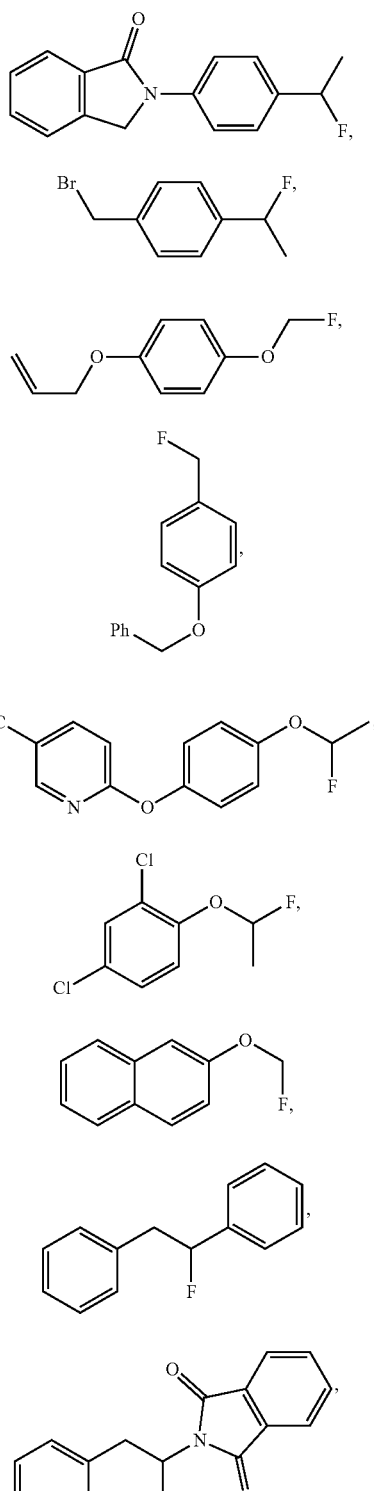
Compound 19
Compound 20
Compound 21
Compound 22
Compound 23
Compound 24
Compound 25
Compound 26
Compound 27
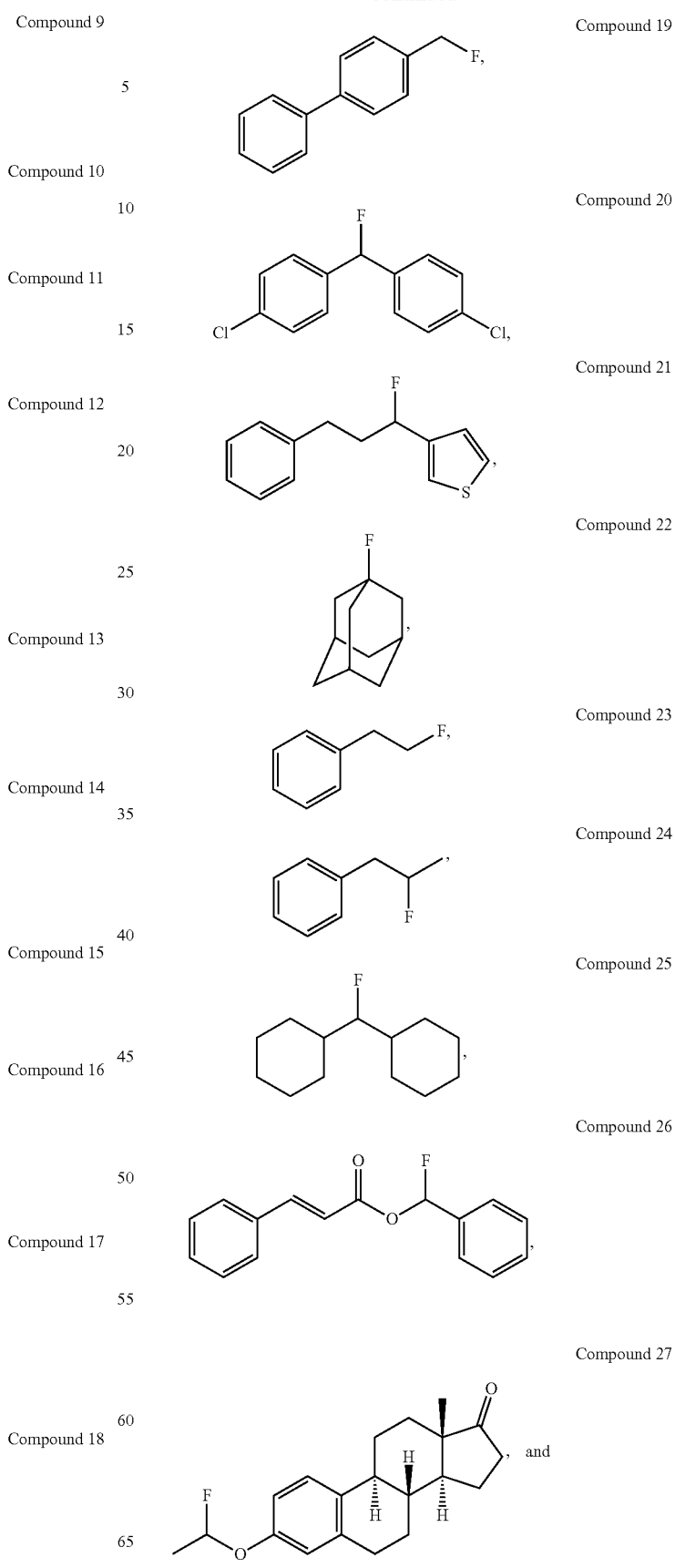
and -continued Compound 28

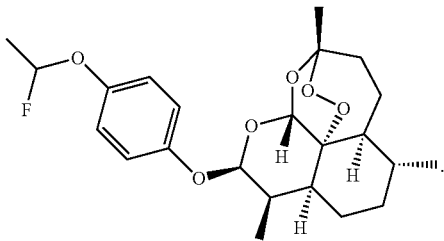

17. A method of direct radioactive labeling of a compound containing a carboxyl group, the method comprising combining the compound, a nucleophilic, radioactive fluoride source, a manganese catalyst, a solvent and an iodine (III) oxidant.

18. The method of embodiment 17, wherein the manganese catalyst is manganese porphyrin or a manganese salen.

19. The method of one or both of embodiments 17 or 18, wherein the manganese catalyst is a manganese(III) porphyrin.

20. The method of any one or more of embodiments 18-19, wherein the manganese(III) porphyrin is selected from the group consisting of: Mn(TMP)Cl, Mn(TTP) and Mn(TDCPP)Cl.

21. The method of any one or more of embodiments 17-20, wherein the nucleophilic radioactive fluoride source is [$^{18}$F]-fluoride.

22. The method of any one or more of embodiments 17-21, wherein the step of combining includes mixing the compound and the iodine(III) oxidant to form a first mixture, mixing the nucleophilic radioactive fluoride source and the solvent to form the second mixture, and mixing the first mixture and the second mixture to form the third mixture, and adding the manganese catalyst to the third mixture, and combining is performed under air.

23. The method of embodiment 21, wherein the reaction time is from 2 minutes to 30 minutes 24. The method of embodiment 22 further comprising reacting the compound, the nucleophilic radioactive fluoride source, the solvent, and the iodine (III) oxidant for 5 minutes to 30 minutes after the step of adding manganese catalyst.

25. The method of any one or more of embodiments 21-24 further comprising maintaining the compound, the iodine (III) oxidant, the fluorine radioisotope, the solvent and the manganese catalyst at a temperature of 25° C. to 100° C.

26. The method of any one or more of embodiments 17-25, wherein prior to the step of combining, the method further comprises obtaining an aqueous [$^{18}$F]fluoride solution from a cyclotron, loading the aqueous [$^{18}$F] fluoride solution onto an ion exchange cartridge and releasing the [$^{18}$F] fluoride from the ion exchange cartridge with an acetonitrile or alkaline solution. The alkaline solution may comprise $K_2CO_3$.

27. The method of embodiments 26, wherein the solution comprises a manganese catalyst.

28. The method of one or more of embodiments 26-27, wherein the [$^{18}$F]fluoride is mixed with acetonitrile to form a [$^{18}$F] fluoride acetonitrile solution.

29. The method of any one or more of embodiments 26-28, wherein the ion exchange cartridge is an anion exchange cartridge.

30. The method of any one or more of embodiments 17-29, wherein the solvent is acetonitrile or acetone.

31. The method of any one or more of embodiments 17-30, wherein the iodine (III) oxidant is at least one of iodosylbenzene, iodobenzene, iodobenzene diacetate, dichloroiodobenzene, Bis(tert-butylcarbonyloxy)iodobenzene, iodosyl mesitylene, [Bis(trifluoroacetoxy)iodo]benzene, [Hydroxy(tosyloxy) iodo]benzene, iodomesitylene diacetate, iodosylpentafluorobenzene, [Bis(trifluoroacetoxy)iodo]pentafluorobenzene, 3,3-dimethyl-1-fluoro-1,2-benziodoxole, or (2-tert-butylsulfonyl) iodobenzene.

32. The method of any one or more of embodiments 17-31, wherein compound is selected from the group consisting of: 2-(4-isobutylphenyl) propanoic acid; 2-(naphthalen-1-yloxy)acetic acid; 2,3-dihydrobenzo[b] [1,4]dioxine-2-carboxylic acid; 2-(3-benzoylphenyl)propanoic acid; 2-(1, 3-dioxoisoindolin-2-yl)-2-phenylacetic acid; 2-cyclopentyl-2-phenylacetic acid; 2-(naphthalen-1-yl)pent-4-ynoic acid; 4-cyano-2-phenylbutanoic acid; 2-(4-(1-oxoisoindolin-2-yl) phenyl)propanoic acid; 2-(4-(bromomethyl) phenyl)propanoic acid; 2-(4-(allyloxy)phenoxy)acetic acid; 2-(4-(benzyloxy)phenyl)acetic acid; 2-(4-(5-(trifluoromethyl)pyridin-2-yloxy)phenoxy) propanoic acid; 2-(2,4-dichlorophenoxy) propanoic acid; 2-(naphthalen-2-yloxy)acetic acid; 2,3-diphenylpropanoic acid; 2-(1,3-dioxoisoindolin-2-yl)-3-phenylpropanoic acid; 2-phenylbutanoic acid; 12-(biphenyl-4-yl) acetic acid; 2,2-bis(4-chlorophenyl) acetic acid; 4-phenyl-2-(thiophen-3-yl)butanoic acid; 1-adamantanecarboxylic acid; 23a: 3-phenylpropanoic acid; 2-methyl-3-phenylpropanoic acid; 2,2-dicyclo hexylacetic acid; (E)-2-(cinnamoyloxy)-2-phenylacetic acid; 2-((8R,9S,13S,14S)-13-methyl-17-oxo-7,8,9,11,12,13,14,15,16,17-decahydro-6H-cyclopenta[a]phenanthren-3-yloxy)propanoic acid; and 2-[4-[[(3R,5aS,6R,8aS,9R,10S,12R, 12aR)-decahydro-3,6, 9-trimethyl-3,12-epoxy-12H-pyrano[4,3-j]-1,2-benzodioxepin-10-yl]oxy]phenoxy]propanoic acid.

33. A composition comprising at least one radio-labeled product produced by the method of any one or more of embodiments 17-32 and 35-36.

34. A composition comprising a radio-labeled compound selected from the group consisting of:

Compound $^{18}$F-1

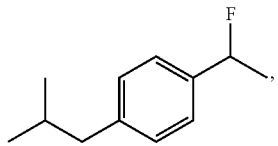

Compound $^{18}$F-2

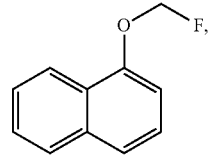

Compound $^{18}$F-3

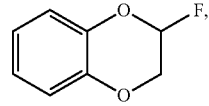

Compound $^{18}$F-4

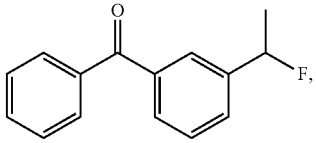

-continued

Compound $^{18}$F-5

Compound $^{18}$F-6

Compound $^{18}$F-7

Compound $^{18}$F-8

Compound $^{18}$F-9

Compound $^{18}$F-10

Compound $^{18}$F-11

Compound $^{18}$F-12

Compound $^{18}$F-13

-continued

Compound $^{18}$F-14

Compound $^{18}$F-15

Compound $^{18}$F-16

Compound $^{18}$F-17

Compound $^{18}$F-18

Compound $^{18}$F-19

Compound $^{18}$F-20

Compound $^{18}$F-21

Compound $^{18}$F-22

Compound $^{18}$F-23

-continued

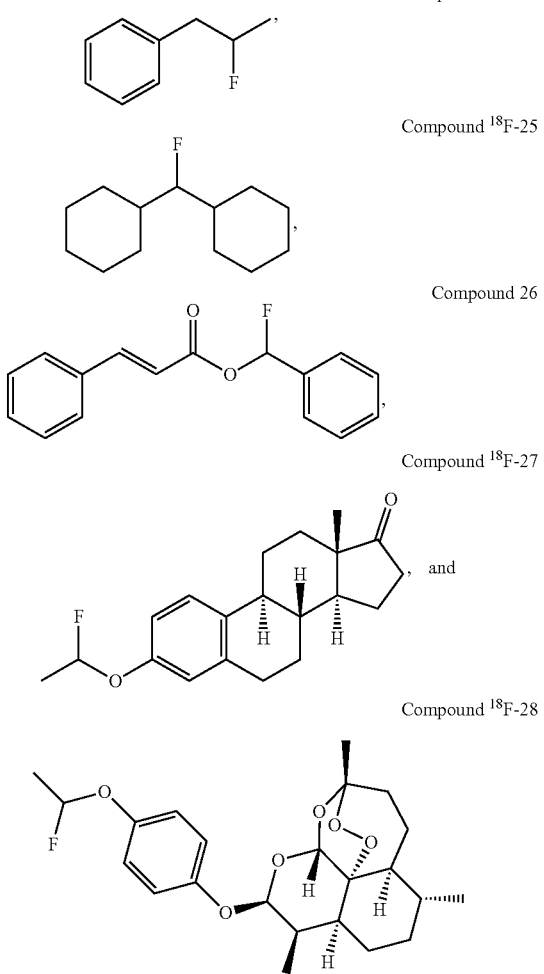

wherein the F in compounds 1-28 is $^{18}$F.

35. The method of any one of embodiments 17-32, wherein the reaction is conducted under an anaerobic or inert atmosphere.

36. The method of any one of embodiments 17-32, wherein the reaction is conducted under atmospheric air.

37. A method of targeted fluorination comprising combining a mono-fluoro-aryl iodine-(III) carboxylate and a manganese catalyst.

38. The method of embodiment 37, wherein the manganese catalyst is a manganese porphyrin or a manganese salen.

39. The method of any one of embodiments 37-38, wherein the manganese porphyrin is a manganese(III) porphyrin.

40. The method of any one of embodiments 37-39, wherein the manganese(III) porphyrin is selected from the group consisting of: Mn(TMP)Cl, Mn(TTP) and Mn(TDCPP)Cl.

41. The method of any one of embodiments 37-40 further comprising mixing a compound containing a carboxyl group, a nucleophilic fluoride source, a solvent and an iodine (III) oxidant to form the mono-fluoro-aryl iodine-(III) carboxylate prior to the step of combining.

42. The method of embodiment 40, wherein the solvent is selected from the group consisting of: acetonitrile, acetone, dichloromethane, and 1,2-dichloroethane.

43. The method of any one of embodiments 41-42, wherein the iodine(III) oxidant is iodosylbenzene, iodobenzene, iodobenzene diacetate, dichloroiodobenzene, Bis(tert-butylcarbonyloxy)iodobenzene, iodosylmesitylene, [Bis(trifluoroacetoxy) iodo]benzene, [Hydroxy(tosyloxy)iodo] benzene, iodomesitylene diacetate, iodosyl pentafluorobenzene, [Bis (trifluoroacetoxy)iodo]pentafluorobenzene, 3,3-dimethyl-1-fluoro-1,2-benziodoxole, or (2-tert-butylsulfonyl)iodobenzene.

44. The method of any one of embodiments 41-43, wherein the compound is selected from the group consisting of: 2-(4-isobutyl phenyl)propanoic acid; 2-(naphthalen-1-yloxy)acetic acid; 2,3-dihydro benzo[b] [1,4]dioxine-2-carboxylic acid; 2-(3-benzoylphenyl)propanoic acid; 2-(1,3-dioxoisoindolin-2-yl)-2-phenylacetic acid; 2-cyclopentyl-2-phenyl acetic acid; 2-(naphthalen-1-yl)pent-4-ynoic acid; 4-cyano-2-phenyl butanoic acid; 2-(4-(1-oxoisoindolin-2-yl)phenyl)propanoic acid; 2-(4-(bromomethyl)phenyl)propanoic acid; 2-(4-(allyloxy)phenoxy)acetic acid; 2-(4-(benzyloxy)phenyl)acetic acid; 2-(4-(5-(trifluoromethyl)pyridin-2-yloxy)phenoxy) propanoic acid; 2-(2,4-dichlorophenoxy) propanoic acid; 2-(naphthalen-2-yloxy)acetic acid; 2,3-diphenylpropanoic acid; 2-(1,3-dioxoisoindolin-2-yl)-3-phenylpropanoic acid; 2-phenylbutanoic acid; 12-(biphenyl-4-yl) acetic acid; 2,2-bis(4-chlorophenyl) acetic acid; 4-phenyl-2-(thiophen-3-yl)butanoic acid; 1-adamantanecarboxylic acid; 23a: 3-phenylpropanoic acid; 2-methyl-3-phenylpropanoic acid; 2,2-dicyclo hexylacetic acid; (E)-2-(cinnamoyloxy)-2-phenylacetic acid; 2-((8R,9S,13S,14S)-13-methyl-17-oxo-7,8,9,11,12,13,14,15,16,17-decahydro-6H-cyclopenta[α]phenanthren-3-yloxy)propanoic acid; and 2-[4-[[(3R,5aS,6R,8aS,9R,10S,12R, 12aR)-decahydro-3,6,9-trimethyl-3,12-epoxy-12H-pyrano[4,3-j]-1,2-benzodioxepin-10-yl]oxy]phenoxy]propanoic acid.

45. The method of any one of embodiments 41-44 further comprising maintaining the mono-fluoro-aryl iodine-(III) carboxylate at a temperature from 25° C. to 80° C.

46. The method of any one of embodiments 41-46, wherein the nucleophilic fluoride source is trialkyl amine trihydrofluoride.

47. The method embodiment 46, wherein the trialkyl amine trihydrofluoride is triethylamine trihydrofluoride.

48. The method of embodiment 37, wherein the step of combining is performed under an inert atmosphere.

49. The method of any one of embodiments 41-45, wherein the nucleophilic fluoride source is [$^{18}$F]-fluoride.

50. The method of any one of embodiments 41-5 and 49, wherein prior to the step of mixing obtaining an aqueous [$^{18}$F] fluoride solution from a cyclotron, loading the aqueous [$^{18}$F] fluoride solution onto an ion exchange cartridge and releasing the [$^{18}$F] fluoride from the ion exchange cartridge with an alkaline solution.

51. The method of embodiment 50, wherein the [$^{18}$F] fluoride is mixed with acetonitrile to form the [$^{18}$F] fluoride acetonitrile solution.

52. The method of embodiment 50, wherein the ion exchange cartridge is an anion exchange cartridge.

53. A method of visualization comprising: radioactively labeling a compound containing a carboxylic group by the method of any one or more of embodiments 17-32, 37 45 and 49-52, where the fluorine radioisotope includes $^{18}$F and a product produced by the method is an 18F imaging agent; admninistering the imaging agent to a patient and performing positron emission tomography on the patient.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1—Manganese Catalyzed Decarboxylative Fluorination and Optimization of the Reaction Conditions Scheme 1 illustrates the concept of manganese catalyzed decarboxylation in comparison to previously reported decarboxylative hydroxylation [22] and aliphatic C—H fluorination [14]. Scheme 1(a) illustrates decarboxylative hydroxylation [22]. Scheme 1(b) illustrates aliphatic C—H fluorination [14]. Referring to this scheme, the reaction employed manganese tetramesitylporphyrin, Mn(TMP)Cl, as the catalyst and silver fluoride/tetrabutylammonium fluoride trihydrate (TBAF.3H₂O) as the fluoride source and proceed through a trans-difluoromanganese(IV) porphyrin complex that served as the fluorine transfer agent.

Scheme 1. Manganese-catalyzed decarboxylative fluorination versus decarboxylative hydroxylation and aliphatic C-H fluorination.

a) Decarboxylative hydroxylation (Ref. 22)

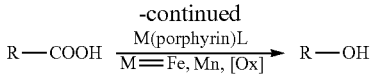

b) Aliphatic C-H fluorination (Ref. 14)

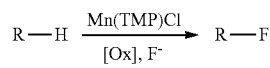

c) Decarboxylative fluorination

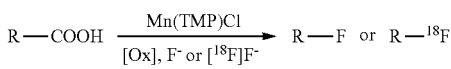

Scheme 1(c) illustrates decarboxylative fluorination using fluoride ion and Mn(TMP)Cl as the catalyst.

Surprisingly, decarboxylative fluorination was achieved over the previously observed hydroxylation by use of an appropriate fluoride source which unexpectedly redirected the usual oxygenation scenario to fluorination. Table 1 shows optimization of decarboxylative fluorination of ibuprophen as an initial model substrate. Exploratory reaction conditions for fluorination afforded fluorination product 1 in a promising 13% yield (Table 1, entry 1). A less basic fluoride source, triethylamine trihydrofluoride (Et₃N.3HF) was utilized,[20] with which the yield increased to 53% (Table 1, entry 2). Other solvents, catalysts and oxidants were tested. The best yield of 61% was obtained with Mn(TMP)Cl as the catalyst, iodosylbenzene (PhIO) as the oxidant and 1,2-dichloroethane (DCE) as solvent (Table 1, entry 3). Further experimentation surprisingly revealed that adding 0.5 equiv. benzoic acid could further increase the yield to 65% (Table 1, entry 9) with a fluorination/oxygenation selectivity of 9:1.

TABLE 1

Reaction conditions [a]

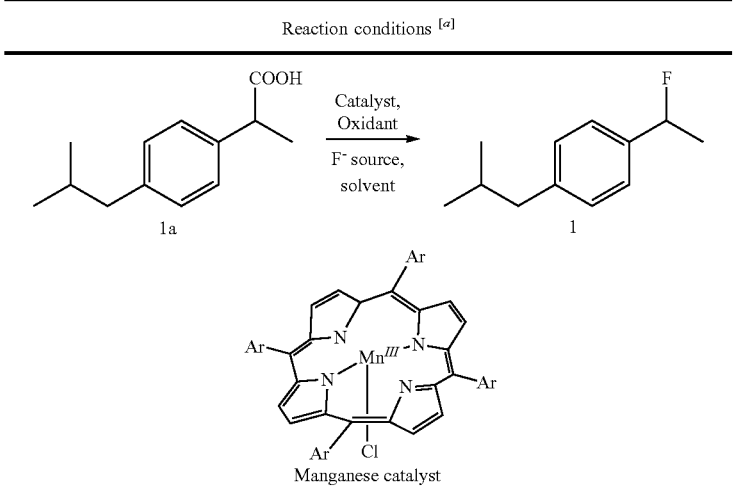

| Entry | Catalyst | Oxidant | F⁻(equiv.) | Solvent | Yield[b] |
|---|---|---|---|---|---|
| 1 | Mn(TMP)Cl | PhIO | AgF/TBAF · 3H₂O | ACN/DCM | 13% |
| 2 | Mn(TMP)Cl | PhIO | Et₃N · 3HF (1.2) | ACN/DCM | 53% |
| 3 | Mn(TMP)Cl | PhIO | Et₃N · 3HF (1.2) | DCE | 61% |
| 4 | Mn(TTP)Cl | PhIO | Et₃N · 3HF (1.2) | DCE | 43% |
| 5 | Mn(TDCPP)Cl | PhIO | Et₃N · 3HF (1.2) | DCE | 16% |
| 6 | Mn(TPFPP)Cl | PhIO | Et₃N · 3HF (1.2) | DCE | trace |
| 7 | Mn(TMP)Cl | PhI(OPiv)₂ | Et₃N · 3HF (1.2) | DCE | 45% |
| 8 | Mn(TMP)Cl | PhI(OAc)₂ | Et₃N · 3HF (1.2) | DCE | 50% |
| 9 | Mn(TMP)Cl | PhIO | Et₃N · 3HF (1.2) | DCE | 65%[b] |

TABLE 1-continued

Reaction conditions [a]

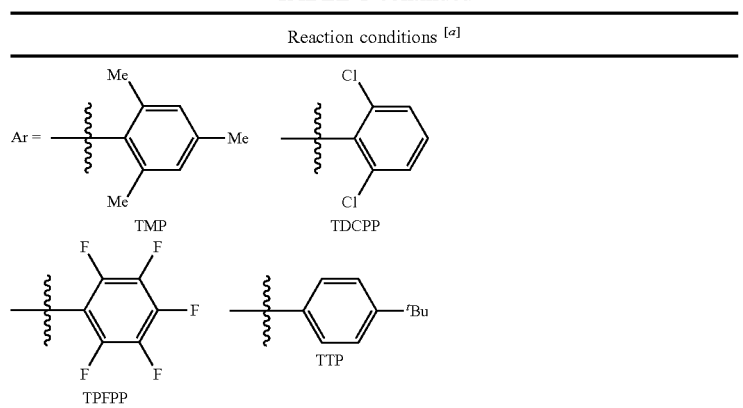

[a] Reaction conditions: Nitrogen atmosphere, 1a (103 mg, 0.5 mmol), catalyst (10 mg, 2.5 mol %), oxidant (370 mg, 3.3 equiv.) and solvent (1 mL). Yield was determined by $^{19}$F-NMR with 20 μL fluorobenzene as standard.
[b] 0.5 equiv. benzoic acid as additive.

The decarboxylative fluorination differs from Mn-catalyzed C—H fluorination and decarboxylative hydroxylation in the following aspects. Decarboxylative fluorination can be used to prepare fluoromethyl ethers and N-fluoroalkyls as described in Examples herein. These types of products were not observed in Mn-catalyzed C—H fluorination or decarboxylative hydroxylation reactions. Ether substrates are not reactive under Mn-catalyzed C—H fluorination reactions. In the manganese-catalyzed C—H $^{18}$F-fluorination reaction, the weak coordinating axial ligand is needed to achieve high radiolabeling yield. However, in the decarboxylative $^{18}$F radio-fluorination, a weak coordinating axial ligand is not needed. High radiochemical yields can be obtained with the usual Mn(TMP)Cl catalyst (i.e., with chloride ligand). This demonstrates that the decarboxylative fluorination and Mn-catalyzed C—H fluorination reactions are different. Additionally, the two reactions proceed through different mechanisms. In C—H fluorination, the C—H activation proceeds through a high-valent oxomanganese(V) intermediate, while in decarboxylative hydroxylation, hydroxylcarboxylatoiodinane species oxidize the manganese(III) to hydroxomanganese(IV) and generate carboxyl radical. For decarboxylative fluorination, there is no precedent that an analogous fluorocarboxylatoiodinane (iodine(III) species are also called iodinanes) species exist, and the one electron oxidation of manganese(III) to fluoromanganese(IV) is not known. Furthermore, the carboxylic acid could react with fluoride to form HF and silver salt used commonly in the C—H fluorination would form insoluble silver carboxylate with carboxylic acid, both scenarios will inhibit the reaction.

Example 2—Substrate Scope and Functional Group Tolerance

After the optimal conditions were identified, the substrate scope of this reaction was examined. As shown in Scheme 2, a variety of functional groups, including heterocycles, amide, imide, ester, ketone, ether, nitrile, halogen and even alkene and alkyne are well tolerated.

Scheme 2 illustrates the substrate scope and functional group tolerance in this reaction.

Scheme 2. Substrate scope and functional group tolerance

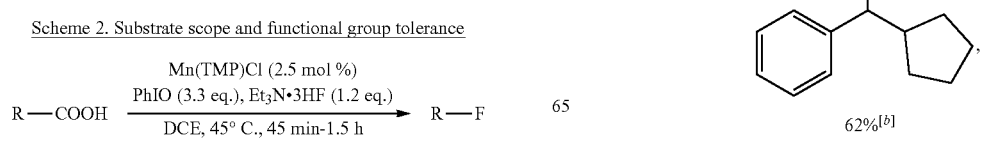

-continued

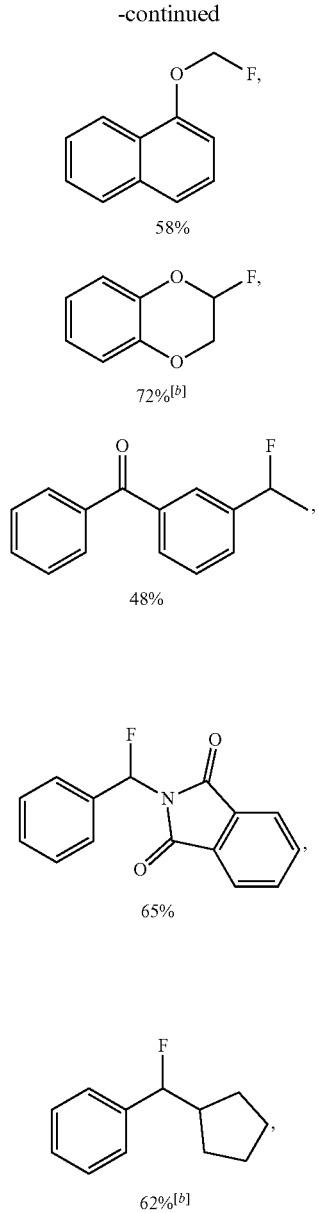

-continued
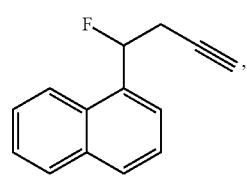
48%
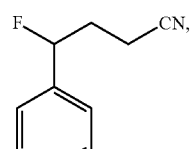
50%
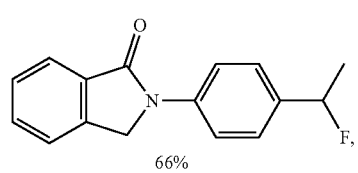
66%
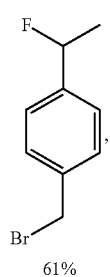
61%
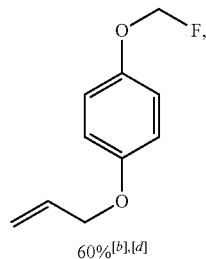
60%[b],[d]
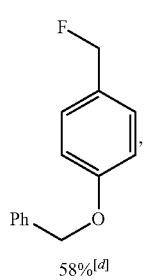
58%[d]
-continued
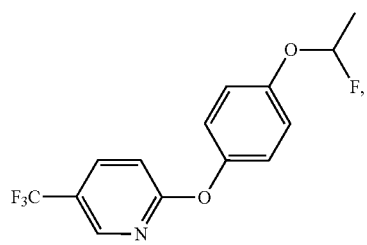
74%
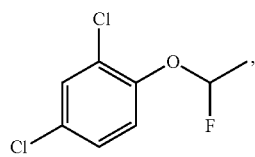
70%
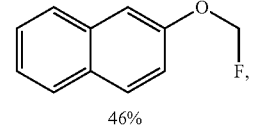
46%
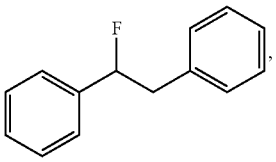
60%
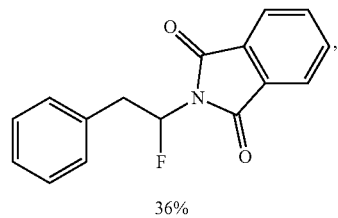
36%
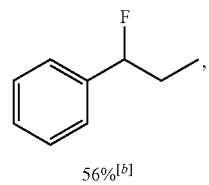
56%[b]
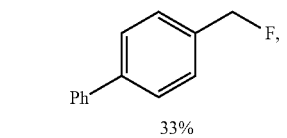
33%
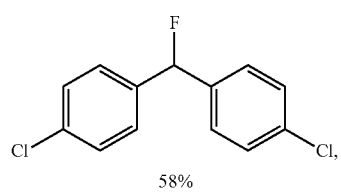
58%

-continued

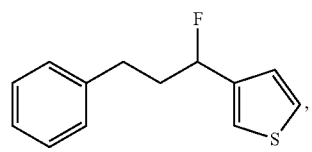

56%[c]

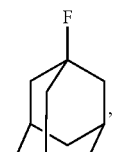

38%[b]

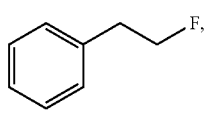

trace

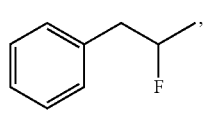

17%[b]

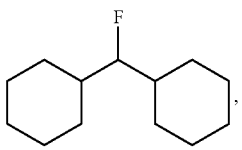

15%

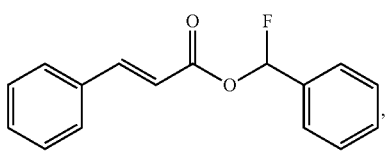

F-benzyl cinnamate
antifungal reagent
56%

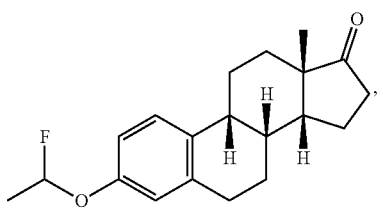

estrone derivative
45 min, 65%

-continued

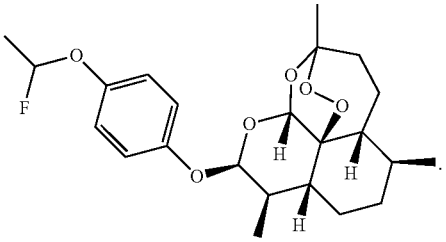

artemisinin derivative
1 h, 61%

[a] Standard conditions: Substrates (0.5 mmol), Mn(TMP)Cl (2.5 mol %), Et₃N•3HF (1.2 equiv.), benzoic acid additive (0.5 equiv.), DCE (1 mL). PhIO (3.3 equiv.) was added in small portions within 45 min to 1.5 h at 45° C. under N₂ protection. The reported yields were isolated yield unless otherwise noted. [b] Yields were determined by $^{19}$F-NMR. [c] Iodosylmesitylene was used as oxidant. [d] 2 equiv. of oxidants were used.

Higher yields were generally observed for substrates bearing electron-donating substituents. Molecules containing strongly electron-rich aromatic rings, which are challenging substrates for Selectfluor-based decarboxylative fluorination methods due to the competing aryl fluorination,[19c] were readily fluorinated without any ring fluorination (11-13).

The tolerance to reactive functional groups like halogens (10) and alkynes (7) further broaden the application of the present method, as various structural motifs can be accessed through these functionalities by well-established methods such as cross coupling or "click" reactions. Surprisingly, no epoxidation or C—H activation products were observed with substrates containing olefins (e.g. substrates 11 and 21), despite the well-known Mn(TMP)Cl/PhIO catalytic system that efficiently performs these reactions.[21]

While the present method efficiently fluorinated benzylic and aryloxy carboxylic acids, tertiary, secondary and primary acids were less reactive (22-25). The same trend was observed for the related Mn-catalyzed decarboxylative hydroxylation reaction.[22] The results suggest a free radical pathway, as the reactivity pattern is consistent with variations of the C—COOH bond dissociation energies.[23]

The mildness of the fluorination conditions prompted tests of the reaction for fluorinating molecules with structures of biological importance. The molecule tested was benzyl cinnamate, a common fragrance ingredient and antifungal reagent. The fluorinated benzyl cinnamate (26) could be obtained in 58% yield from the 2-(cinnamoyloxy)-2-phenylacetic acid with no epoxidation products being detected. Moreover, the fluorination product of an estrone derivative (27) could be obtained in 65% isolated yield within 45 min. The reported method could also be applied to fragile, complex structures like artemisinin. The decarboxylative fluorination of an artemisinin derivative went smoothly to afford 28 in 61% isolated yield in 1 h. These results clearly demonstrate the significant potential of the reported method for late-stage fluorination of bioactive molecules.

Example 3—Decarboxylative Fluorination with KF as a Fluoride Source

Compared to current decarboxylative fluorination methods that are based on F⁺ reagents, an advantage of this fluoride-based decarboxylative fluorination reaction is its applicability to $^{18}$F labelling with [$^{18}$F]fluoride. To demonstrate this potential, the reaction with limiting amounts of K[19]F as the sole fluoride source was tested, since a functional reaction for $^{18}$F labelling should be able to incorporate sub-stoichiometric amounts of fluoride into substrate molecules.[1f, 7d, 24]

Scheme 3. (a) Decarboxylative fluorination with KF as a fluoride source. (b) Adapting manganese-catalyzed decarboxylative fluorination to $^{18}$F labelling. Radiochemical conversions (RCCs) are averaged over (n) experiments.

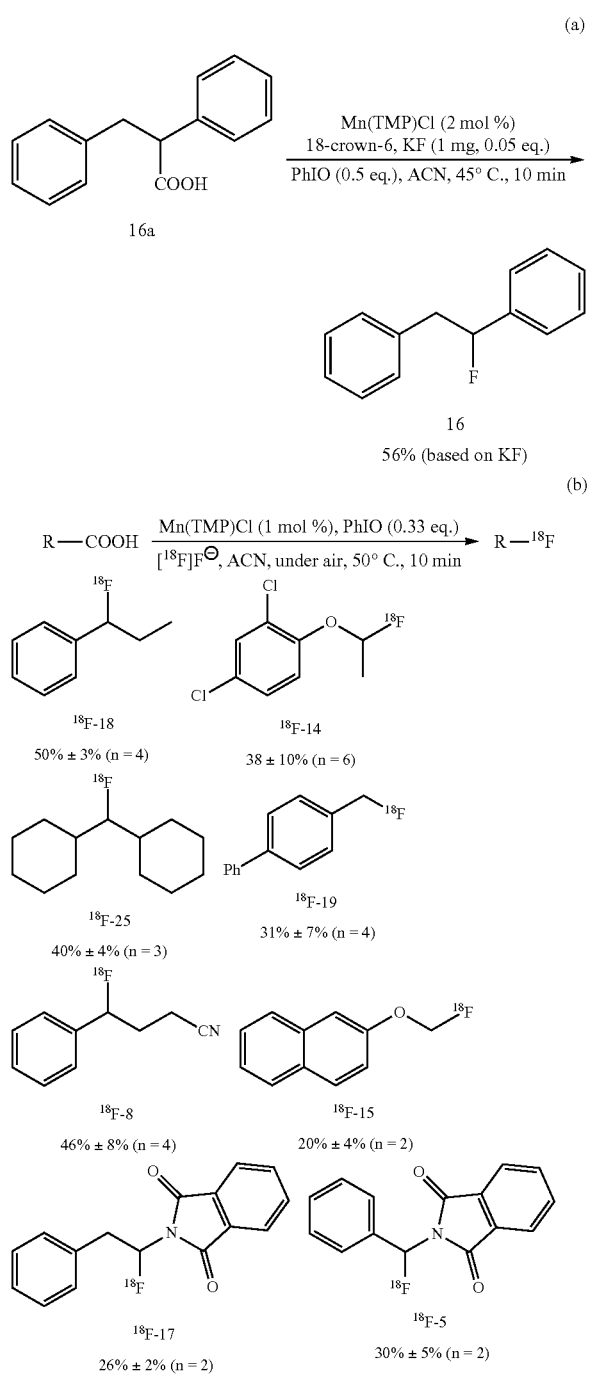

included the following condition: 16a, 83 mg (367.2 µmol, 21 equiv.), KF 1 mg (17.0 µmol, 1.0 equiv.) 18-crown-6, 16 mg (30.2 µmol, 1.8 equiv.) and 2 mL of ACN were added to a vial. PhIO 38 mg (172.7 µmol, 10 equiv.) were added to the solution. The mixture was stirred for 2 minutes at room temperature. Mn(TMP)Cl 6 mg (6.8 µmol, 0.4 equiv. 2 mol %) were added to the solution. Then the reaction mixture was stirred at 46° C. for 10 minutes. Scheme 3a illustrates that treating acid 16a with Mn(TMP)Cl, PhIO and only 0.05 equiv. of KF in acetonitrile for 10 min afforded the fluorinated product 16 (1-fluoroethane-1,2-diyl)dibenzene) in 56% yield based on the amount if fluoride. Scheme 3b illustrates the efficacy of this method for radiofluorination with no-carrier-added [$^{18}$F]fluoride was further evaluated. It was observed that carboxylic acids underwent efficient decarboxylative $^{18}$F-fluorination with RCCs ranging from 26% to 50% under similar reaction conditions to those used with K[19]F. Unlike $^{19}$F reaction conditions where anaerobic conditions were preferred, the $^{18}$F labelling reactions were carried out under air, greatly simplifying the labelling protocol. Less reactive acids under $^{19}$F conditions, such as secondary carboxylic acid 25a, could be readily $^{18}$F-labeled (40% RCC of [18]F-25) by using the same reaction conditions as here. This seemingly counterintuitive phenomenon was also observed in the manganese-catalyzed C—H $^{18}$F-fluorination reaction, and is presumably due to the very low concentration of [$^{18}$F]fluoride and the large excess of other reactants. It was demonstrated that the tedious azeotropic K[18]F drying step could be eliminated by directly eluting [$^{18}$F]fluoride from the ion exchange cartridge with a solution of the Mn(salen)OTs catalyst. With a similar protocol, [18]F-19 was obtained with 10% non-decay corrected RCY. The specific activity was determined to be 1.78 Ci/µmol (@EOB). This transformation represents the first general decarboxylative $^{18}$F labelling method with no-carrier-added [$^{18}$F]fluoride. The substrate scope of this $^{18}$F labelling method and adapt it to PET imaging applications can be expanded.

In addition, optimatization of the technique with $^{19}$F under conditions stoichiometric in fluoride ion is a good predictor of behavior when fluoride is the limiting reagent, such as it is during $^{18}$F methods. An example is supplied below. These conditions approximate those used during $^{18}$F labeling experiments. It was observed that the yield from $^{19}$F NMR (both GC-MS and NMR) is 56% based on fluoride as the limiting reagent. Surprisingly, this yield is 5-fold higher than the C—H fluorination under similar conditions, indicating that $^{18}$F incorporation will also be much more efficient.

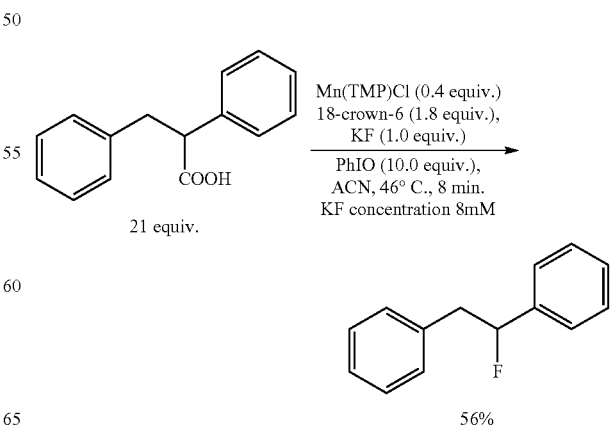

Scheme 3a illustrates decarboxiative fluorination of acid 16a (2,3-diphenylpropanoic acid). An experimental reaction An experimental reaction included the following condition: KF 2 mg (34.5 μmol, 1 equiv.), 18-crown-6 16 mg (60.53 μmol, 1.8 equiv.) and 4 mL of dry ACN were added to a vial. The obtained solution was sonicated for 2 min. 2,3-diphenylpropionic acid 166 mg (734.5 μmol, 21 equiv.) and PhIO 76 mg (345.5 μmol, 10 equiv.) were added to the solution. The mixture was stirred for 2 minutes at room temperature to allow production of the iodine(III) decarboxylate. Then Mn(TMP)Cl 12 mg (13.7 μmol, 0.4 equiv.) were added to the solution. Then the reaction mixture was stirred at 46° C. for 8 minutes. After cooling to room temperature, the solvent was evaporated and 10 μL fluorobenzene was added as internal standard. The yield was determined by $^{19}$F NMR. 56% yield was obtained. The reaction was performed under air to mimic the $^{18}$F labeling conditions. The difference with of the decarboxylative fluorination performed under air and under an inert atmosphere is the amount of reagents to be used. The labeling conditions use much lower amount of reagents and less solvent. Also, in the dry-down free protocol described herein for $^{18}$F labeling, iodine(III) dicarboxylate was used as both the substrate and the oxidant.

Example 4—Mechanism of Decarboxilative Fluorination

A proposed reaction mechanism for this R—COOH to R—F conversion is illustrated in FIG. 1. As shown in FIG. 1, there are two likely pathways for the activation of the carboxylic acid. The first involves the pre-formation of an iodine(III) carboxylate ester via reaction of iodosylbenzene with the carboxylic acid substrate that oxidizes the manganese(III) porphyrin to fluoromanganese(IV) intermediate with concurrent decarboxylation (pathway A). The second pathway proceeds through a direct hydrogen abstraction from the carboxylic acid O—H by an oxomanganese(V) porphyrin intermediate (pathway B). Although further work is needed to differentiate the two pathways, current evidence suggests pathway A, since both PhI(OPiv)$_2$ and PhI(OAc)$_2$ were efficient oxidants for decarboxylative fluorination in the absence of water (Table 1, entries 7 and 8).

Moreover, mCPBA, an efficient oxygen transfer agent that converts manganese porphyrins to oxomanganese(V), was a less efficient reagent for decarboxylative fluorination. For example, the yield of (1-fluoropropyl)benzene (18) dropped from 56% to 13% upon changing the oxidant from PhIO to mCPBA.

Figure 2A:
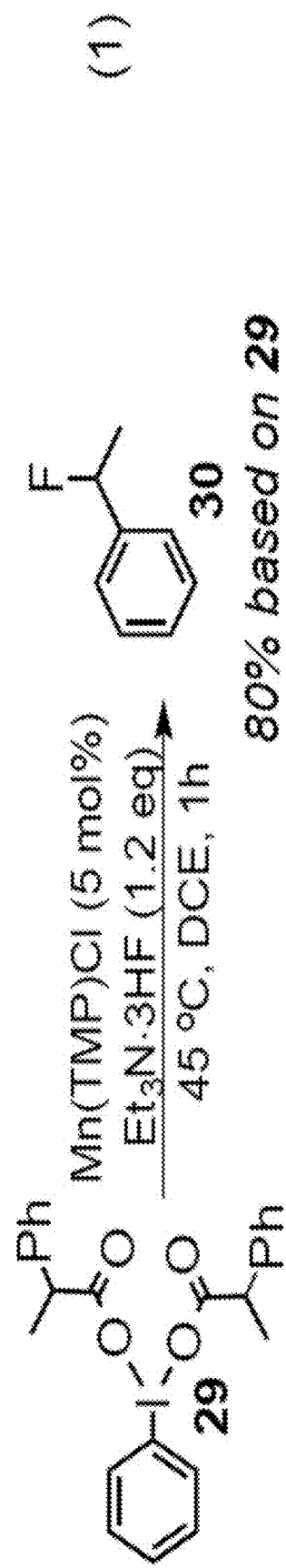
FIGS. 2A-2C illustrate a scheme of fluorination of iodine (III) decarboxylate.
Figure 2B:
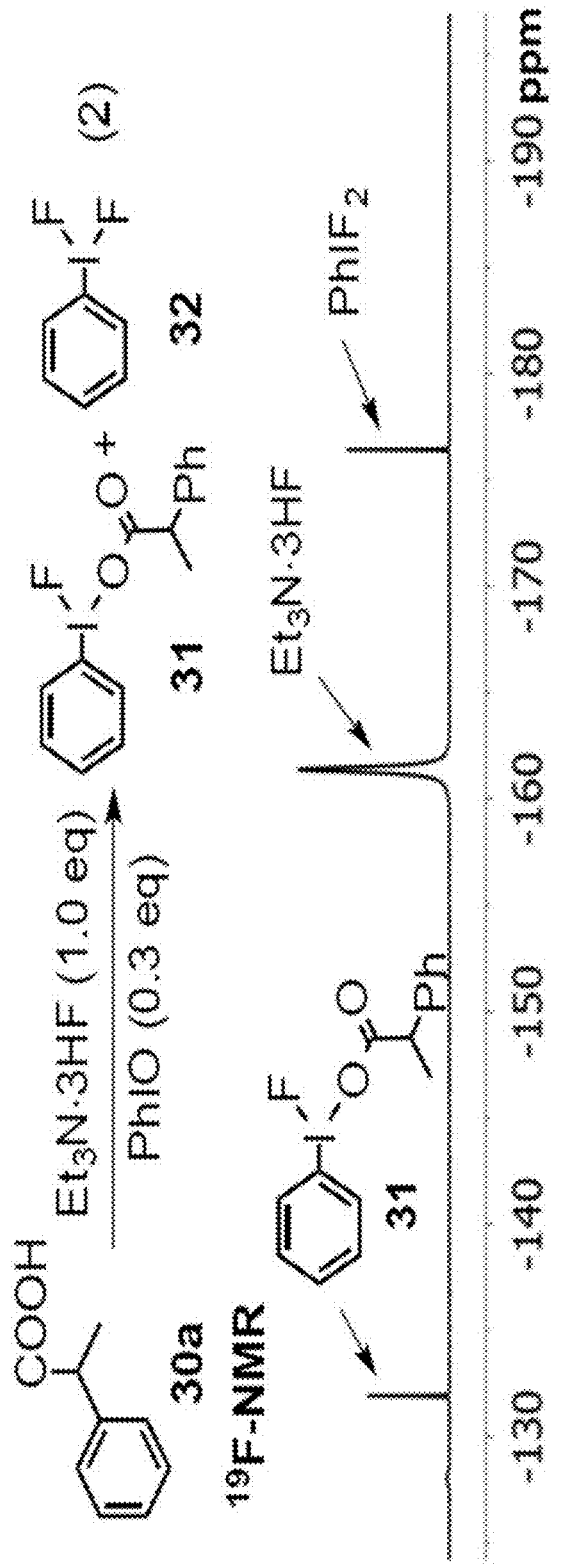
Figure 2C:
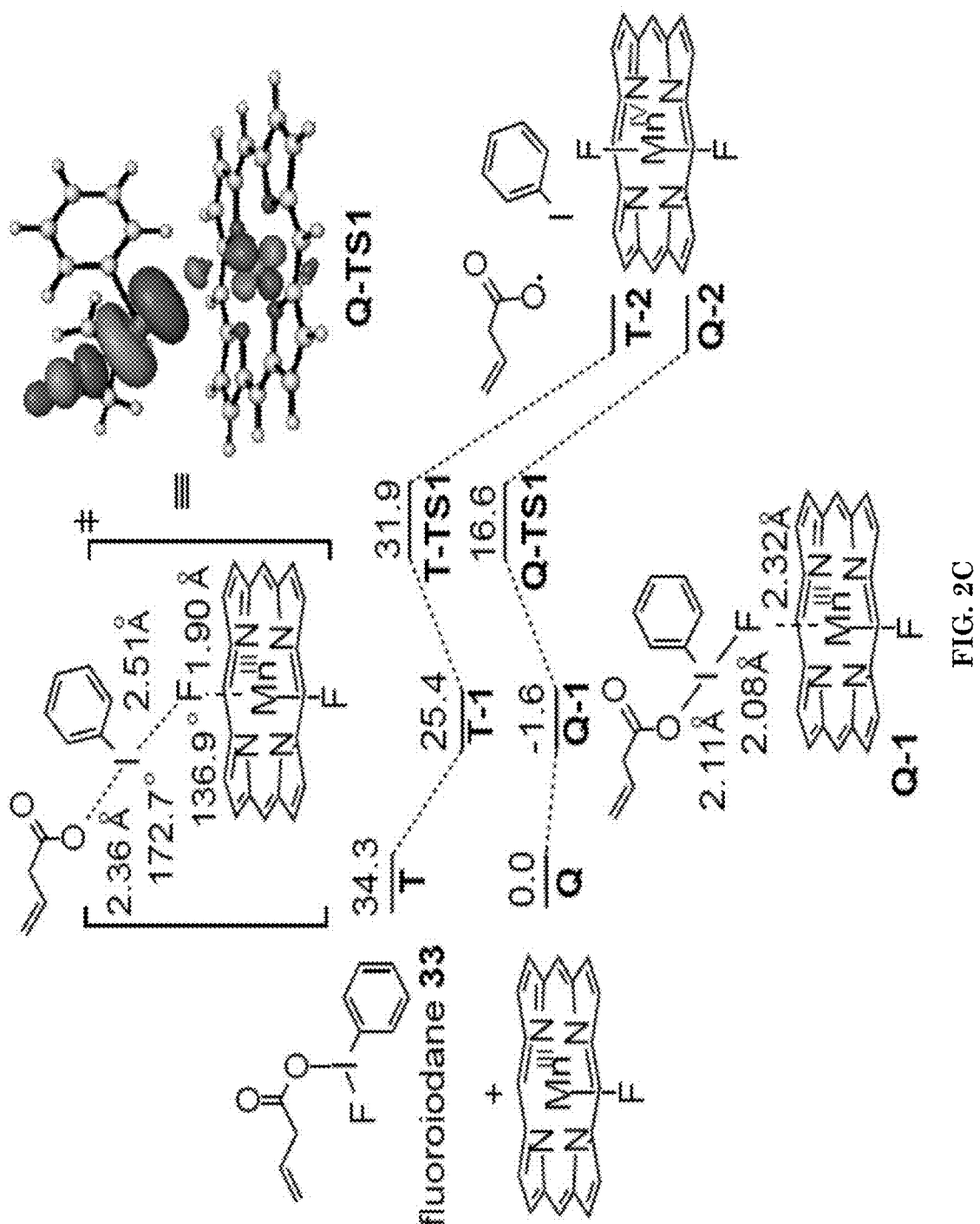

FIGS. 2A-2C illustrate a scheme of fluorination of iodine (III) dicarboxylate. FIG. 2A illustrates fluorination of iodine (III) dicarboxylate 29. To explore whether iodine(III) carboxylates could react with manganese(III) porphyrins to afford the fluorination products, iodobenzene dicarboxylate 29 (bis(α-methylbenzeneacatato)(phenyl)-λ$^3$-iodane) was synthesized and subjected to a DCE solution of Mn(TMP)Cl and Et$_3$N.3HF. Heating the reaction mixture at 45° C. for 1 h afforded (1-fluoroethyl)benzene (30) in 80% yield, demonstrating that the iodine(III) carboxylate complex is highly reactive toward the manganese(III) porphyrin. The formation of an iodine(III) carboxylate was further indicated by NMR spectroscopy. FIG. 2B illustrates $^{19}$F-NMR spectrum of a solution of Mn(TMP)Cl, Et$_3$N.3HF and 2-phenylpropanoic acid 30a. Referring to this figure, it was observed that adding 0.3 equiv of PhIO. into a CD$_2$Cl$_2$ solution of 2-phenylpropanoic acid 30a and 1.0 equiv of Et$_3$N.3HF led to immediate dissolution of solid PhIO. The $^{19}$F-NMR of this clear solution revealed that, besides the resonances of Et$_3$N.3HF (−160 ppm) and difluoroiodobenzene 32 (PhIF$_2$) (−177 ppm),[12] a new resonance, presumably from fluoroiodane 31 (bis(α-methylbenzeneacatato)(phenyl)-λ$^3$-iodane), was observed at −132 ppm.

Figure 3A:
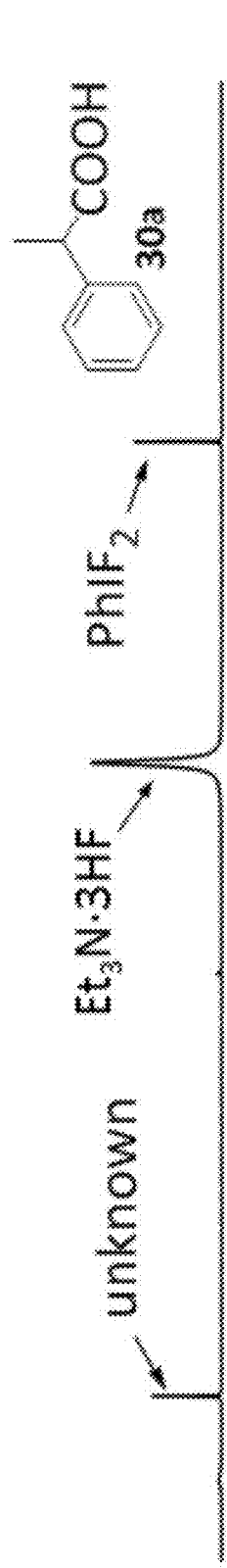
FIGS. 3A-3D illustrate NMR evidence for the formation of an iodine(III) carboxylate complex.
Figure 3B:
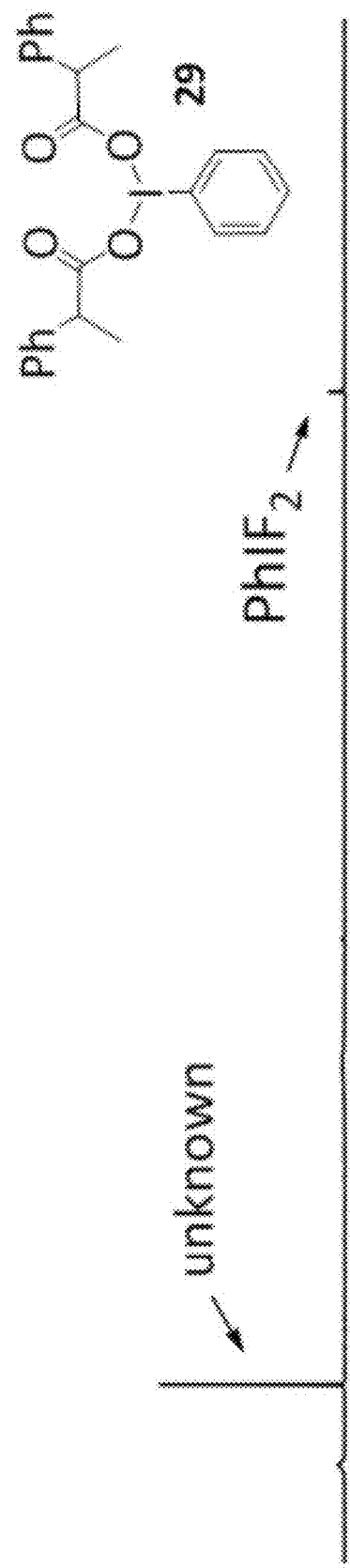
Figures 3C, 3D:
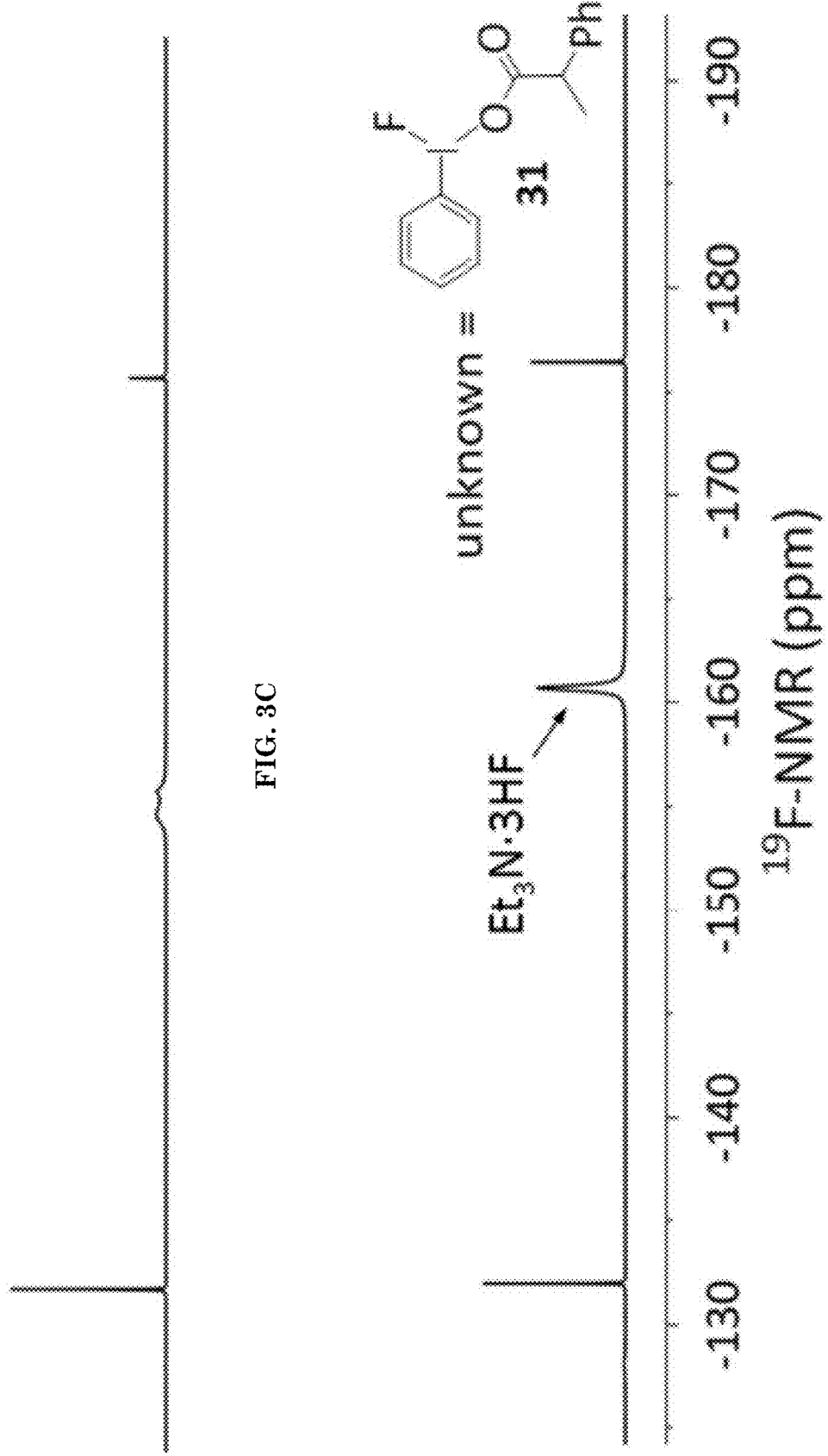

To verify the identity of this new species, a CD$_2$Cl$_2$ solution of iodobenzene dicarboxylate 29 (bis(α-methylbenzeneacatato)(phenyl)-λ$^3$-iodane) was titrated with Et$_3$N.3HF. FIGS. 3A-3D illustrate NMR evidence for the formation of iodine(III) carboxylate complex. FIG. 3A illustrates the NMR spectrum of the solution upon adding of PhIO (0.3 equiv.) into a CD$_2$Cl$_2$ solution of 2-phenylpropanoic acid 30a (1.0 equiv.) and Et$_3$N.3HF (1.0 equiv). FIG. 3B illustrates the NMR spectrum of the solution upon titration of CD$_2$Cl$_2$ solution of iodobenzene dicarboxylate 29 (1.0 equiv.) with Et$_3$N.3HF (0.1 equiv.). FIG. 3C illustrates the NMR spectrum of the solution upon titration of CD$_2$Cl$_2$ solution of iodobenzene dicarboxylate 29 (1.0 equiv.) with Et$_3$N.3HF (0.4 equiv.). FIG. 3D illustrates the NMR spectrum of the solution upon titration of CD$_2$Cl$_2$ solution of iodobenzene dicarboxylate 29 (1.0 equiv.) with Et$_3$N.3HF (1.5 equiv.). Upon addition of the first equiv. of HF (0.33 equiv. Et$_3$N.3HF), the resonance at −132 ppm was predominant in $^{19}$F-NMR spectrum with only a small amount of PhIF$_2$. Further addition of Et$_3$N.3HF led to a gradual increase of the PhIF$_2$ resonance (−177 ppm) and concomitant decrease of the −132 ppm resonance. These results clearly show that PhIO reacts rapidly with carboxylic acids and Et$_3$N.3HF to form iodine(III) carboxylate esters. Furthermore, adding 2 mol % Mn(TMP)Cl catalyst to the clear solution made from 2-phenylpropanoic acid 30a, Et$_3$N.3HF and PhIO afforded fluoroethylbenzene in 40% yield based, which, again, demonstrates that iodine(III) carboxylate complex can react productively with the manganese porphyrin catalyst.

The formation of carboalkoxy radicals through the interaction between the iodine(III) carboxylate and manganese porphyrin is also supported by DFT calculations. FIG. 2C illustrates potential energy surfaces (kcal/mol) for the formation of carboxyl radicals through the interaction of iodine (III) carboxylate complex and manganese(III) porphyrin. Referring to this figure, T and Q refer to triplet and quintet states, respectively. Manganese(III) porphine (Mn(PorH)F) and 3-butenoic acid were employed as model compounds for computational studies. The lowest energy reaction profile was on the quintet energy surface, as expected for a manganese(III) porphyrin. The fluoroiodane 33 ((3-butenoicacetato)fluoro(phenyl)-λ$^3$-iodane) first forms an adduct with the manganese(III) porphyrin, which is thermodynamically favored by 1.6 kcal/mol. This adduct then undergoes a facile dissociation at the iodine center with a barrier of 18.2 kcal/mol. In the transition state, the frontier orbital interaction involves the d$_{yz}$ orbital of Mn(PorH)F and the σ*orbital of the O—I—F bond with bonding interactions between the fluorine and the manganese. Significant elongations of both the I-O bond (from 2.11 Å in Q-1 to 2.36 Å in Q-TS1) and the I-F bond (from 2.08 Å to 2.51 Å) are observed with a concurrent contraction of the Mn—F bond length (from 2.32 Å to 1.90 Å). These results are consistent with a dissociation of the carboalkoxy radical from iodine with a synchronous F-atom transfer to Mn(III) to afford F—Mn(IV)—F.

Example 5—Study of Fluorine Transfer Step

Scheme 4 illustrates mechanistic studies of fluorine transfer step. For the fluorine transfer step, the radical nature of the reaction was demonstrated by adding 5 equiv. CCl$_3$Br as an alkyl radical trap. Scheme 4 (eq. 4) shows that the major product was the alkyl bromide 1b with a fluorination/ bromination ratio of 1:2. Since the rate constant for bromine transfer from $BrCCl_3$ to alkyl radicals is known to be $\sim10^8$ $M^{-1}s^{-1}$,[25] the 1:2 fluorination/bromination ratio corresponds to a nano-second radical lifetime, which is comparable to the manganese porphyrin-catalyzed C—H fluorination reaction. This result suggests a similar intermediate, presumably a fluoromanganese(IV) porphyrin complex, that rapidly traps the substrate radical affording the alkyl fluoride product.

Example—6—Decarboxylative Fluorination and Production [$^{18}$F]Trifluoromethoxy and [$^{18}$F]Trifluoromethyl Groups Under the same conditions for decarboxylative [$^{18}$F] fluorination, α,α-difluoronaphthoxyacetic acid and α,α-difluorophenylacetic acid also react to afford [$^{18}$F]trifluoromethoxy and [$^{18}$F]trifluoromethyl groups.

Scheme 4. Mechanistic studies of the fluorine transfer step.

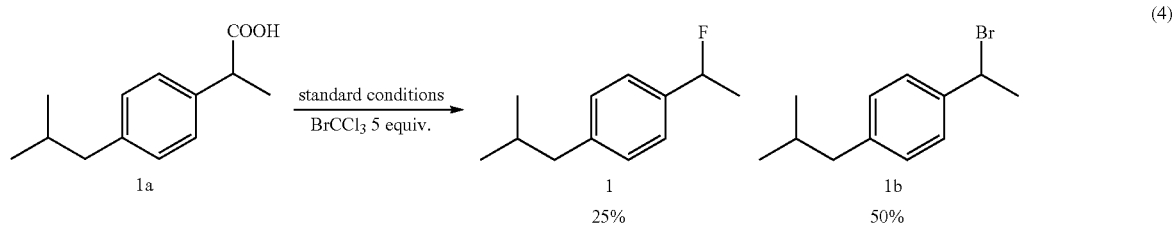

(4)

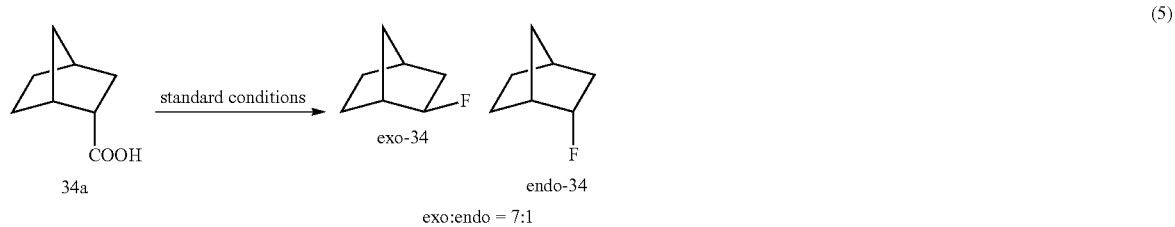

(5)

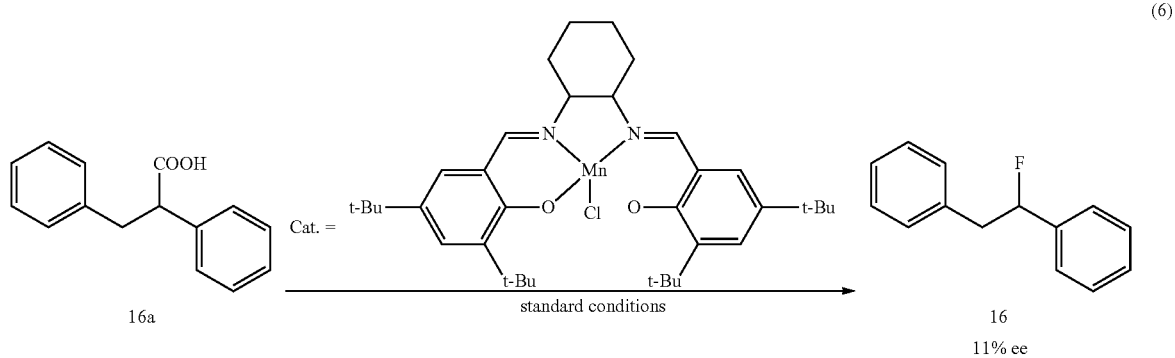

(6)

Scheme 4 (eq, 5) further demonstrates the involvement of a manganese-bound fluoride intermediate by fluorination of endo-norbornane-2-carboxylic acid (34a) which yielded exo-2-fluoronorbornane as the major product (exo:endo=7:1).

The observed selectivity is consistent with the C—H fluorination of norbornane by Mn(TMP)Cl (exo:endo=6:1),[14] and the preference for the exo product is likely due to steric interactions between the alkyl radical and the bulky manganese porphyrin catalyst during the fluorine transfer step.

Scheme 4 (eq. 6) illustrates that when a chiral manganese salen complex was used as the catalyst, fluorination of acid 15a afforded 15 in 11% ee. This low but mechanistically informative ee provides strong additional support for a manganese-bound fluoride intermediate in the fluorine transfer step.

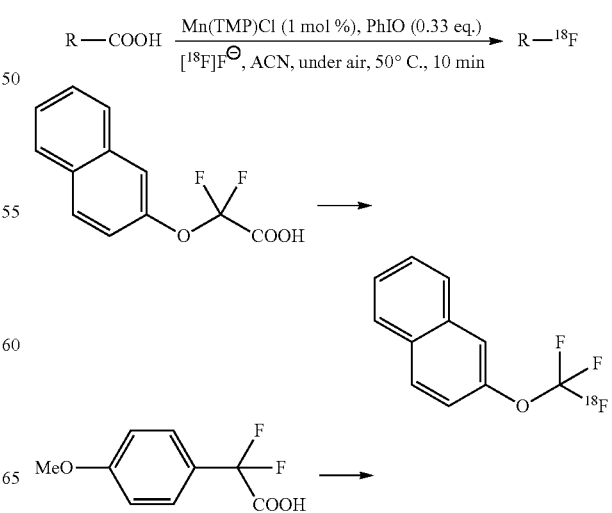

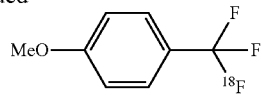

The [¹⁸F]fluoride was prepared as follows. A 4 mL vial with a screw cap was charged with substrate (0.22 mmol), iodosylbenzene (0.068 mmol) and a stir bar (2×5 mm). A portion of aqueous [¹⁸F]fluoride solution (40-50 μL, 4-5 mCi) obtained from the cyclotron was loaded on to an Chromafix PS-HCO₃ IEX cartridge, which had been previously washed with 5.0 mg/mL K₂CO₃ in Milli-Q water followed by 5 mL of Milli-Q water. Then, the cartridge loaded with [¹⁸F]fluoride was washed with 2 mL Milli-Q water and [¹⁸F]fluoride was released from the cartridge using 0.8 mL 5.0 mg/mL K₂CO₃ in Milli-Q water. A portion of the resulting [¹⁸F]fluoride solution (25 μL, 125-150 μCi) was diluted with 3.0 mL acetonitrile. 0.6 mL of this [¹⁸F] fluoride acetonitrile solution was added to the vial containing the substrate and the oxidant. The resulting mixture was stirred for 2 min under 50° C. (for most of the cases, PhIO solid will dissolve during the stirring). Then 2 mg Mn(TMP) Cl catalyst (0.0023 mmol) was added in solid form to the reaction mixture. The vial was recapped and stirred at 50° C. for 10 more min. After 10 min, an aliquot of the reaction mixture was taken and spotted on a silica gel TLC plate. The plate was developed in an appropriate eluent and scanned with a Bioscan AR-2000 Radio TLC Imaging Scanner. The detected radiochemical conversion was around 1%.

Example 7—Experimental Section

Unless otherwise noted, fluorination reactions were run under nitrogen atmosphere with no precautions taken to exclude moisture. Tetramesityl porphyrin (TMP) and tetra-p-tolylporphyrin (TTP) were prepared as previously reported.[26] Tetrakis(pentafluorophenyl)porphyrin (TPFPP) and Tetrakis(2,6-dichlorophenyl)porphyrin (TDCPP) were purchased from Frontier Scientific. All manganese porphyrins were synthesized as chloride salts according to literature methods.[27] Iodosylbenzene (PhIO) was prepared by hydrolysis of iodobenzene diacetate with sodium hydroxide solution. Carboxylic acid substrates 5a,[28] 7a,[29] 8a,[30] 11a,[31] 13a,[32] 21a,[33] 25a,[34] 26a,[35] 27a,[36] iodine dicarboxylate 28,[37] were synthesized as previously reported. Other purchased materials were of the highest purity available from commercial sources and used without further purification. ¹H NMR spectra were obtained on a Bruker NB 300 spectrometer or a Bruker Avance-III (500 MHz) spectrometer and are reported in ppm using solvent as an internal standard (CDCl₃ at δ 7.26, acetone-d₆ at 2.04, or methylene chloride-d₂ at 5.32). Data reported as: chemical shift (δ), multiplicity (s=singlet, d=doublet, t=triplet, q=quartet, m=multiplet), coupling constant (Hz); integrated intensity. ¹³C NMR spectra were recorded on a Bruker 500 (126 MHz) or a Bruker NB 300 (75 MHz) spectrometer and are reported in ppm using solvents as an internal standard (CDCl₃ at 77.15 ppm, acetone-d₆ at 29.92 ppm, or methylene chloride-d₂ at 54.0). ¹⁹F NMR spectra (282 MHz) were obtained on a Bruker NB 300 spectrometer and are reported in ppm by adding external neat PhF (¹⁹F, δ−113.15 relative to CFCl₃). GC/MS analyses were performed on an Agilent 7890A gas chromatograph equipped with an Agilent 5975 mass selective detector. High-resolution mass spectra were obtained from the Princeton University mass spectrometer facility by electrospray ionization (ESI). High-performance liquid chromatography (HPLC) was performed on an Agilent 1100 series instrument with a binary pump and a diode array detector.

Example 7.1—Experimental Details for Decarboxylative Fluorination Catalyzed by Mn(TMP) Cl

Example 7.1.1—General Procedure for Decarboxylative Fluorination Catalyzed by Mn(TMP) Cl An oven-dried, 5 mL Schlenk flask equipped with a stir bar was placed under an atmosphere of N₂. Mn(TMP)Cl Catalyst (11 mg, 0.0125 mmol, 2.5 mol %), acid substrate (0.5 mmol), Et₃N.3HF (0.1 mL, 0.61 mmol, 1.2 equiv.) and benzoic acid (30 mg, 0.25 mmol, 0.5 equiv.) were then added, followed by 1.0 mL 1,2-dichloroethane (DCE). The reaction mixture was then heated to 45° C.

Under a stream of N₂, iodosylbenzene (370 mg, 1.6 mmol, 3.3 equiv.) was added slowly to the reaction mixture in solid form over a period of 45 minutes-1.5 hours. The reaction was monitored by GC/MS analysis with 25 mg naphthalene (0.195 mmol, 0.39 equiv.) added as internal standard. After the addition of iodosylbenzene, the solution was cooled to room temperature and the product was separated from the reaction residue by silica gel column chromatography.

Example 7.1.2—Procedure for Decarboxylative Fluorination of Ibuprofen in the Presence of BrCCl₃

An oven-dried, 5 mL Schlenk flask equipped with a stir bar was placed under an atmosphere of N₂. Mn(TMP)Cl Catalyst (11 mg, 0.0125 mmol, 2.5 mol %), acid substrate (0.5 mmol), Et₃N.3HF (0.1 mL, 0.61 mmol, 1.2 equiv.), benzoic acid (30 mg, 0.25 mmol, 0.5 equiv.) were then added, followed by BrCCl₃ (246 μL, 2.5 mmol, 5 equiv.) and DCE (1.0 mL). The reaction mixture was then heated to 45° C. Under a stream of N₂, iodosylbenzene (330 mg, 1.5 mmol, 3.0 equiv.) was added slowly to the reaction mixture in small portions over a period of 1 hour. The reaction solution was then cooled to room temperature. 20 μL fluorobenzene was added. Yield was determined by ¹⁹F NMR by taking aliquot of the reaction solution and diluted with CDCl₃. The bromination/fluorination ratio was determined by GC/MS and the ¹H NMR of the reaction mixture.

Example 7.1.3—Procedure for Reaction of Pre-Stirred Solution of 2-Phenylpropionic Acid, Et₃N.3HF, and PhIO with Mn(TMP)Cl Catalyst An oven-dried, 5 mL Schlenk flask equipped with a stir bar was placed under an atmosphere of N₂. 2-phenylpropionic acid (65 μL, 0.5 mmol), Et₃N.3HF (81 μL, 0.5 mmol, 1 equiv.) and 0.5 mL CD₂Cl₂ and 33 mg of PhIO (0.15 mmol, 0.3 equiv.) were added to the flask. The reaction mixture was stirred for 5 minutes. A 0.5 mL CD₂Cl₂ solution of 11 mg Mn(TMP)Cl (0.0126 mmol, 2.5 mol %) was then added to the solution via syringe. The flask was placed in a 45° C. water bath and stirred for 20 minutes. The reaction solution was then cooled to room temperature. 10 μL fluorobenzene was added. Yield was determined by ¹⁹F NMR.

Example 7.1.4—Procedure for Reaction of Iodine(III) Dicarboxylate 29 with Mn(TMP)Cl Catalyst A 4 mL vial with magnetic stir bar was charged with 70 mg iodine(III) dicarboxylate 29 (0.14 mmol) and Mn(TMP)Cl catalyst 12 mg (0.014 mmol, 10 mol %). The vial was capped and evacuated and backfilled with $N_2$ for three times. 0.5 mL DCE was then added. The reaction mixture was placed in a 45° C. water bath and stirred for 1 hour. The reaction solution was then cooled to room temperature. 10 μL fluorobenzene was added. Yield was determined by $^{19}F$ NMR by taking aliquot of the reaction solution and diluted with $CDCl_3$.

Example 7.1.5 Procedure for Decarboxylative Fluorination with KF

KF 1 mg (17.0 μmol, 1 equiv.), 18-crown-6 16 mg (30.2 μmol, 1.8 equiv.), and 2 mL ACN were added to a 4 mL vial with stir magnetic stir bar. The obtained solution was sonicated for 2 minutes. 2,3-diphenylpropionic acid 83 mg (367.2 μmol, 21 equiv.) and PhIO 38 mg (172.7 μmol, 10 equiv.) were added to the solution. The mixture was stirred for 2 minutes at room temperature. Mn(TMP)Cl 6 mg (6.8 μmol, 0.4 equiv.) were then added to the solution. The reaction mixture was stirred at 45° C. for 8 minutes. After cooling to room temperature, the solvent was evaporated and 10 μL fluorobenzene was added as internal standard. The yield was determined by $^{19}F$ NMR.

Example 7.1.6—Enantio-Discriminating HPLC Trace of Decarboxylative Fluorination of Acid 16a Compound 16a (2,3-diphenylpropanoic acid) was converted into the fluorinated product (compound 16: (1-fluoroethane-1,2-diyl)dibenzene)) by targeted fluorination shown in Scheme 3a. The analysis was performed using HPLC gradient: 2% IPA/hexanes, isocratic, 1 mL/min, column: Chiralcel OJ-H.

Compound 16

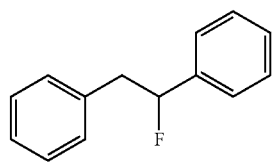

Figure 4:
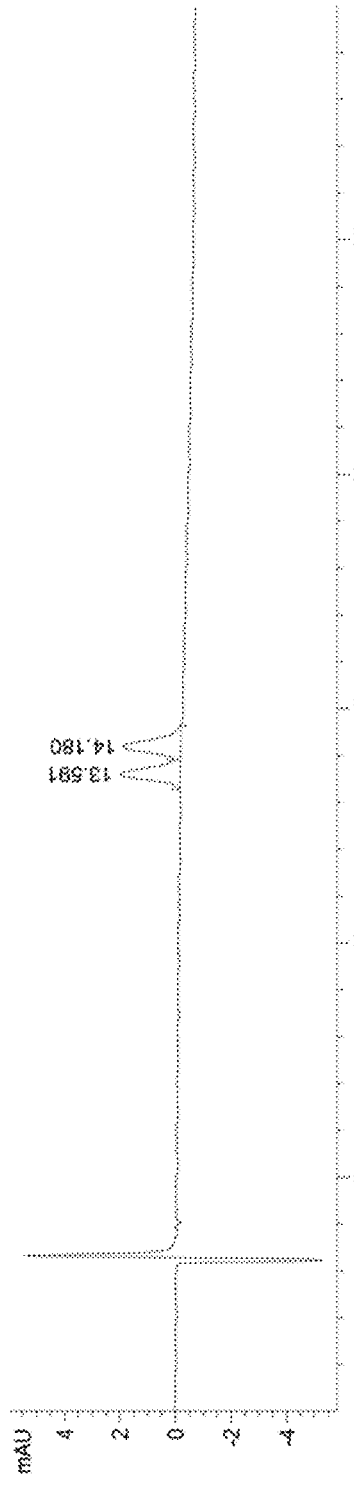
FIG. 4 illustrates the chiral UV-HPLC trace of authentic racemic compound 16 (1-fluoroethane-1,2-diyl)dibenzene).
Figure 4:
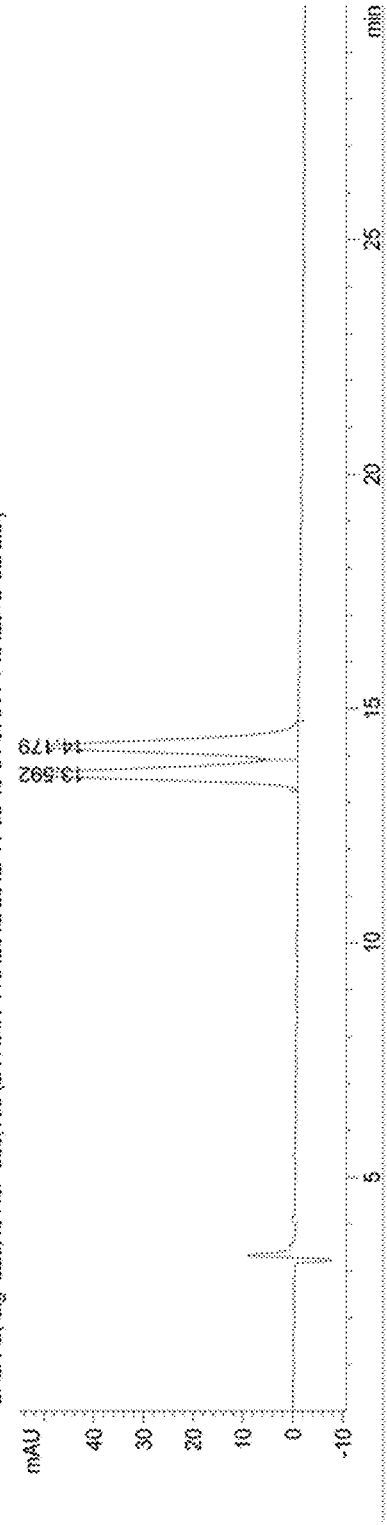
Figure 5:
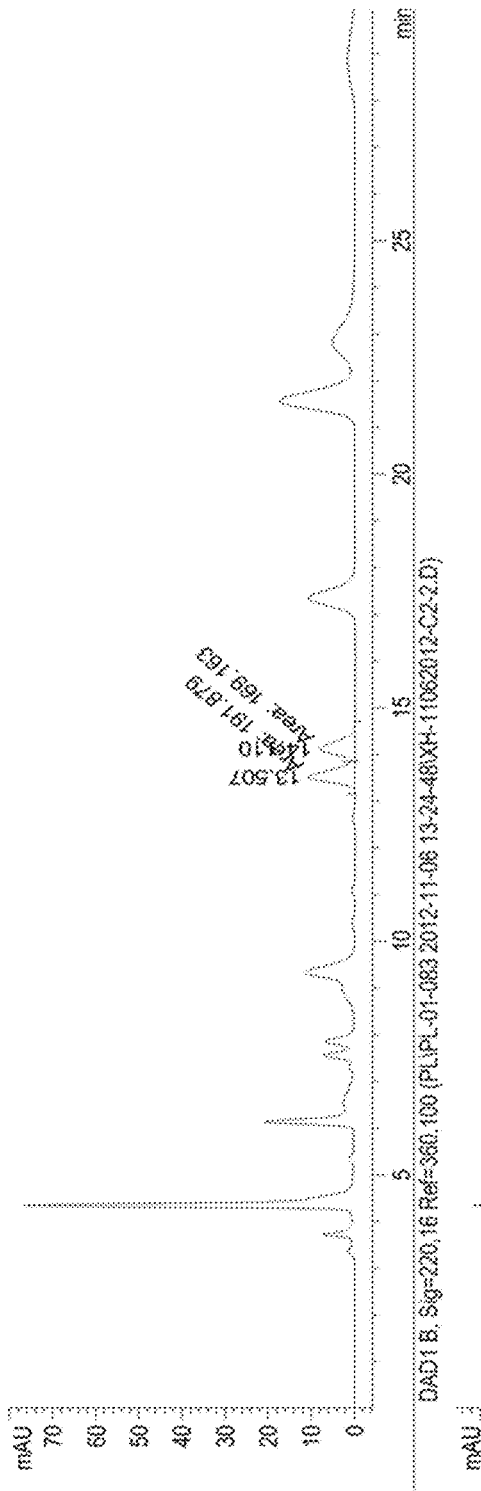
FIG. 5 illustrates the chiral UV-HPLC trace of reaction mixture of decarboxylative fluorination of acid compound 16a (2,3-diphenylpropanoic acid).
Figure 5:
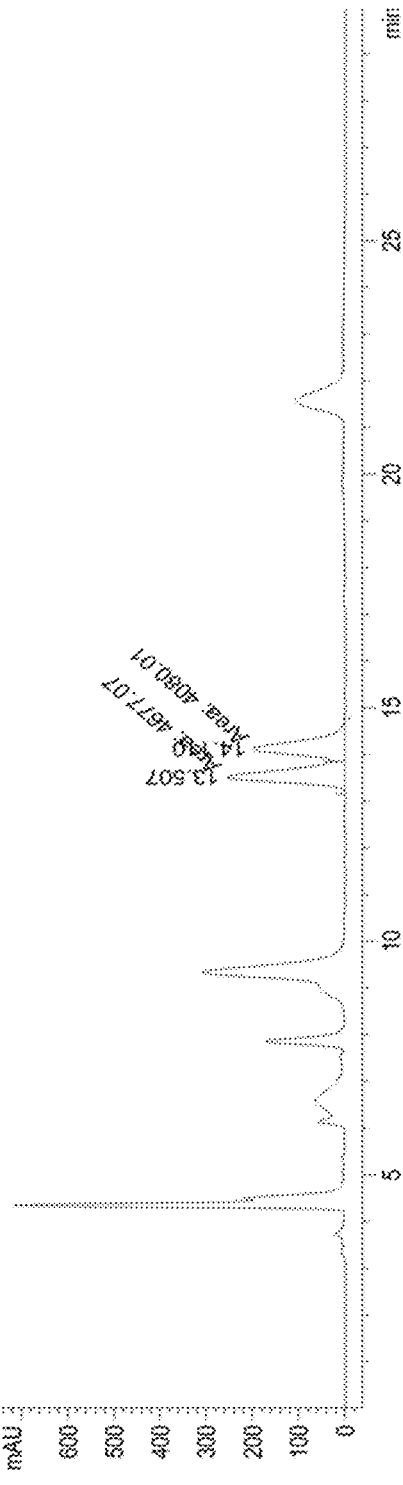

FIG. 4 illustrates the chiral UV-HPLC trace of authentic racemic compound 16. FIG. 5 illustrates the chiral UV-HPLC trace of reaction mixture of decarboxylative fluorination of acid 16a.

Example 7.2 NMR Spectra of Fluorination Product

Example 7.2.1—Scheme 2, Compound 1

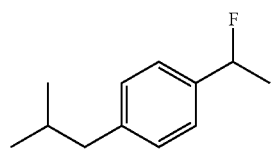

Figure 6A:
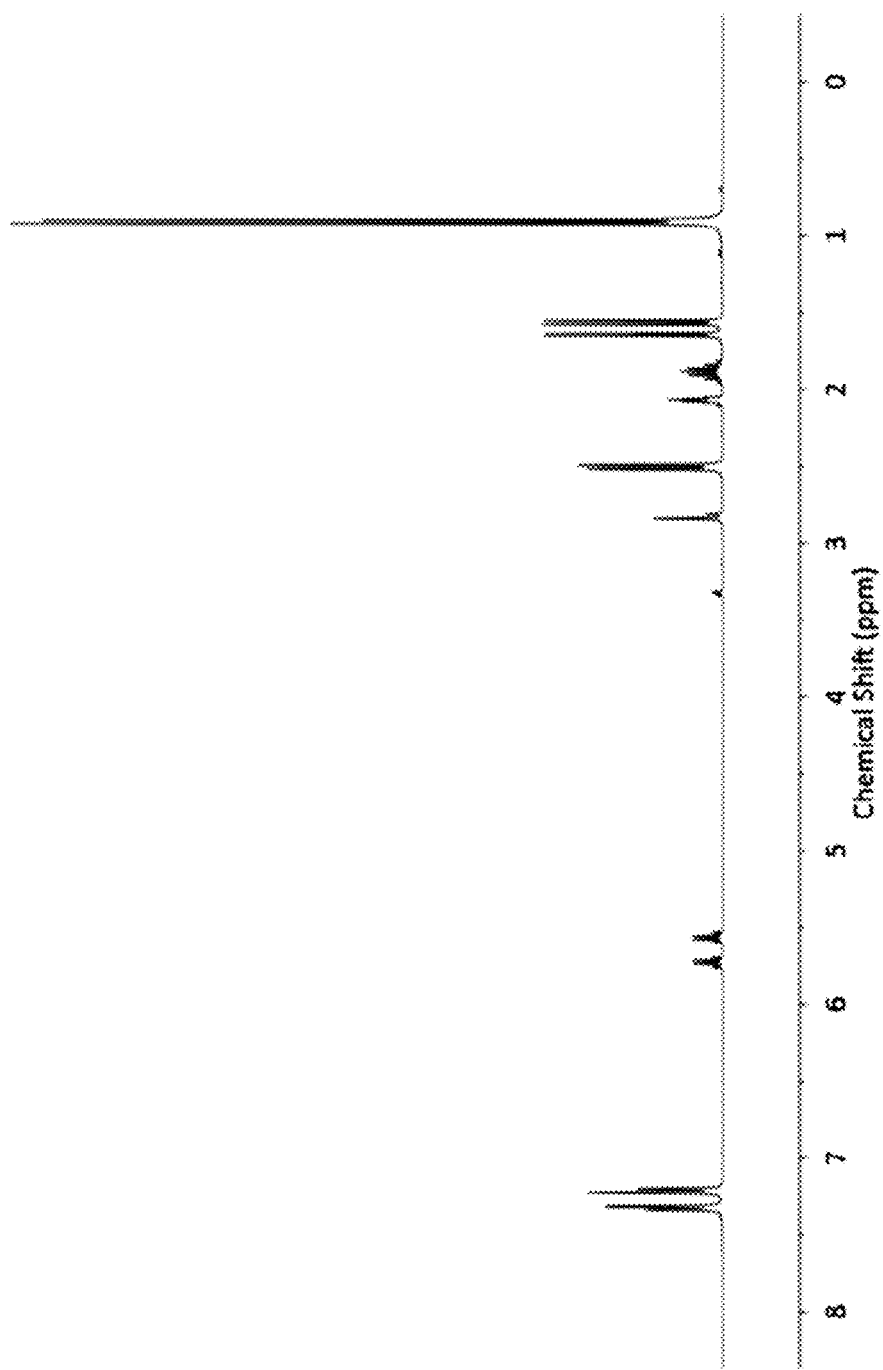
FIGS. 6A-6C illustrate the NMR spectra of 1-(1-fluoroethyl)-4-isobutylbenzene.
Figure 6B:
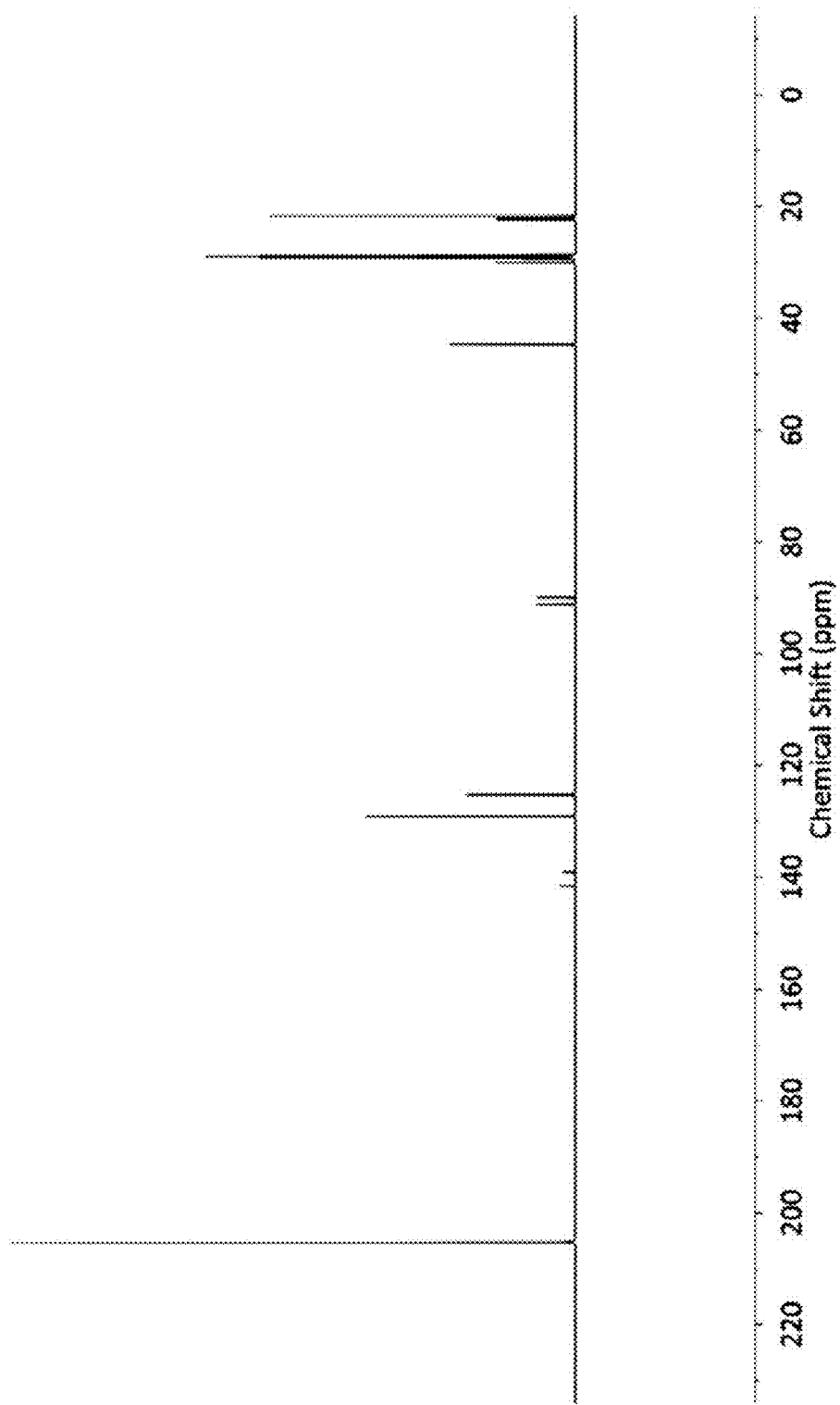
Figure 6C:
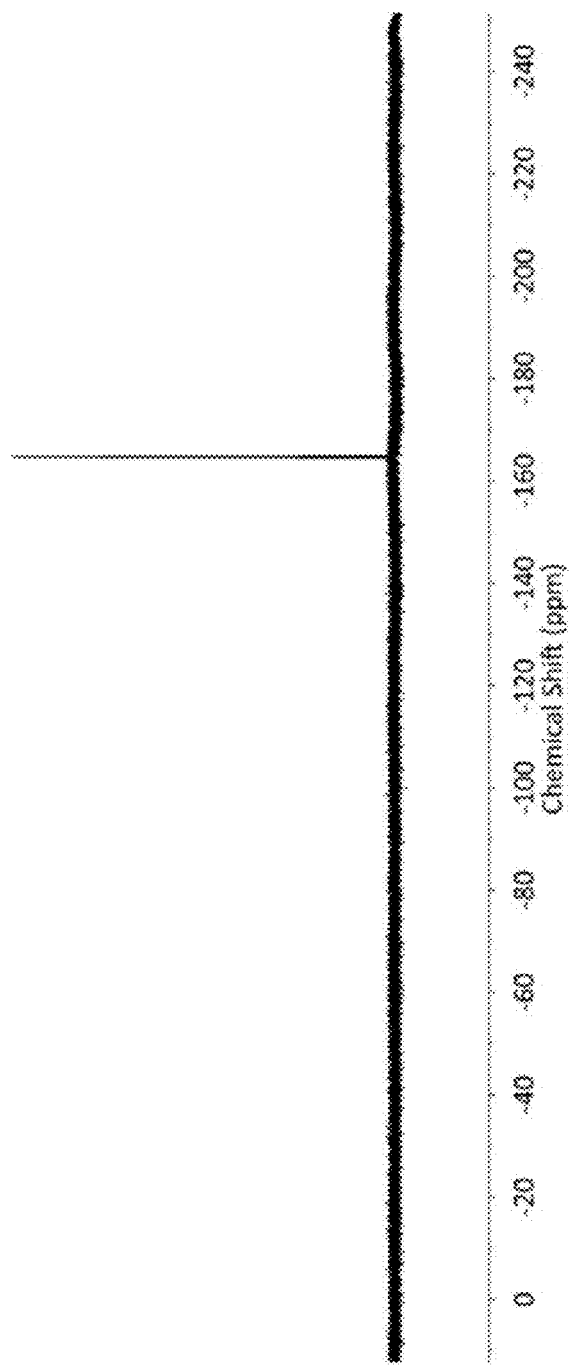
Figure 7:
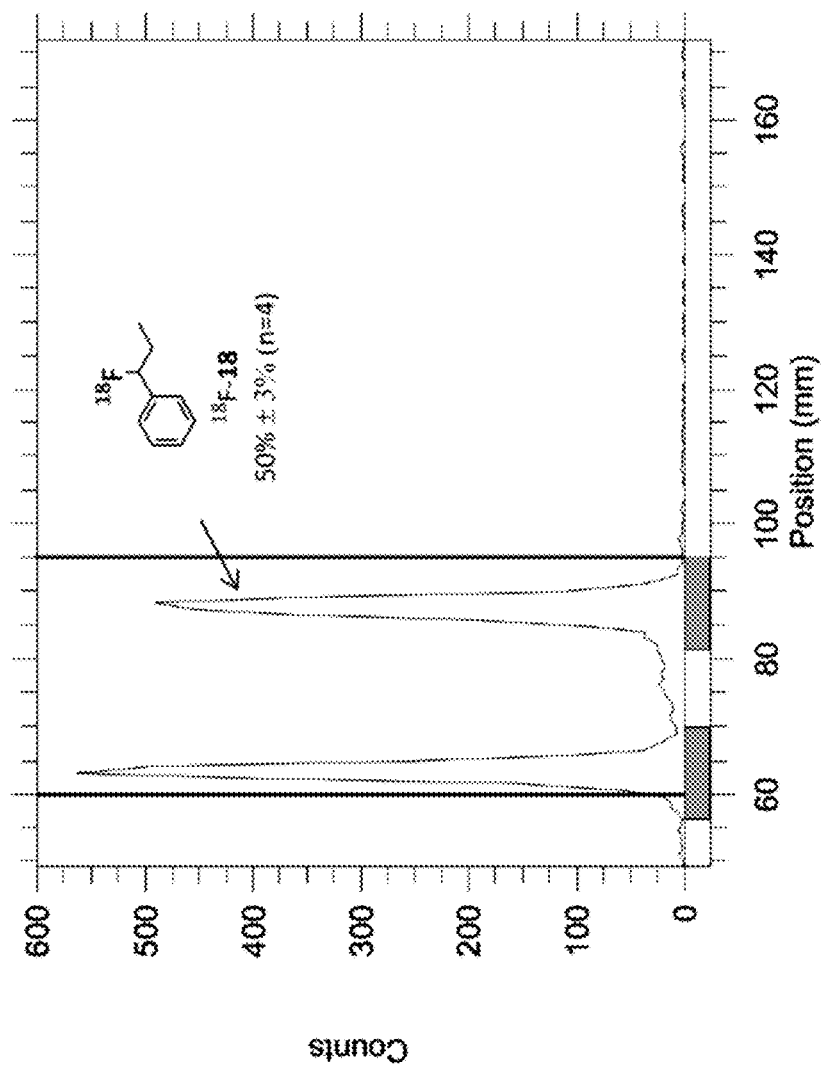
FIGS. 7-14 illustrate examples of the radio-TLC scans of the compounds: ¹⁸F-18 ([¹⁸F](1-fluorobutyl)benzene); ¹⁸F-14 ([¹⁸F]2,4-dichloro-1-(1-fluoroethoxy)benzene)e; ¹⁸F-25 ([¹⁸F](fluoromethylene)dicyclohexane); ¹⁸F-19 ([¹⁸F]4-(fluoromethyl)biphenyl); ¹⁸F-8 ([¹⁸F]4-fluoro-4-phenylbutanenitrile); ¹⁸F-17 ([¹⁸F]2-(1-fluoro-2-phenylethyl)isoindoline-1,3-dione); ¹⁸F-15 ([¹⁸F]2-(fluoromethoxy)naphthalene); and ¹⁸F-5 ([¹⁸F]2-(fluoro(phenyl)methyl)isoindoline-1,3-dione) described herein.
Figure 8:
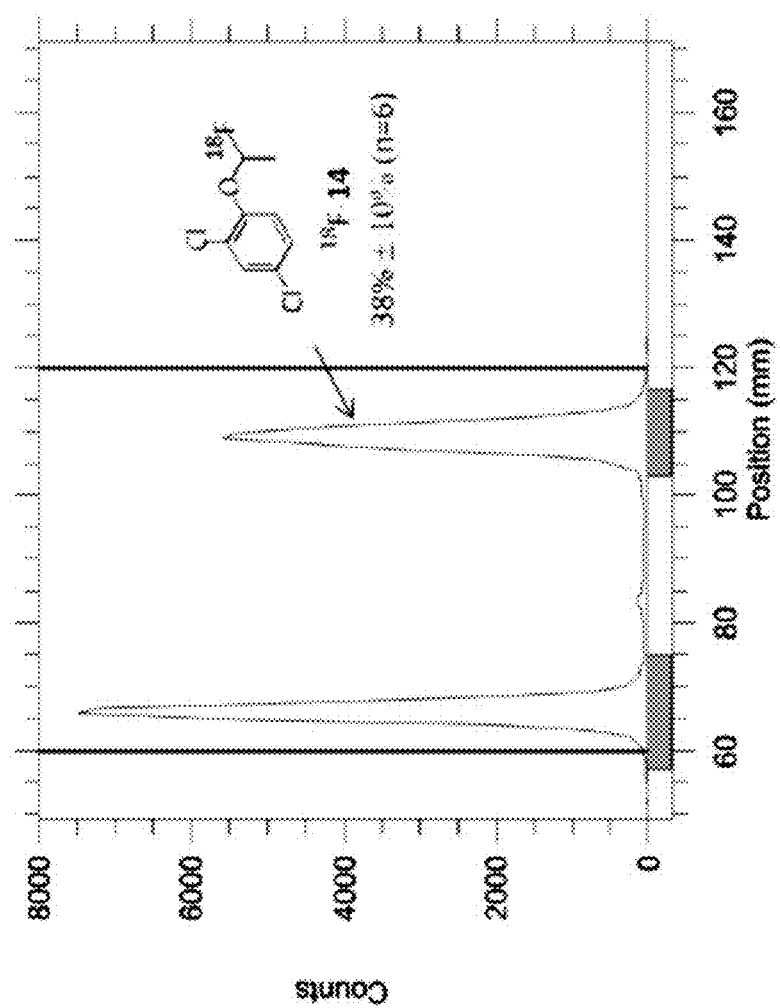
Figure 9:
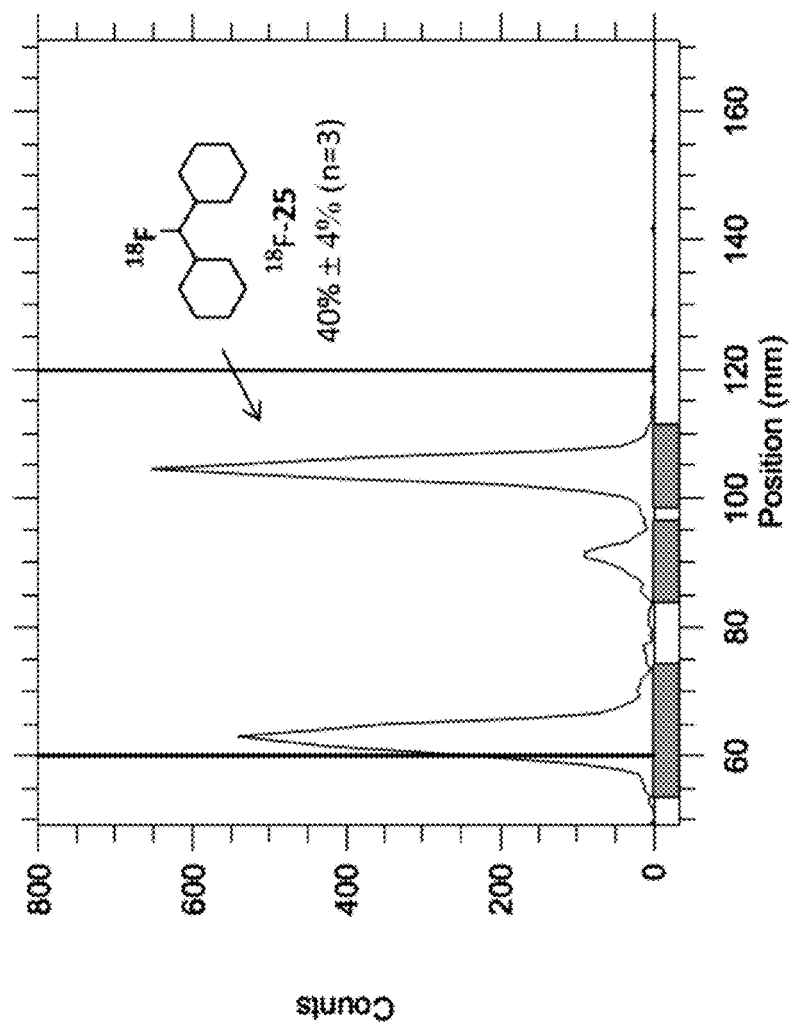
Figure 10:
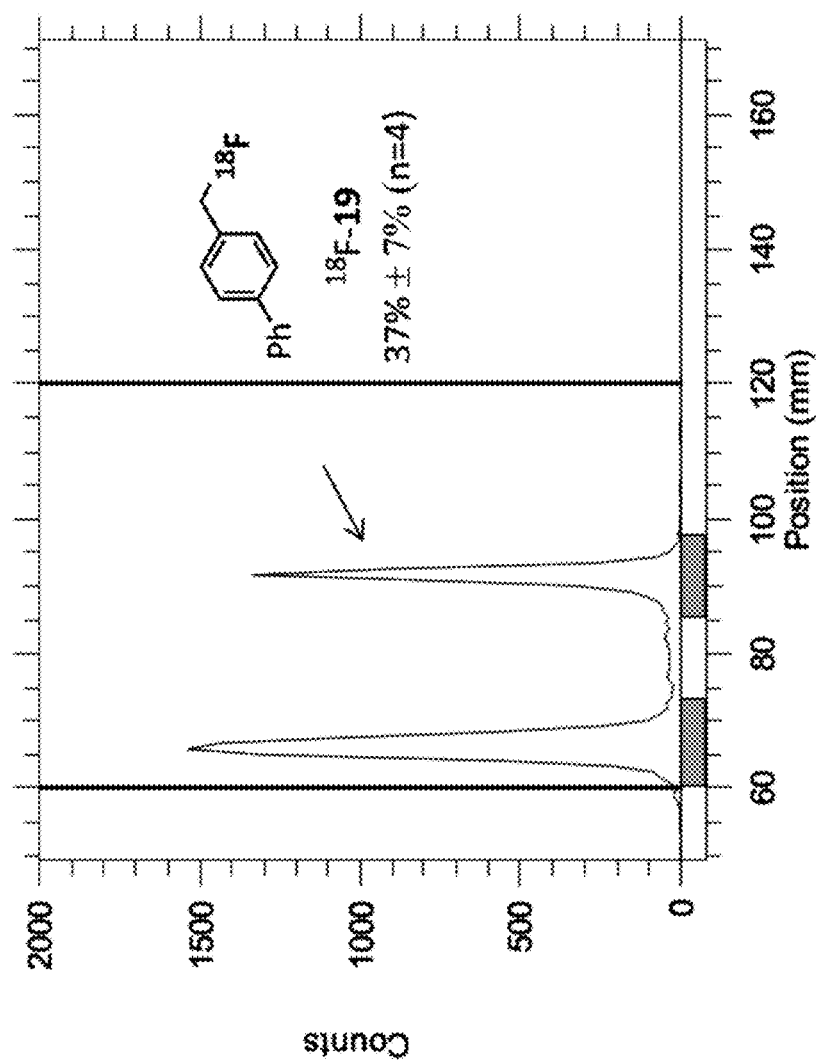
Figure 11:
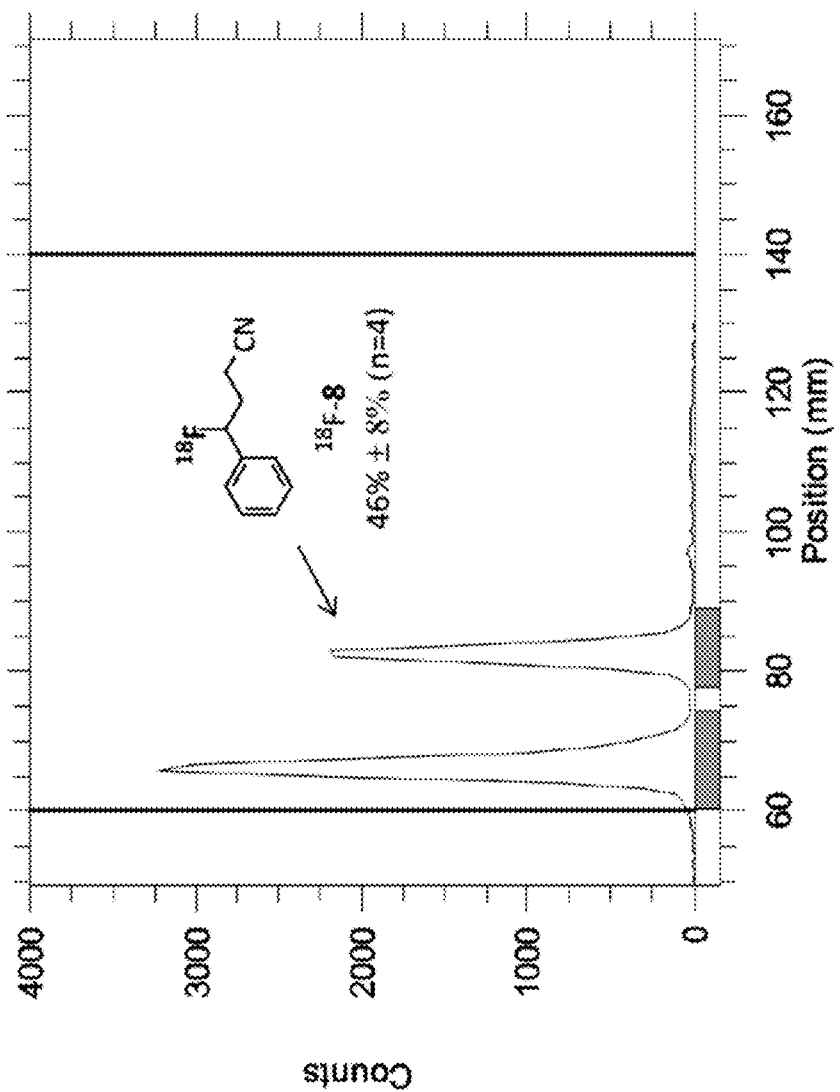
Figure 12:
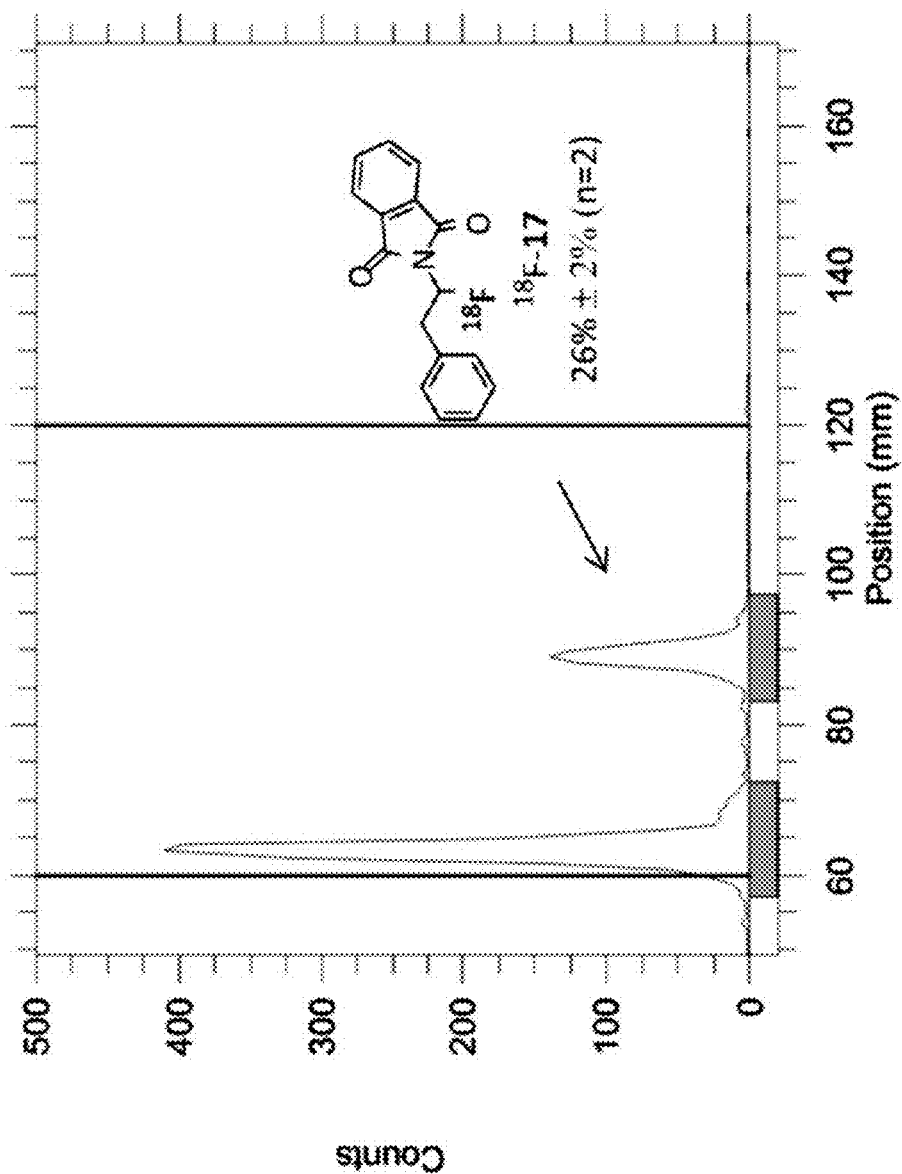
Figure 13:
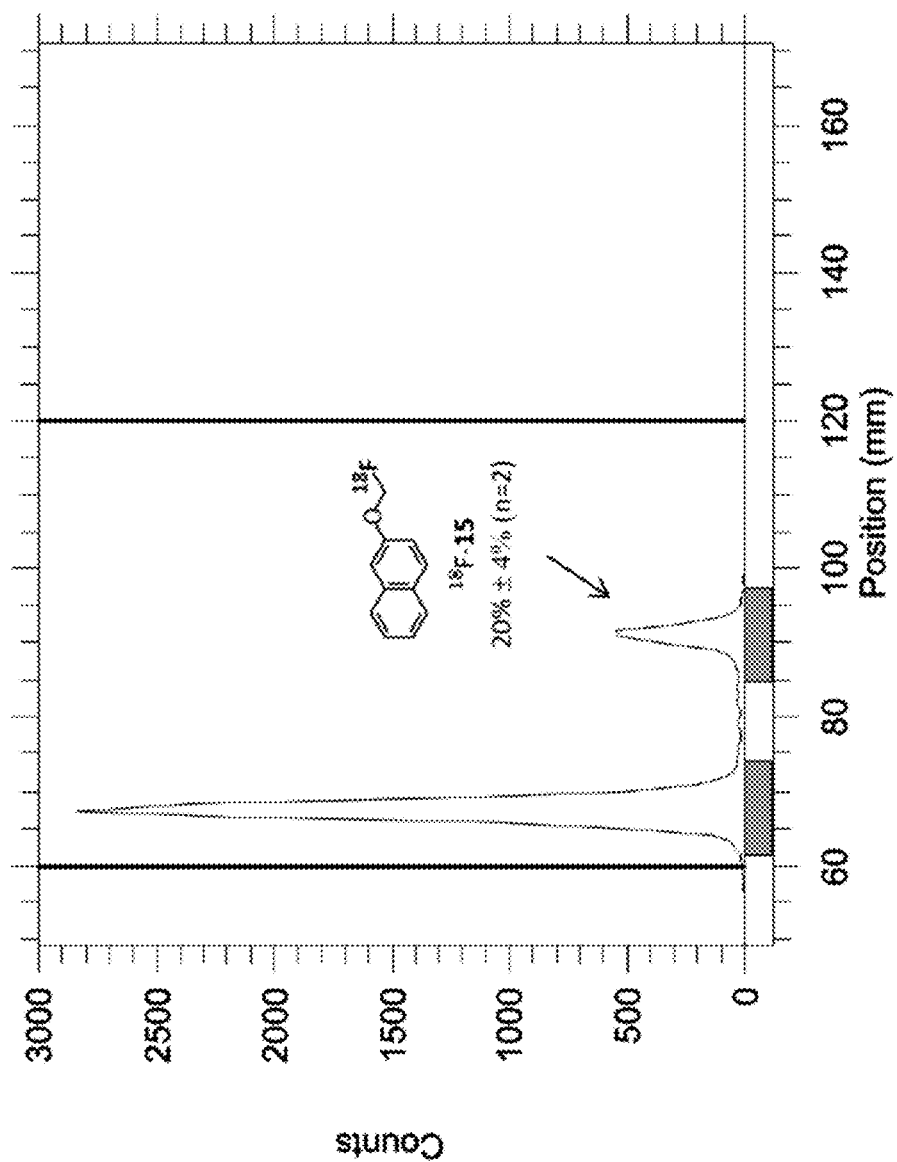
Figure 14:
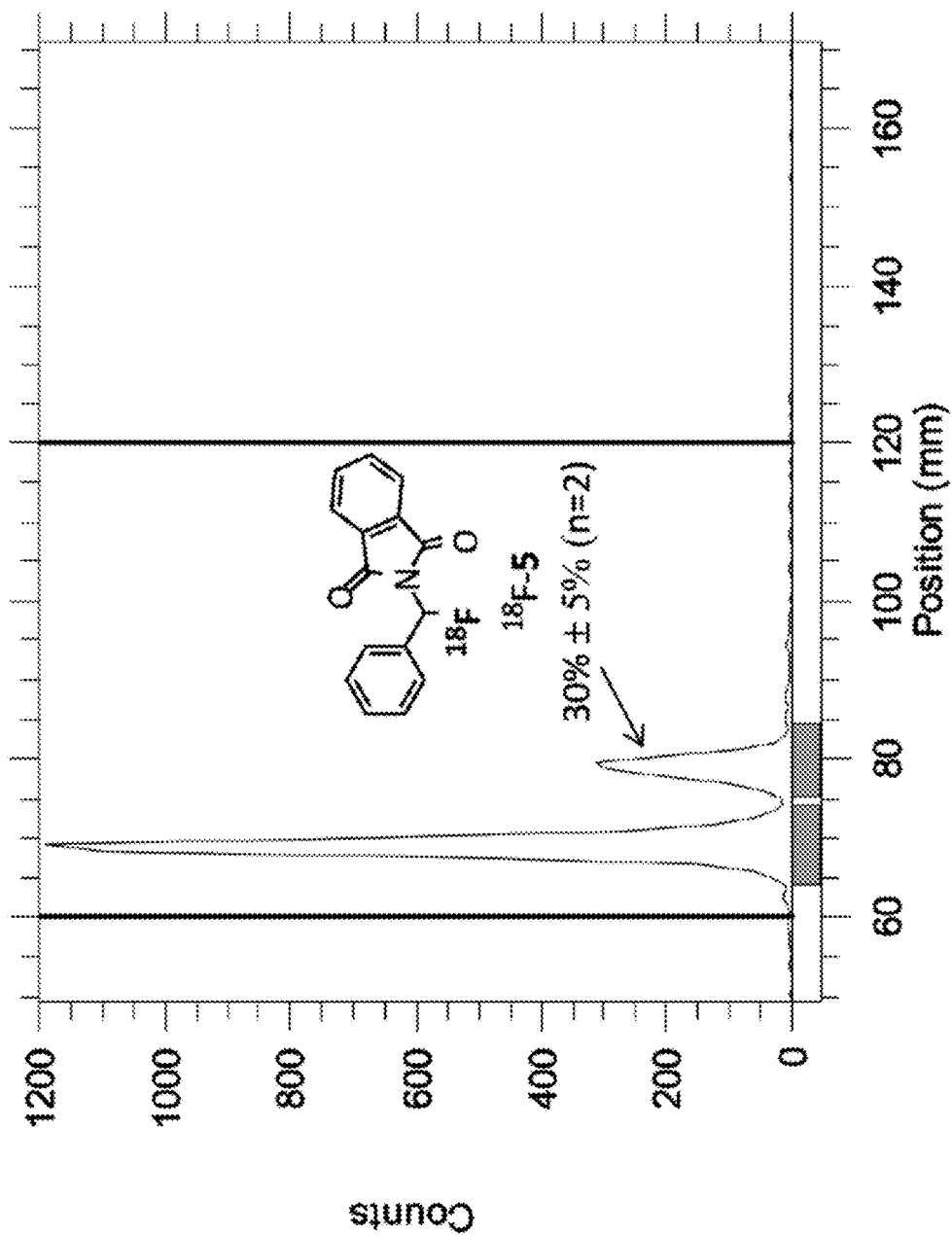

The reaction was performed according to general procedure in group) had the structure of compound 1, but with a —COOH in place of —F. In this case, the substrate was ibuprophen. Purification by column chromatography (hexanes). $^1H$ NMR (300 MHz, Acetone-$d_6$) δ 7.30 (m, 2H), 7.18 (m, 2H), 5.62 (dq, J=47.9, 6.4 Hz, 1H), 2.48 (d, J=7.2 Hz, 2H), 1.86 (dp, J=13.6, 6.8 Hz, 1H), 1.58 (dd, J=23.6, 6.4 Hz, 3H), 0.88 (d, J=6.6 Hz, 6H); $^{13}C$ NMR (126 MHz, Acetone-$d_6$) δ 142.5, 140.0, 129.9, 126.1, 91.5 (d, J=165.6 Hz), 45.6, 31.0, 23.1 (d, J=25.6 Hz), 22.6; $^{19}F$ NMR (282 MHz, Chloroform-d) δ–165.09 ppm (dq, J=47.4, 23.6 Hz, 1F); MS (EI) m/z cal'd $C_{12}H_{17}F$ [M]$^+$: 180.1, found 180.1. FIGS. 6A-6C illustrate the NMR spectra of compound 1. FIG. 6A illustrates the $^1H$ NMR spectrum of compound 1. FIG. 6B illustrates the $^{13}C$ NMR spectrum of compound 1. FIG. 6C illustrates the $^{19}F$ NMR spectrum of compound 1.

Compounds 2-22 and 26-28 were also analyzed by $^1H$, $^{13}C$ and $^{19}F$ NMR spectroscopy, and the corresponding data are presented in Examples 6.2.2-6.2.25 herein. The diagrams of the compounds 2-22 and 26-28 are not presented since the skilled person would understand the results based on the descriptions of the data.

Example 7.2.2—Compound 2

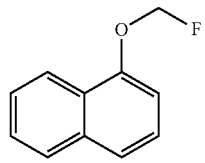 [SMILES: FCOc1cccc2ccccc12]

The reaction was performed according to general procedure in Example 7.1 above. The substrate (compound containing a carboxyl group) had the structure of compound 2, but with a —COOH in place of —F. In this case, the substrate was 2-(naphthalen-1-yloxy)acetic acid. Purification by column chromatography (hexanes to 2% EtOAc/hexanes). $^1H$ NMR (300 MHz, $CDCl_3$) δ 8.30 (m, 1H), 7.90 (m, 1H), 7.63 (m, 1H), 7.58 (m, 2H), 7.47 (t, J=8.0 Hz, 1H), 7.24 (dt, J=7.6, 1.2 Hz, 1H), 5.97 (d, J=54.4 Hz, 2H); $^{13}C$ APT NMR (75 MHz, $CDCl_3$) δ 152.8, 134.6, 127.6, 126.6, 125.9, 125.7, 123.3, 121.7, 109.0, 101.0 (d, J=219.0 Hz); $^{19}F$ NMR (282 MHz, $CDCl_3$)–149.12 ppm (t, J=54.3 Hz, 1F); MS (EI) m/z cal'd $C_{11}H_9OF$ [M]$^+$: 176.1, found 176.1.

Example 7.2.3—Compound 3

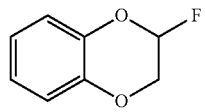 [SMILES: FC1COc2ccccc2O1]

The reaction was performed according to general procedure in Example 7.1 above. The substrate (compound containing a carboxyl group) had the structure of compound 3, but with a —COOH in place of —F. In this case, the substrate was 2,3-dihydrobenzo[b][1,4]dioxine-2-carboxylic acid. Purification by column chromatography (hexanes to 2% EtOAc/hexanes). $^1H$ NMR (300 MHz, Acetone-$d_6$) δ 6.82-7.01 (m, 4H), 6.22 (dt, J=54.0, 1.0 Hz, 1H), 4.45 (ddd, J=12.4, 4.7, 1.3 Hz, 1H), 4.09 (ddd, J=29.4, 12.5, 0.8 Hz, 1H); $^{13}$C NMR (126 MHz, acetone-d$_6$) δ 144.1, 140.8, 123.8, 123.0, 118.3, 118.0, 102.5 (d, J=221.9 Hz), 65.2 (d, J=23.5 Hz); $^{19}$F NMR (282 MHz, acetone-d$_6$)–134.92 (ddd, J=54.5, 29.9, 5.2 Hz, 1F); MS (EI) m/z cal'd C$_8$H$_7$FO$_2$ [M]$^+$: 154.0, found 154.0.

Example 7.2.4—Compound 4

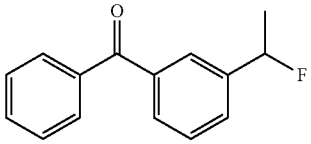 [SMILES: CC(F)c1cccc(C(=O)c2ccccc2)c1]

The reaction was performed according to general procedure in Example 7.1 above. The substrate (compound containing a carboxyl group) had the structure of compound 4, but with a —COOH in place of —F. In this case, the substrate was 2-(3-benzoylphenyl)propanoic acid. Purification by column chromatography (hexanes to 5% EtOAc/hexanes). $^1$H NMR (300 MHz, CDCl$_3$) δ 7.75-7.69 (m, 3H), 7.71-7.77 (m, 1H), 7.56-7.65 (m, 2H), 7.43-7.54 (m, 3H), 5.70 (dq, J=47.5, 6.4 Hz, 1H), 1.67 (dd, J=24.0, 6.5 Hz, 3H); $^{13}$C NMR (126 MHz, CDCl$_3$) δ 196.6, 142.0, 137.9, 137.4, 132.7, 130.2, 130.0, 129.2, 128.6, 128.4, 126.8, 90.6 (d, J=168.9 Hz), 23.1 (d, J=25.0 Hz); $^{19}$F NMR (282 MHz, CDCl$_3$) –168.57 (dq, J=47.7, 24.0 Hz); MS (EI) m/z cal'd C$_{15}$H$_{13}$FO [M]$^+$: 228.1, found 228.1.

Example 7.2.5—Compound 5

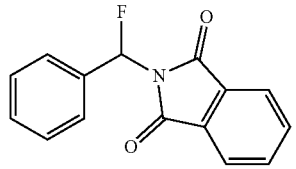 [SMILES: O=C1c2ccccc2C(=O)N1C(F)c1ccccc1]

The reaction was performed according to general procedure in Example 7.1 above. The substrate (compound containing a carboxyl group) had the structure of compound 5, but with a —COOH in place of —F. In this case, the substrate was 2-(1,3-dioxoisoindolin-2-yl)-2-phenylacetic acid. Purification by column chromatography (hexanes to 15% EtOAc/hexanes). $^1$H NMR (500 MHz, acetone-d$_6$) δ 7.92 (m, 4H), 7.56 (m, 2H), 7.35-7.46 (m, 3H), 7.25 (d, J=47.3 Hz, 1H); $^{13}$C NMR (126 MHz, acetone-d$_6$) δ 166.9, 136.2, 136.0, 132.5, 129.7, 129.1, 126.3, 124.6, 89.1 (d, J=202.4 Hz); $^{19}$F NMR (282 MHz, acetone-d$_6$)–156.40 ppm (d, J=47.1 Hz, 1F); MS (EI) m/z cal'd C$_{15}$H$_{10}$FNO$_2$ [M]$^+$: 255.1, found 255.1.

Example 7.2.6—Compound 6

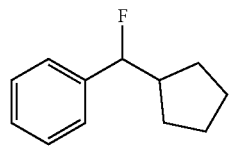 [SMILES: FC(c1ccccc1)C1CCCC1]

The reaction was performed according to general procedure in Example 7.1 above. The substrate (compound containing a carboxyl group) had the structure of compound 6, but with a —COOH in place of —F. In this case, the substrate was 2-cyclopentyl-2-phenylacetic acid. Purification by column chromatography (hexanes). $^1$H NMR (300 MHz, acetone-d$_6$) δ 7.30-7.42 (m, 5H), 5.22 (dd, J=47.8, 8.1 Hz, 1H), 2.42 (dt, J=16.1, 8.0 Hz, 1H), 1.79 (m, 1H), 1.32-1.72 (m, 6H), 1.24 (m, 1H); $^{13}$C NMR (126 MHz, acetone-d$_6$) δ 140.3, 128.3, 128.1, 126.2, 97.7 (d, J=170.6 Hz), 45.7, 28.3, 25.3; $^{19}$F NMR (282 MHz, acetone-d$_6$)–171.0 ppm (dd, J=47.7, 16.4 Hz, 1F); MS (EI) m/z cal'd C$_{12}$H$_{15}$F [M]$^+$: 178.1, found 178.1.

Example 7.2.7—Compound 7

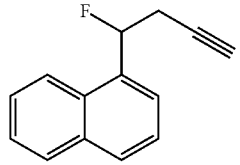

The reaction was performed according to general procedure in Example 7.1 above. The substrate (compound containing a carboxyl group) had the structure of compound 7, but with a —COOH in place of —F. In this case, the substrate was 2-(naphthalen-1-yl)pent-4-ynoic acid. Purification by column chromatography (hexanes to 2% EtOAc/hexanes). $^1$H NMR (300 MHz, CDCl$_3$) δ 8.01 (m, 1H), 7.87-7.94 (m, 2H), 7.67 (m, 1H), 7.50-7.60 (m, 3H), 6.35 (dt, J=46.3, 6.2 Hz, 1H), 3.08 (m, 1H), 3.01 (dd, J=6.1, 2.7 Hz, 1H), 2.12 (t, J=2.7 Hz, 1H); $^{13}$C NMR (126 MHz, Chloroform-d) δ 133.93, 133.67, 129.40, 129.09, 126.64, 125.90, 125.21, 123.56, 122.72, 90.04 (d, J=176.7 Hz), 79.25, 71.21, 34.18, 26.86, 22.41, 14.15; $^{19}$F NMR (282 MHz, CDCl$_3$)–174.2 (dt, J=46.4, 20.8 Hz, 1F); MS (EI) m/z cal'd C$_{14}$H$_{11}$F [M]$^+$: 198.1, found 198.1.

Example 7.2.8—Compound 8

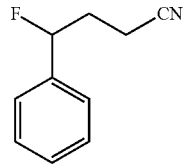 [SMILES: N#CCCC(F)c1ccccc1]

The reaction was performed according to general procedure in Example 7.1 above. The substrate (compound containing a carboxyl group) had the structure of compound 8, but with a —COOH in place of —F. In this case, the substrate was 4-cyano-2-phenylbutanoic acid. Purification by column chromatography (hexanes to 20% EtOAc/hexanes). $^1$H NMR (300 MHz, CDCl$_3$) δ 7.29-7.45 (m, 5H), 5.58 (ddd, J=47.6, 8.4, 4.1 Hz, 1H), 2.07-2.63 (m, 4H); $^{13}$C NMR (126 MHz, CDCl$_3$) δ 138.3, 129.1, 128.9, 125.4, 119.0, 92.2 (d, J=173.5 Hz), 33.0, 13.5; $^{19}$F NMR (282 MHz, CDCl$_3$) –179.5 (ddd, J=47.8, 28.5, 16.6 Hz); MS (EI) m/z cal'd C$_{10}$H$_{10}$FN [M]$^+$: 163.1, found 163.1.

Example 7.2.9—Compound 9

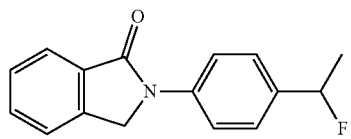 [SMILES: CC(F)c1ccc(N2Cc3ccccc3C2=O)cc1]

The reaction was performed according to general procedure in Example 7.1 above. The substrate (compound containing a carboxyl group) had the structure of compound 9, but with a —COOH in place of —F. In this case, the substrate was 2-(4-(1-oxoisoindolin-2-yl)phenyl)propanoic acid. Purification by column chromatography (hexanes to 20% EtOAc/hexanes). $^1$H NMR (300 MHz, acetone-$d_6$) δ 8.02 (m, 2H), 7.80 (m, 1H), 7.66 (m, 2H), 7.54 (m, 1H), 7.46 (m, 2H), 5.67 (dd, J=47.8, 6.4 Hz, 1H), 5.01 (s, 2H), 1.62 (dd, J=23.6, 6.4 Hz, 3H); $^{13}$C NMR (126 MHz, acetone-$d_6$) δ 167.8, 142.0, 141.0, 137.9, 134.0, 133.1, 129.1, 127.0, 124.2, 119.7, 91.2 (d, J=165.6 Hz), 51.2, 23.1; $^{19}$F NMR (282 MHz, acetone-$d_6$) −163.50 ppm (dq, J=47.2, 23.6 Hz, 1F); MS (EI) m/z cal'd $C_{16}H_{14}FNO$ [M-HF]$^+$: 255.1, found. 255.1.

Example 7.2.10—Compound 10

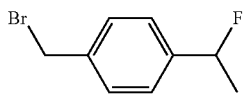

The reaction was performed according to general procedure in Example 7.1 above. The substrate (compound containing a carboxyl group) had the structure of compound 10, but with a —COOH in place of —F. In this case, the substrate was 2-(4-(bromomethyl)phenyl)propanoic. Purification by column chromatography (hexanes). $^1$H NMR (300 MHz, CDCl$_3$) δ 7.41 (d, J=8.1 Hz, 2H), 7.33 (m, 2H), 5.62 (dq, J=47.6, 6.4 Hz, 1H), 4.50 (s, 2H), 1.64 (dd, J=23.9, 6.4 Hz, 3H); $^{13}$C NMR (75 MHz, CDCl$_3$) δ 141.9, 137.8, 129.3, 126.8, 125.8, 90.7 (d, J=168.2 Hz), 33.1, 23.0 (d, J=25.1 Hz); $^{19}$F NMR (282 MHz, CDCl$_3$) −168.0 (dq, J=47.7, 23.9 Hz, 1F); MS (EI) m/z cal'd $C_9H_{10}BrF$ [M]$^+$: 216.0, found 216.0.

Example 7.2.11—Compound 11

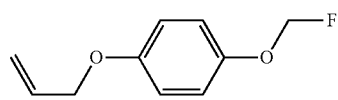

The reaction was performed according to general procedure in Example 7.1 above. The substrate (compound containing a carboxyl group) had the structure of compound 11, but with a —COOH in place of —F. In this case, the substrate was 2-(4-(allyloxy)phenoxy)acetic acid. Purification by column chromatography (hexanes to 4% EtOAc/hexanes). $^1$H NMR (500 MHz, acetone-$d_6$) δ7.09-6.99 (m, 2H), 6.98-6.89 (m, 2H), 6.05 (ddt, J=17.2, 10.5, 5.2 Hz, 1H), 5.73 (d, J=55.9 Hz, 2H), 5.39 (dq, J=17.3, 1.7 Hz, 1H), 5.23 (dq, J=10.5, 1.5 Hz, 1H), 4.53 (dt, J=5.3, 1.6 Hz, 2H); $^{13}$C NMR (126 MHz, acetone-$d_6$) δ 155.7, 151.8, 134.8, 118.7, 117.4, 116.4, 102.6 (d, J=215.3 Hz), 69.7; $^{19}$F NMR (282 MHz, acetone-$d_6$)−149.68 ppm (t, J=56.0 Hz, 1F); MS (EI) m/z cal'd $C_{10}H_{11}FO_2$ [M]$^+$: 182.1, found 182.1.

Example 7.2.12—Compound 12

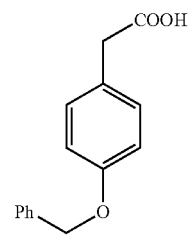 [SMILES: O=C(O)Cc1ccc(OCc2ccccc2)cc1]

The reaction was performed according to general procedure in Example 7.1 above. The substrate (compound containing a carboxyl group) had the structure of compound 12, but with a —COOH in place of —F. In this case, the substrate was 2-(4-(benzyloxy)phenyl)acetic acid. Purification by flash chromatography (hexanes to 6% EtOAc/hexanes). $^1$H NMR (500 MHz, acetone-$d_6$) δ 5.14 (s, 2H), 5.30 (d, J=48.8 Hz, 2H), 7.05 (m, 2H), 7.33 (m, 1H), 7.35-7.44 (m, 4H), 7.48 (m, 2H); $^{13}$C NMR (126 MHz, acetone-$d_6$) δ 70.4, 85.0 (d, J=162.4 Hz), 115.7, 128.5, 128.7, 129.3, 129.7, 131.0, 138.2, 160.3; $^{19}$F NMR (282 MHz, acetone-$d_6$)−199.28 ppm (t, J=48.8 Hz, 1F); MS (EI) m/z cal'd $C_{14}H_{13}FO$ [M]$^+$: 216.1, found 216.1.

Example 7.2.13—Compound 13

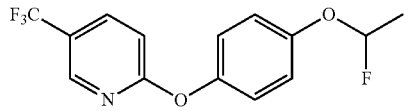 [SMILES: CC(F)Oc1ccc(Oc2ccc(C(F)(F)F)cn2)cc1]

The reaction was performed according to general procedure in Example 7.1 above. The substrate (compound containing a carboxyl group) had the structure of compound 13, but with a —COOH in place of —F. In this case, the substrate was 2-(4-(5-(trifluoromethyl)pyridin-2-yloxy)phenoxy)propanoic acid. Purification by column chromatography (hexanes to 15% EtOAc/hexanes). $^1$H NMR (300 MHz, acetone-$d_6$) δ 1.63 (dd, J=19.9, 4.8 Hz, 3H), 6.13 (dq, J=62.9, 4.8 Hz, 1H), 6.95-7.49 (m, 5H), 8.14 (dd, J=8.7, 2.6 Hz, 1H), 8.45 (m, 1H); $^{13}$C NMR (126 MHz, acetone-$d_6$) δ 21.4 (d, J=24.9 Hz), 109.0 (d, J=215.3 Hz), 112.5, 118.8, 123.7, 138.0, 146.1, 149.6, 154.6, 167.1; $^{19}$F NMR (282 MHz, acetone-$d_6$) −115.35 ppm (dq, J=62.7, 19.8 Hz), −60.65 (s, 3F); MS (EI) m/z cal'd $C_{14}H_{11}F_4NO_2$ [M]$^+$: 301.1, found 301.1.

Example 7.2.14—Compound 14

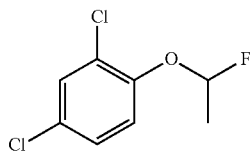

The reaction was performed according to general procedure in Example 7.1 above. The substrate (compound containing a carboxyl group) had the structure of compound 14, but with a —COOH in place of —F. In this case, the substrate was 2-(2,4-dichlorophenoxy)propanoic acid. Purification by column chromatography (hexanes to 2% EtOAc/hexanes). $^1$H NMR (300 MHz, CDCl$_3$) δ 1.72 (dd, J=20.0, 4.9 Hz, 3H), 5.84 (dd, J=62.2, 4.9 Hz, 1H), 7.11-7.25 (m, 2H), 7.40 (dd, J=2.4, 0.4 Hz, 1H); $^{13}$C NMR (75 MHz, CDCl$_3$) δ 21.0 (d, J=24.6 Hz), 109.0 (d, J=220.3 Hz), 119.8, 128.0, 130.3; $^{19}$F NMR (282 MHz, CDCl$_3$) −116.52 (dq, J=62.0, 20.1 Hz, 1F); MS (EI) m/z cal'd C$_8$H$_7$Cl$_2$FO [M]$^+$: 208.0, found 208.0.

Example 7.2.15—Compound 15

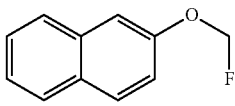 [SMILES: FCOc1ccc2ccccc2c1]

The reaction was performed according to general procedure in Example 7.1 above. The substrate (compound containing a carboxyl group) had the structure of compound 15, but with a —COOH in place of —F. In this case, the substrate was 2-(naphthalen-2-yloxy)acetic acid. Purification by column chromatography (hexanes to 1% EtOAc/hexanes). $^1$H NMR (300 MHz, Chloroform-d) δ 7.77-7.64 (m, 3H), 7.45-7.26 (m, 3H), 7.16 (dd, J=8.9, 2.4 Hz, 1H), 5.73 (d, J=54.6 Hz, 2H); $^{13}$C NMR (126 MHz, Chloroform-d) δ 154.61, 134.20, 130.25, 129.82, 127.73, 127.31, 126.69, 124.82, 118.56, 111.08, 100.88 (d, J=218.6 Hz); $^{19}$F NMR (282 MHz, CDCl$_3$)−149.0 (t, J=54.5 Hz)$^{19}$F NMR (282 MHz, Chloroform-d) δ −148.80 (t, J=54.4 Hz); MS (EI) m/z cal'd C$_{11}$H$_9$FO [M]$^+$: 176.1, found 176.1.

Example 7.2.16—Compound 16

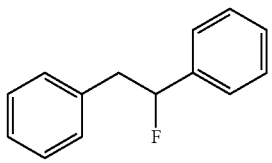 [SMILES: FC(Cc1ccccc1)c1ccccc1]

The reaction was performed according to general procedure in Example 7.1 above. The substrate (compound containing a carboxyl group) had the structure of compound 16, but with a —COOH in place of —F. In this case, the substrate was 2,3-diphenylpropanoic acid. Purification by column chromatography (hexanes). $^1$H NMR (300 MHz, CDCl$_3$) δ 2.76-3.57 (m, 2H), 5.64 (ddd, J=47.3, 8.1, 4.9 Hz, 1H), 7.63-6.98 (m, 10H); $^{13}$C NMR (75 MHz, CDCl$_3$) δ 44.1 (d, J=24.3 Hz), 95.0 (d, J=174.3 Hz), 125.8, 126.8, 128.5, 129.6, 136.8, 139.8; $^{19}$F NMR (282 MHz, CDCl$_3$)−173.18 (ddd, J=47.0, 28.8, 17.7 Hz); MS (EI) m/z cal'd C$_{14}$H$_{13}$F [M]$^+$: 200.1, found 200.1.

Example 7.2.17—Compound 17

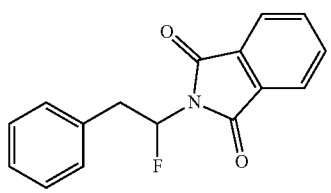 [SMILES: O=C1c2ccccc2C(=O)N1C(F)Cc1ccccc1]

The reaction was performed according to general procedure in Example 7.1 above. The substrate (compound containing a carboxyl group) had the structure of compound 17, but with a —COOH in place of —F. In this case, the substrate was 2-(1,3-dioxoisoindolin-2-yl)-3-phenylpropanoic acid. Purification by column chromatography (hexanes to 20% EtOAc/hexanes). $^1$H NMR (300 MHz, Chloroform-d) δ 7.91 (dd, J=5.5, 3.1 Hz, 2H), 7.79 (dd, J=5.5, 3.0 Hz, 2H), 7.36-7.19 (m, 5H), 6.39 (dt, J=47.6, 7.2 Hz, 1H), 4.02-3.57 (m, 2H); $^{13}$C NMR (126 MHz, Chloroform-d) δ 166.85, 134.71, 131.39, 129.24, 128.78, 127.24, 123.95, 90.34 (d, J=204.4 Hz), 37.50; $^{19}$F NMR (282 MHz, Chloroform-d) δ−144.87 (ddd, J=47.5, 19.6, 9.3 Hz); MS (EI) m/z cal'd C$_{16}$H$_{12}$FNO$_2$ [M]$^+$: 269.1, found 269.1.

Example 7.2.18—Compound 18

The reaction was performed according to general procedure in Example 7.1 above. The substrate (compound containing a carboxyl group) had the structure of compound 18, but with a —COOH in place of —F. In this case, the substrate was 2-phenylbutanoic acid. Purification by column chromatography (hexanes). $^1$H NMR (300 MHz, Chloroform-d) δ 7.47-7.28 (m, 5H), 5.36 (ddd, J=47.7, 7.6, 5.3 Hz, 1H), 2.17-1.67 (m, 2H), 0.99 (t, J=7.4 Hz, 3H); $^{13}$C NMR (126 MHz, Chloroform-d) δ 140.35 (d, J=19.9 Hz), 128.57, 128.35, 125.79, 96.01 (d, J=170.6 Hz), 30.41, 9.62; $^{19}$F NMR (282 MHz, Chloroform-d) δ −175.58 (ddd, J=47.9, 26.6, 17.9 Hz); MS (EI) m/z cal'd C$_9$H$_{11}$F [M]$^+$: 138.1, found 138.1.

Example 7.2.19—Compound 19

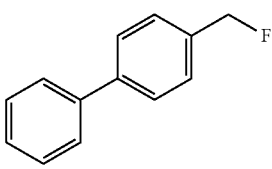 [SMILES: FCc1ccc(-c2ccccc2)cc1]

The reaction was performed according to general procedure in Example 7.1 above. The substrate (compound containing a carboxyl group) had the structure of compound 19, but with a —COOH in place of —F. In this case, the substrate was 2-(biphenyl-4-yl)acetic acid. Purification by column chromatography (hexanes). $^1$H NMR (300 MHz, Chloroform-d) δ 7.61 (td, J=7.9, 1.3 Hz, 4H), 7.49-7.42 (m, 4H), 7.40-7.31 (m, 1H), 5.42 (d, J=47.9 Hz, 2H); $^{13}$C NMR (126 MHz, Chloroform-d) δ 141.94, 140.79, 135.31, 129.04 128.28, 127.74, 127.57, 127.36, 84.62 (d, J=165.9 Hz); $^{19}$F NMR (282 MHz, Chloroform-d) δ−206.20 (t, J=47.9 Hz); MS (EI) m/z cal'd $C_{13}H_{11}F$ [M]$^+$: 186.1, found 186.1.

Example 7.2.20—Compound 20

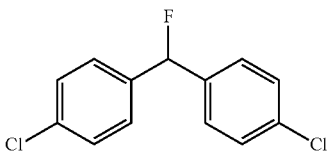 [SMILES: FC(c1ccc(Cl)cc1)c1ccc(Cl)cc1]

The reaction was performed according to general procedure in Example 7.1 above. The substrate (compound containing a carboxyl group) had the structure of compound 20, but with a —COOH in place of —F. In this case, the substrate was 2,2-bis(4-chlorophenyl)acetic acid. Purification by column chromatography (hexanes). $^1$H NMR (300 MHz, acetone-d$_6$) δ 6.65 (d, J=46.7 Hz, 1H), 7.36-7.50 (m, 8H); $^{13}$C NMR (126 MHz, acetone-d$_6$) δ 93.7 (d, J=172.2 Hz), 129.0, 129.6, 134.8, 139.7; $^{19}$F NMR (282 MHz, acetone-d$_6$)−167.28 ppm (d, J=46.7 Hz, 1F); MS (EI) m/z cal'd $C_{13}H_9Cl_2F$ [M]$^+$: 254.0, found 254.0.

Example 7.2.21—Compound 21

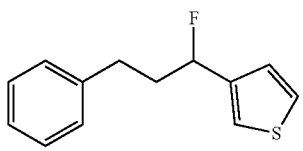 [SMILES: FC(CCc1ccccc1)c1ccsc1]

The reaction was performed according to general procedure in Example 7.1 above. The substrate (compound containing a carboxyl group) had the structure of compound 21, but with a —COOH in place of —F. In this case, the substrate was 4-phenyl-2-(thiophen-3-yl)butanoic acid. Purification by column chromatography (hexanes to 2% EtOAc/hexanes). $^1$H NMR (300 MHz, CDCl$_3$) δ 2.0-2.4 (m, 2H), 2.74 (m, 2H); 5.44 (ddd, J=48.3, 8.6, 4.4 Hz, 1H), 7.02 (m, 1H), 7.12-7.28 (m, 7H); $^{13}$C NMR (126 MHz, CDCl$_3$) δ 31.3 (d, J=4.2 Hz), 38.0 (d, J=23.3 Hz), 89.9 (d, J=168.3 Hz), 122.4, 122.5, 125.4, 126.2, 126.5, 128.5, 141.0, 141.2, 141.4; $^{19}$F NMR (282 MHz, CDCl$_3$)−169.70 (ddd, J=48.7, 28.3, 15.5 Hz, 1F); MS (EI) m/z cal'd $C_{13}H_{13}FS$ [M]$^+$: 220.1, found 200.1.

Example 7.2.22—Compound 22

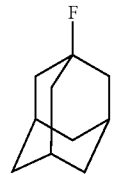

The reaction was performed according to general procedure in Example 7.1 above. The substrate (compound containing a carboxyl group) had the structure of compound 22, but with a —COOH in place of —F. In this case, the substrate was 1-adamantanecarboxylic acid. Purification by column chromatography (pentane). $^1$H NMR (300 MHz, CDCl$_3$) δ 1.60-1.74 (br, 6H), 1.81-2.03 (m, 6H), 2.15-2.48 (br, 3H); $^{13}$C NMR (126 MHz, CDCl$_3$) δ 31.6 (d, J=9.7 Hz), 36.0 (d, J=2.1 Hz), 42.8 (d, J=17.0 Hz), 92.8 (d, J=183.1 Hz); $^{19}$F NMR (282 MHz, CDCl$_3$) −128.5 ppm (t, J=54.3 Hz, 1F); MS (EI) m/z cal'd $C_{10}H_{15}F$ [M]$^+$: 154.1, found 154.1.

Example 7.2.23—Compound 26

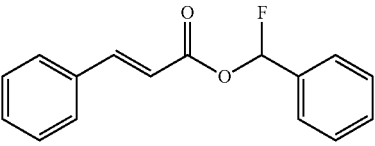 [SMILES: O=C(/C=C/c1ccccc1)OC(F)c1ccccc1]

The reaction was performed according to general procedure in Example 7.1 above. The substrate (compound containing a carboxyl group) had the structure of compound 26, but with a —COOH in place of —F. In this case, the substrate was (E)-2-(cinnamoyloxy)-2-phenylacetic acid. Purification by column chromatography (hexanes to 10% EtOAc/hexanes). $^1$H NMR (500 MHz, acetone-d$_6$) δ 6.70 (d, J=16.0 Hz, 1H), 7.38 (d, J=55.9 Hz, 1H), 7.46 (m, 3H), 7.51 (m, 3H), 7.67 (ddd, J=6.1, 2.7, 1.2 Hz, 2H), 7.75 (m, 2H), 7.89 (d, J=16.0 Hz, 1H); $^{13}$C NMR (126 MHz, acetone-d$_6$) δ 102.6 (d, J=218.7 Hz), 117.4, 127.2, 129.5, 129.7, 129.9, 131.1, 131.9, 135.0, 136.0, 148.1, 165.1; $^{19}$F NMR (282 MHz, acetone-d$_6$) −120.91 ppm (d, J=55.7 Hz, 1F); MS (EI) m/z cal'd $C_{16}H_{13}FO_2$[M]$^+$: 256.1, found 256.1.

Example 7.2.24—Compound 27

The reaction was performed according to general procedure in Example 7.1 above. The substrate (compound containing a carboxyl group) had the structure of compound 27, but with a —COOH in place of —F. In this case, the substrate was 2-((8R,9S,13S, 14S)-13-methyl-17-oxo-7,8,9, 11,12,13,14,15,16,17-decahydro-6H-cyclopenta[α] phenanthren-3-yloxy)propanoic acid. Purification by flash chromatography (hexanes to 20% EtOAc/hexanes). $^1$H NMR (500 MHz, acetone-d$_6$) (~1:1 mixture of diastereomers) δ 0.86 (s, 3H), 1.29-1.71 (m, 10H), 1.81 (m, 1H), 2.01 (m, 2H), 2.21 (m, 1H), 2.38 (m, 2H), 2.84 (m, 2H), 6.03 (dqd, J=63.1, 4.9, 2.5 Hz, 1H), 6.76 (t, J=2.3 Hz, 1H), 6.81 (dt, J=8.5, 2.3 Hz, 1H), 7.22 (dd, J=8.9, 1.1 Hz, 1H); $^{13}$C NMR (126 MHz, acetone-d$_6$) δ 14.1, 21.4 (dd, J=25.3, 1.4 Hz), 22.1, 26.6, 27.1, 30.2, 32.5, 36.0, 39.0, 44.8, 48.4, 51.0, 108.6 (dd, J=214.7, 9.1 Hz), 115.0, 117.7, 127.3, 135.5, 138.8, 155.3, 219.4; $^{19}$F NMR (282 MHz, acetone-d$_6$)– 114.21 ppm (dqd, J=63.1, 19.7, 13.3 Hz); HRMS (ESI) m/z cal'd C$_{20}$H$_{25}$FNaO$_2$[M+Na]$^+$: 339.1736, found 339.1728.

Example 7.2.25—Compound 28

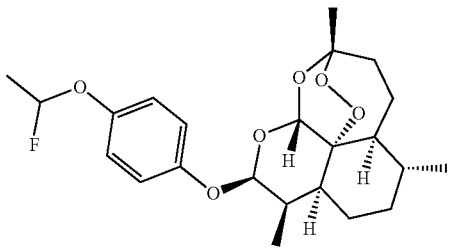

The reaction was performed according to general procedure in Example 7.1 above. The substrate (compound containing a carboxyl group) had the structure of compound 28, but with a —COOH in place of —F. In this case, the substrate was 2-[4-[[(3R,5aS,6R,8aS,9R,10S, 12R, 12aR)-decahydro-3,6,9-trimethyl-3,12-epoxy-12H-pyrano[4,3-j]-1,2-benzodioxepin-10-yl]oxy]phenoxy]propanoic acid. Purification by flash chromatography (hexanes to 20% EtOAc/hexanes). $^1$H NMR (500 MHz, acetone-d$_6$) (~1:1 mixture of diastereomers) δ 1.00 (d, J=6.4 Hz, 3H), 1.01-1.05 (m, 1H), 1.09 (d, J=7.4 Hz, 3H), 1.18-1.32 (m, 1H), 1.35 (s, 3H), 1.39-1.59 (m, 3H), 1.64 (dd, J=19.8, 4.8 Hz, 3H), 1.74 (m, 1H), 1.93 (m, 2H), 2.01-2.08 (m, 2H), 2.33 (ddd, J=14.6, 13.5, 4.0 Hz, 1H), 2.73 (m, 1H), 5.47 (dd, J=4.0, 3.0 Hz, 1H), 5.55 (d, J=1.5 Hz, 1H), 6.06 (ddd, J=63.3, 5.0, 3.9 Hz, 1H), 7.04-7.23 (m, 4H); $^{13}$C NMR (126 MHz, acetone-d$_6$) δ 13.2, 20.7, 21.4 (d, J=25.1 Hz), 25.2, 25.4, 26.1, 31.8, 35.4, 37.0, 38.0, 45.3, 53.5, 81.4, 88.8, 101.7, 104.6, 109.4 (dd, J=214.9, 7.0 Hz), 119.0, 152.3, 154.4; $^{19}$F NMR (282 MHz, acetone-d$_6$)–114.57 ppm (dp, J=63.5, 19.9 Hz); HRMS (ESI) m/z cal'd C$_{23}$H$_{31}$FKO$_6$[M+K]$^+$: 461.1742, found 461.1735.

Example 7.3—Radiochemistry

Example 7.3.1—General Methods

No-carrier-added [$^{18}$F]fluoride was produced from water 97% enriched in $^{18}$O (ISOFLEX, USA) by the nuclear reaction $^{18}$O(p,n)$^{18}$F using a Siemens Eclipse HP cyclotron and a silver-bodied target at Massachusetts General Hospital Athinoula A. Martinos Center for Biomedical Imaging. The produced [$^{18}$F]fluoride in water was transferred from the cyclotron target by helium push.

Example 73.2 Procedure for Decarboxylative $^{18}$F Labeling of Carboxylic Acids A 4 mL vial with a screw cap was charged with substrate (0.22 mmol), iodosylbenzene (0.068 mmol) and a stir bar (2×5 mm). A portion of aqueous [$^{18}$F]fluoride solution (40-50 μL, 4-5 mCi) obtained from the cyclotron was loaded on to an Chromafix PS-HCO$_3$ IEX cartridge, which had been previously washed with 5.0 mg/mL K$_2$CO$_3$ in Milli-Q water followed by 5 mL of Milli-Q water. Then, the cartridge loaded with [$^{18}$F]fluoride was washed with 2 mL Milli-Q water and [$^{18}$F]fluoride was released from the cartridge using 0.8 mL 5.0 mg/mL K$_2$CO$_3$ in Milli-Q water. A portion of the resulting [$^{18}$F]fluoride solution (25 μL, 125-150 μCi) was diluted with 3.0 mL acetonitrile. 0.6 mL of this [$^{18}$F] fluoride acetonitrile solution was added to the vial containing the substrate and the oxidant. The resulting mixture was stirred for 2 min under 50° C. (for most of the cases, PhIO solid will dissolve during the stirring). Then 2 mg Mn(TMP) Cl catalyst (0.0023 mmol) was added in solid form to the reaction mixture. The vial was recapped and stirred at 50° C. for 10 more min. After 10 min, an aliquot of the reaction mixture was taken and spotted on a silica gel TLC plate. The plate was developed in an appropriate eluent and scanned with a Bioscan AR-2000 Radio TLC Imaging Scanner.

Example 7.3.3—Example of Radio-TLC Scans

Figure 15A:
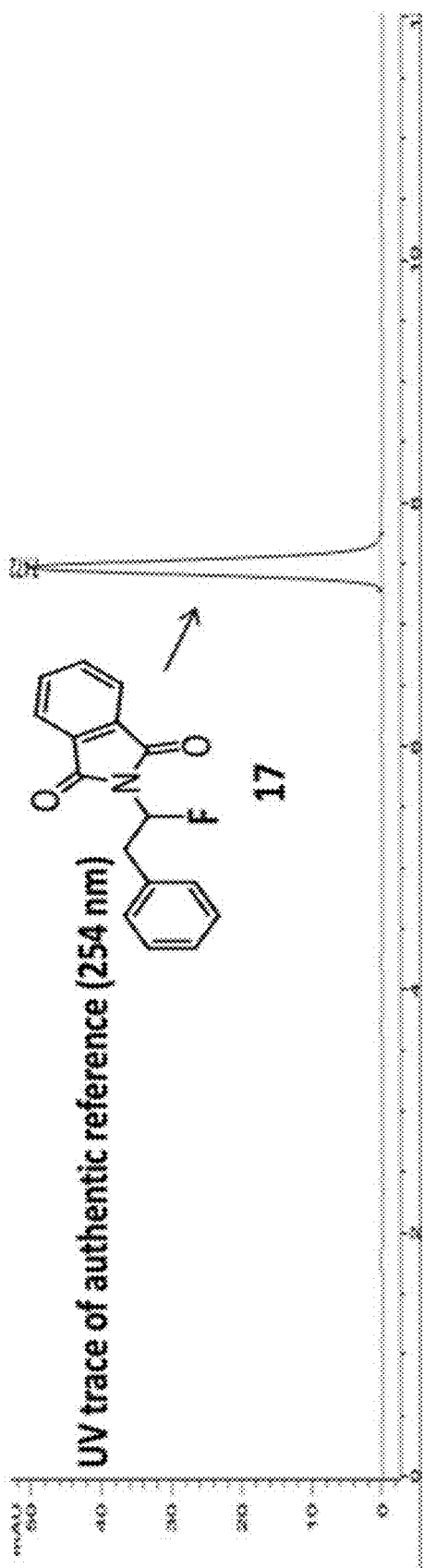
FIGS. 15A-15C illustrate the UV trace of the authentic reference of compound F-17, the radio-HPLC trace of the reaction mixture to produce compound ¹⁸F-17, and the UV trace for the reaction mixture.
Figure 15B:
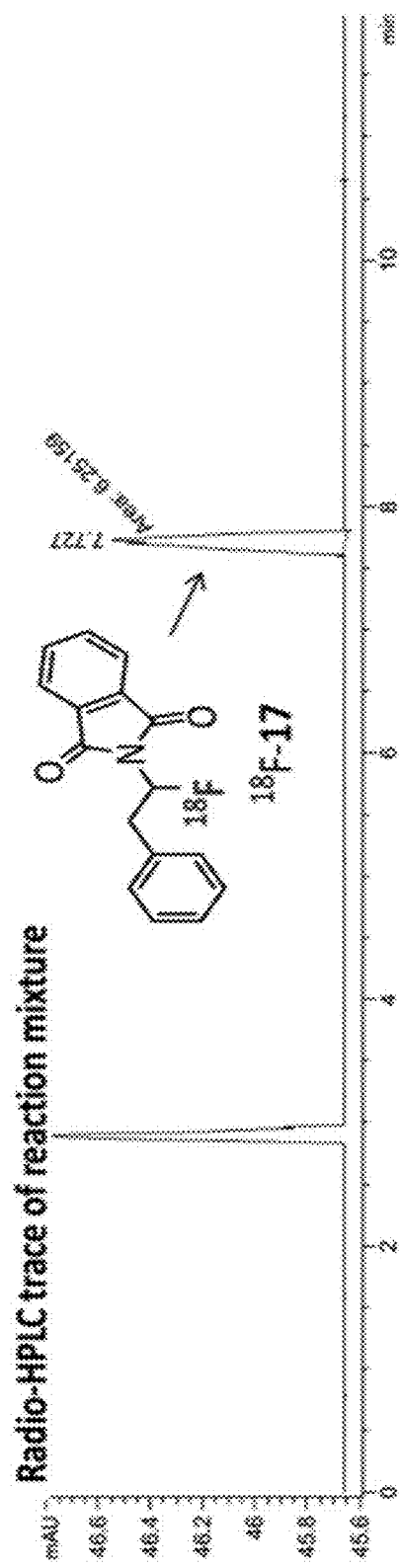
Figure 15C:
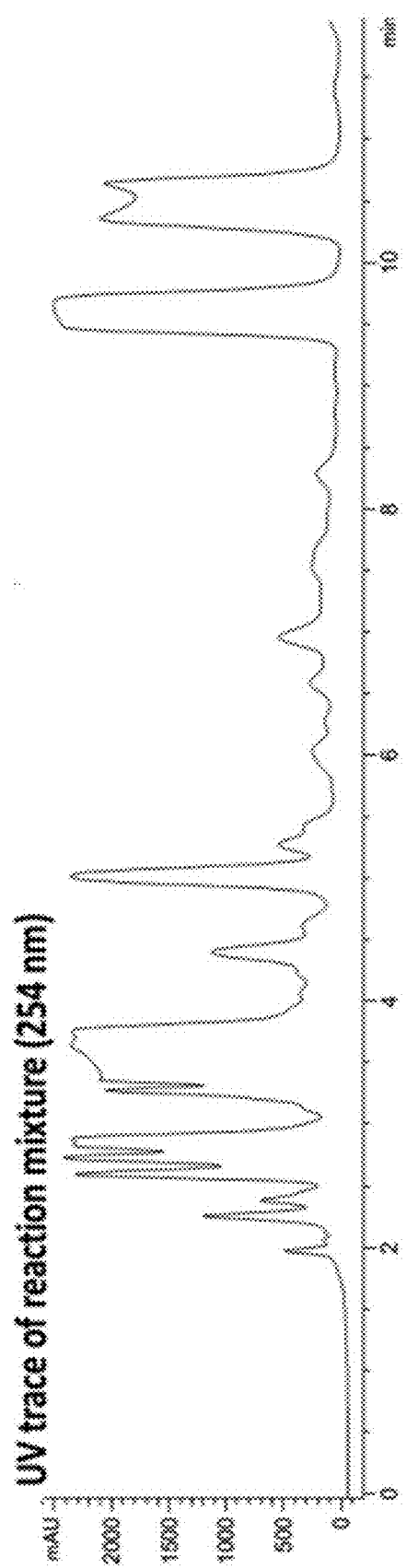
Figure 16A:
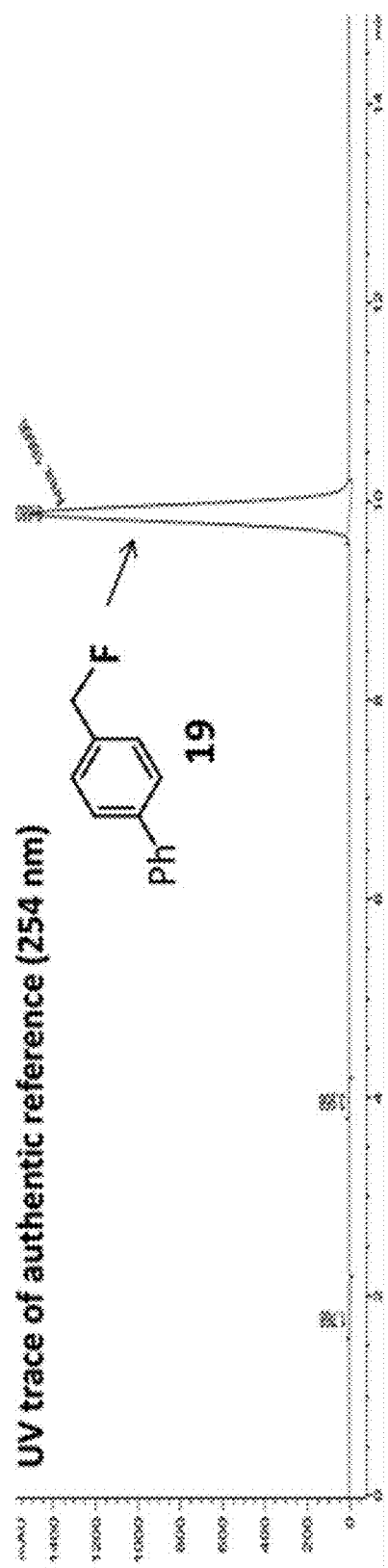
FIGS. 16A-16C, 17A-17C, 18A-18C, 19A-19C, 20A-20C and FIGS. 21A-21C illustrate the same traces as FIGS. 17A-17C but for compounds 19, 8, 14, 15, 5, and 18, respectively.
Figure 16B:
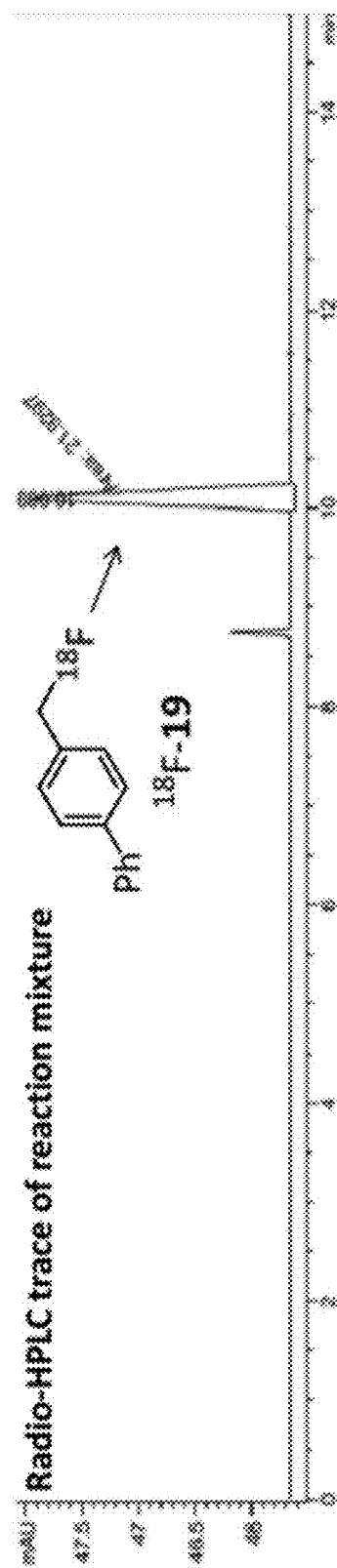
Figure 16C:
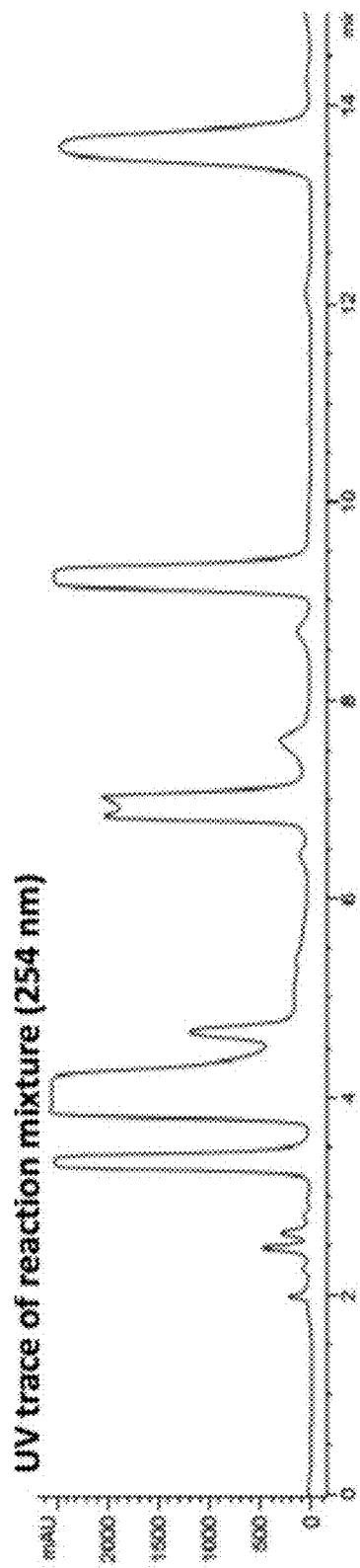
Figure 17A:
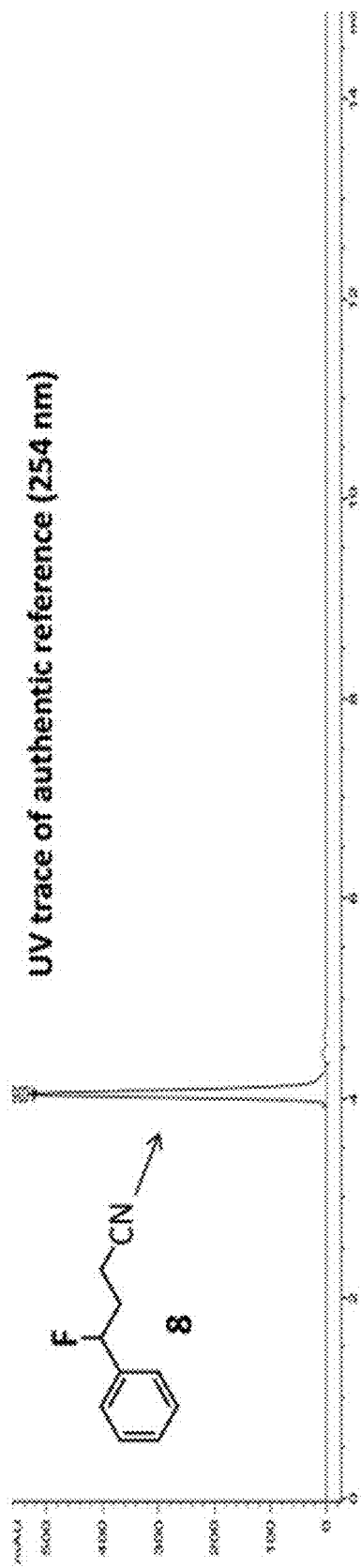
Figure 17B:
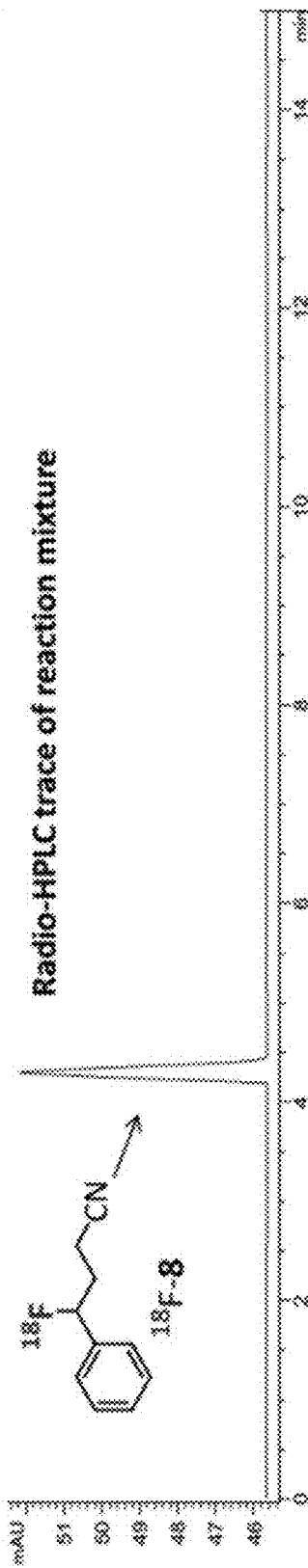
Figure 17C:
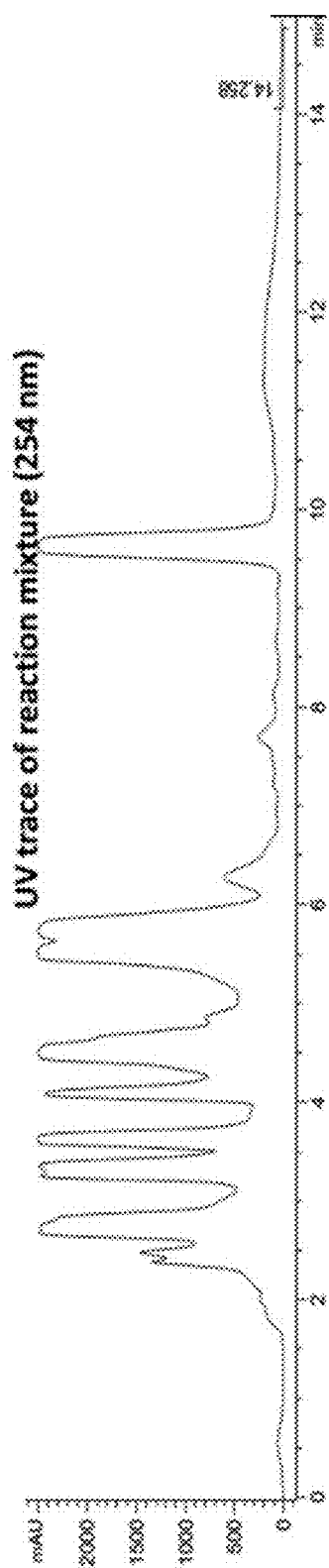
Figure 18A:
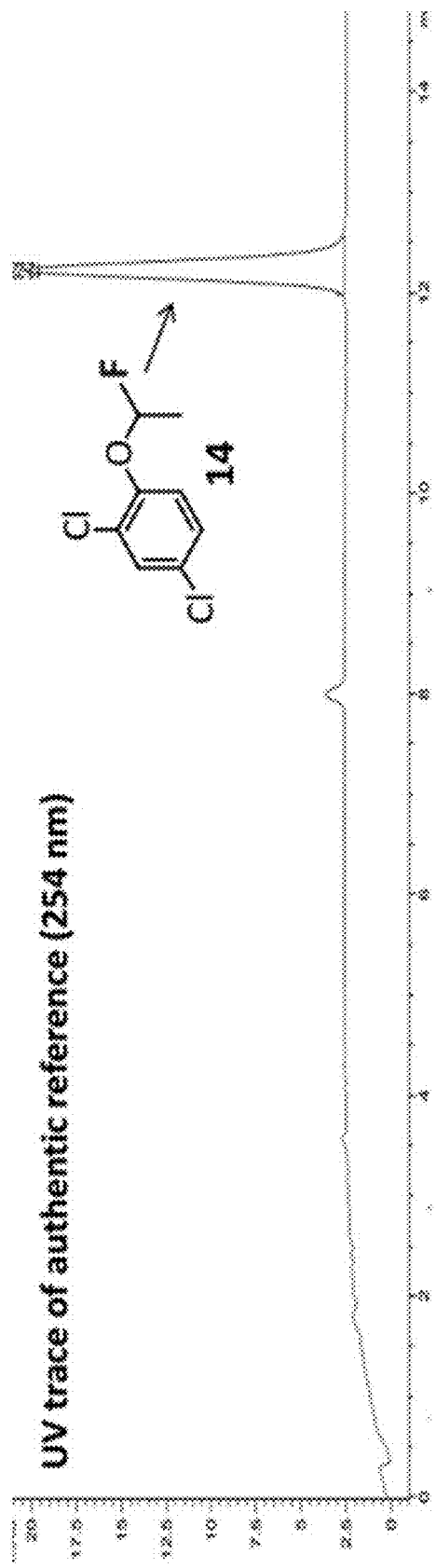
Figure 18B:
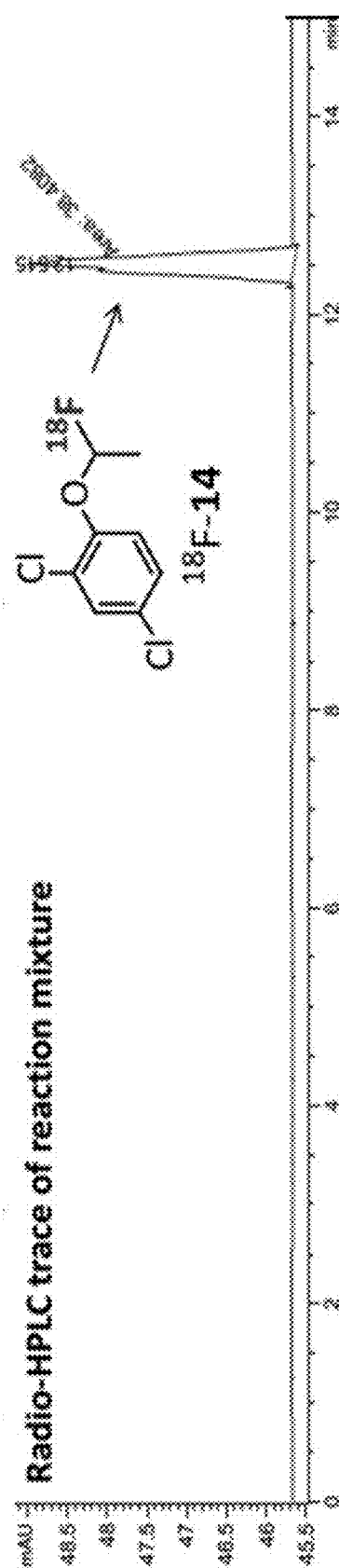
Figure 18C:
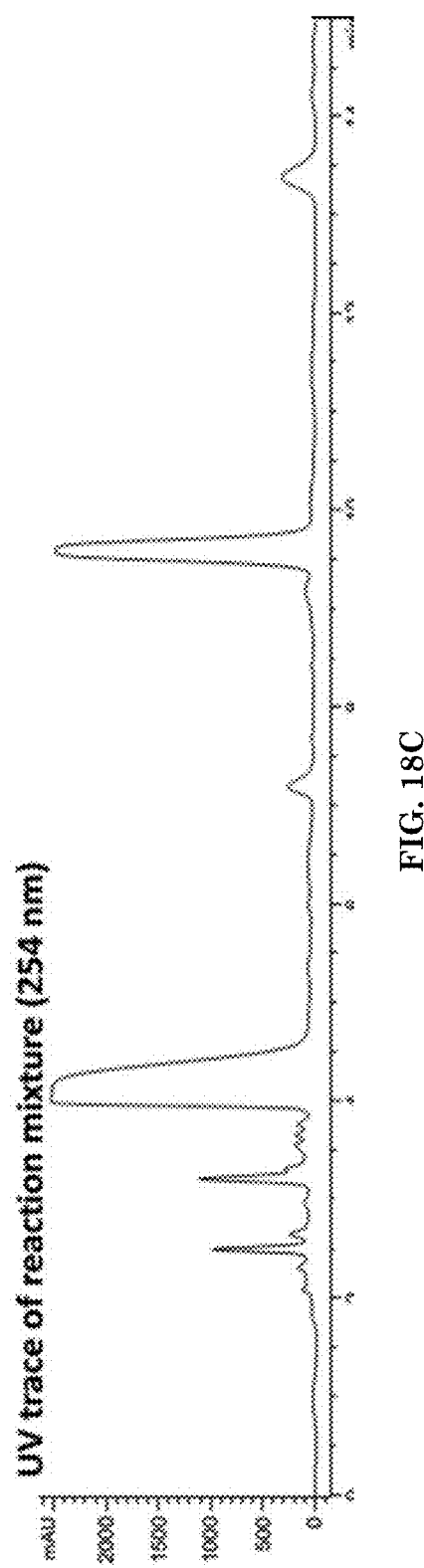
Figure 19A:
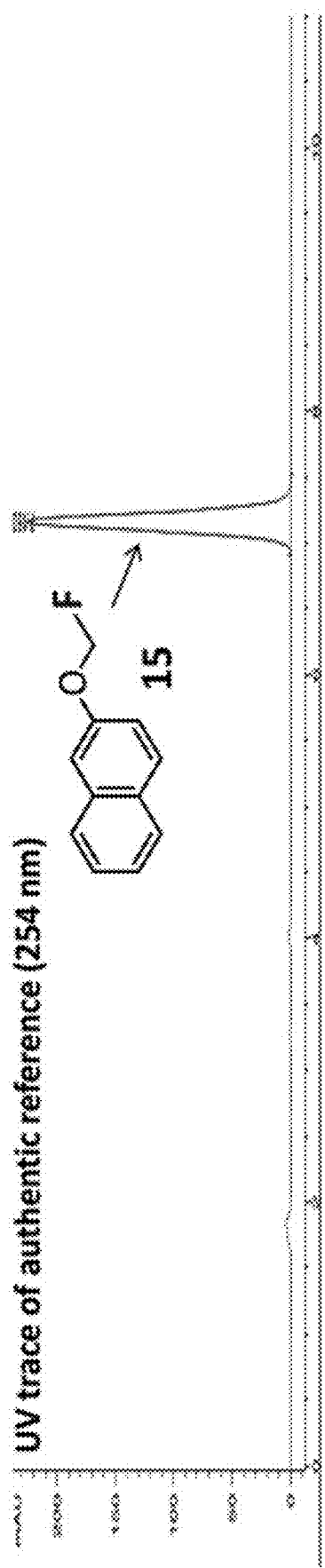
Figure 19B:
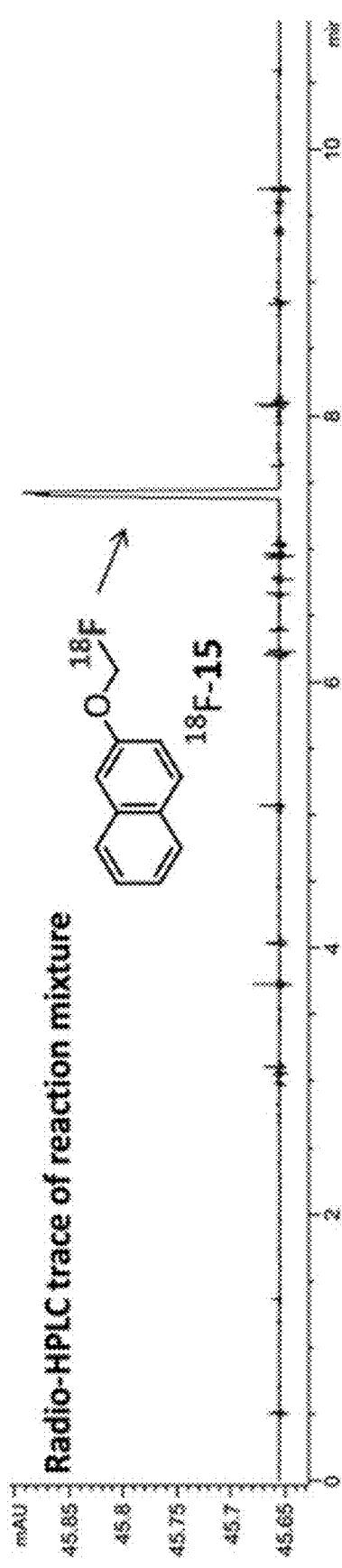
Figure 19C:
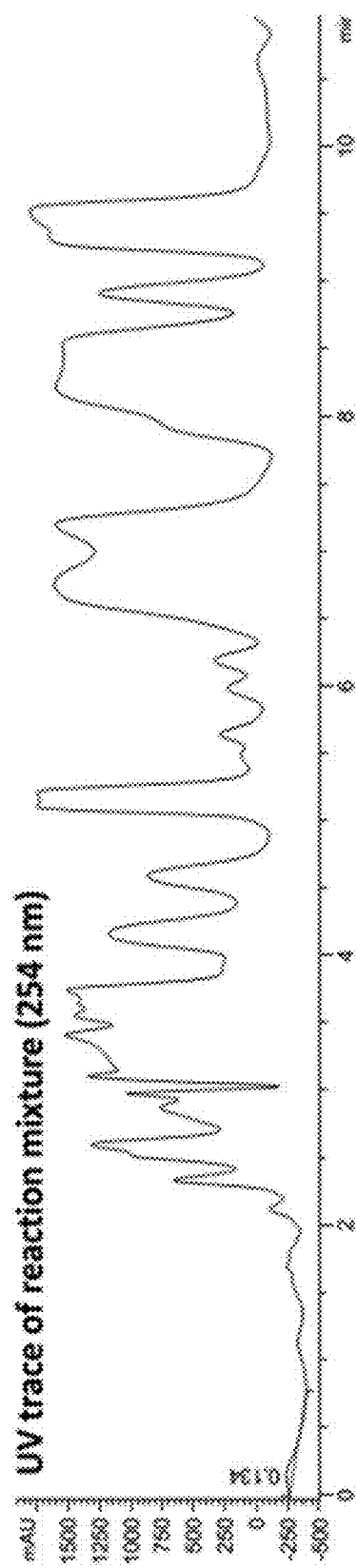
Figure 20A:
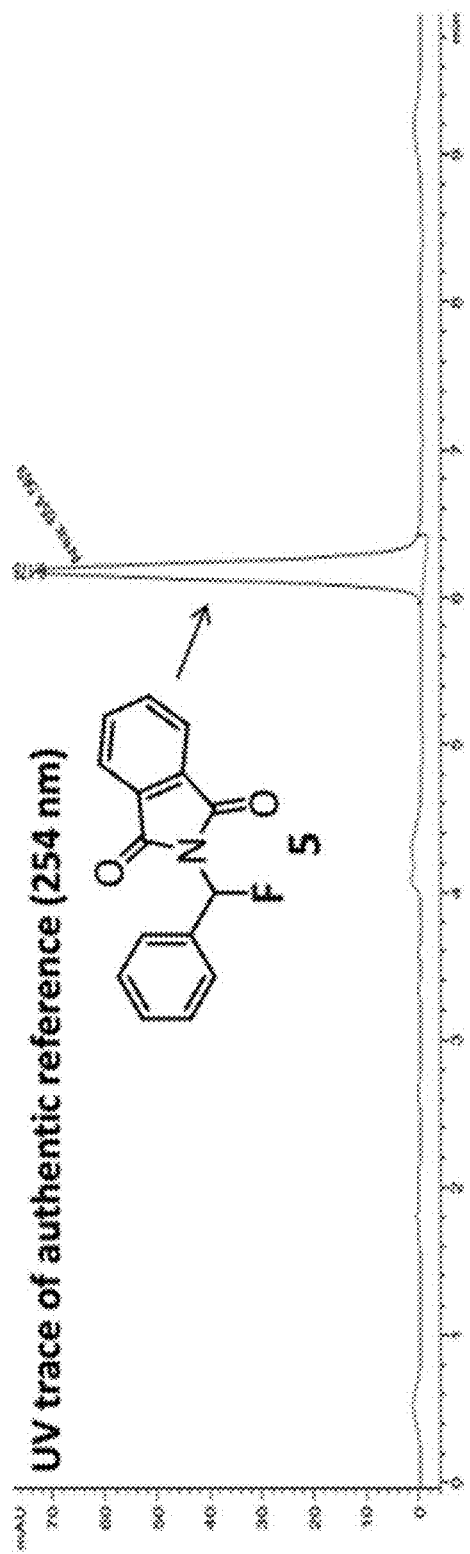
Figure 20B:
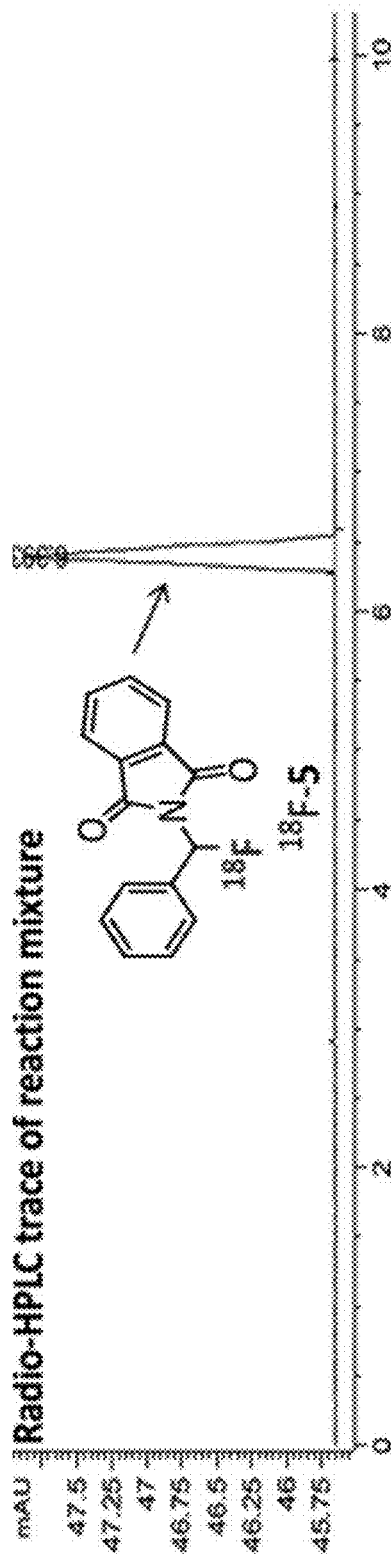
Figure 20C:
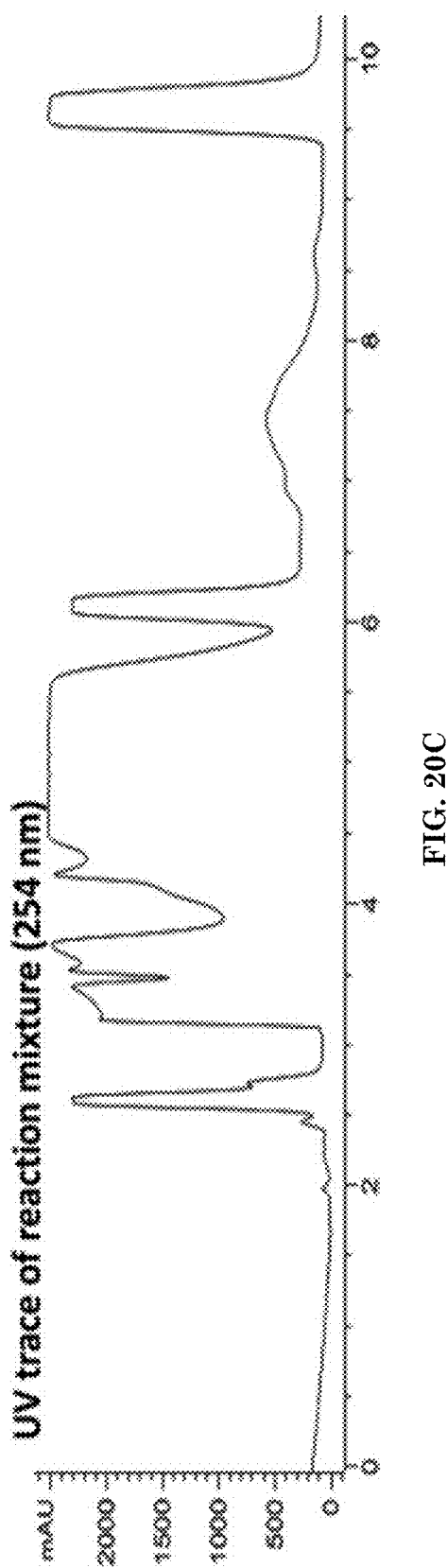
Figure 21A:
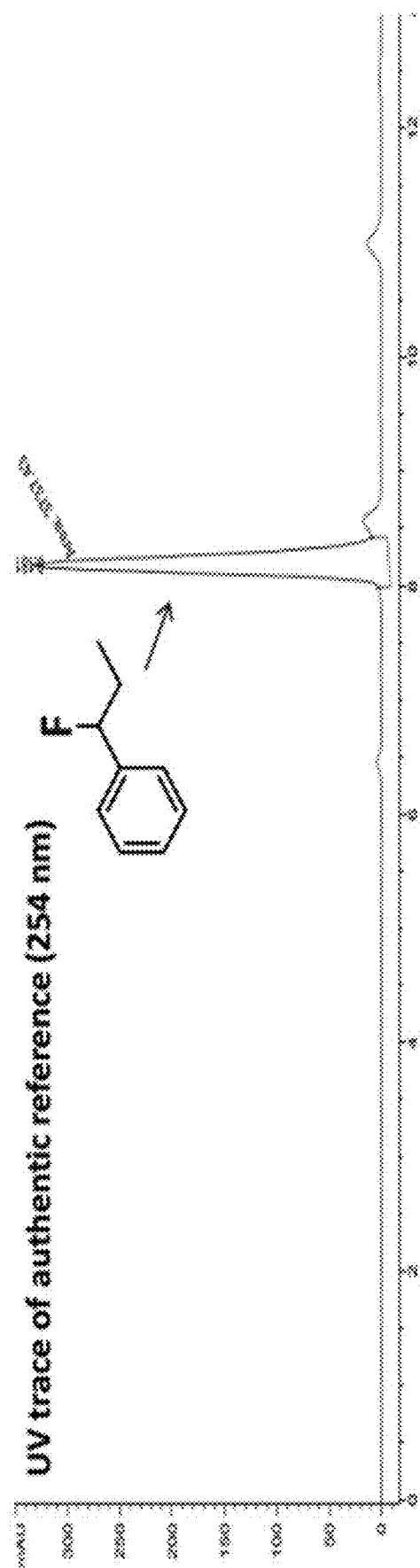
Figure 21B:
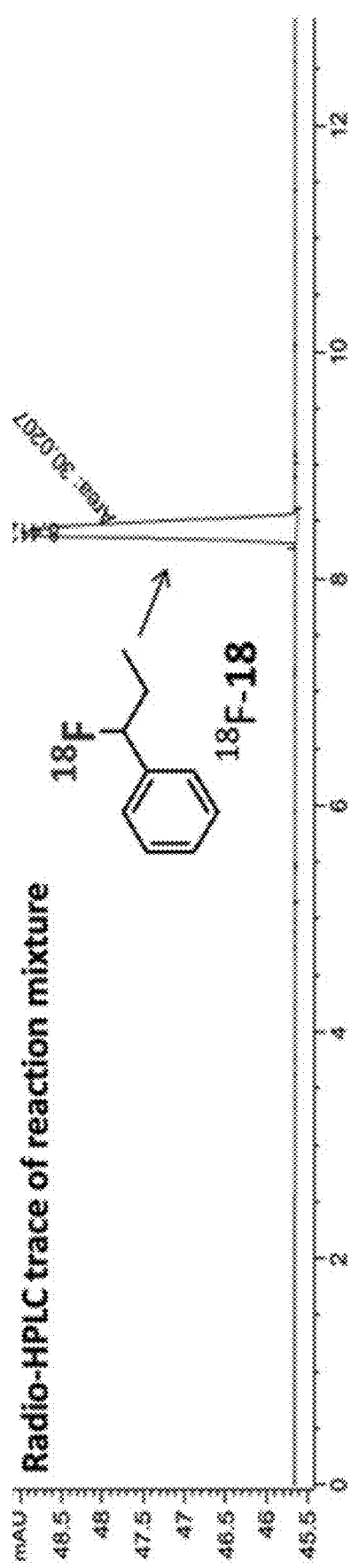
Figure 21C:
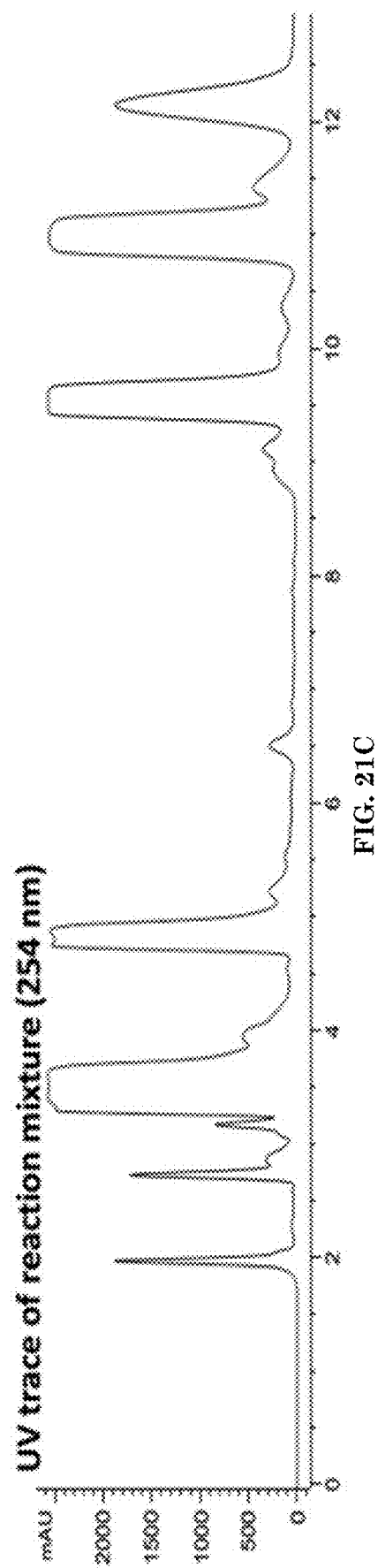

Example 7.3.4 Radio-HPLC Characterization of $^{18}$F-Labeled Products $^{18}$F-labeled products were characterized by comparing the radio-HPLC trace of the crude reaction mixture to the HPLC UV trace of the authentic reference sample. The time difference due to the delay volume between the UV detector and the radioactivity detector was about 0.25 min. HPLC method: mobile phases: ACN (0.1% TFA, A) and H$_2$O (0.1% TFA, B); gradient: 65% A and 35% B, isocratic; column: Agilent Eclipse XDB-C18, 5 m, 4.6×250 mm. FIGS. 15A-15C illustrate the UV trace of the authentic reference of compound F-17, the radio-HPLC trace of the reaction mixture to produce compound $^{18}$F-17, and the UV trace for the reaction mixture. FIGS. 16A-16C, 17A-17C, 18A-18C, 19A-19C, 20A-20C and FIGS. 21A-21C illustrate the same traces as FIGS. 15A-15C but for compounds 19, 8, 14, 15, 5, and 18, respectively.

Example 7.3.5—Specific Activity Measurement

Figure 22:
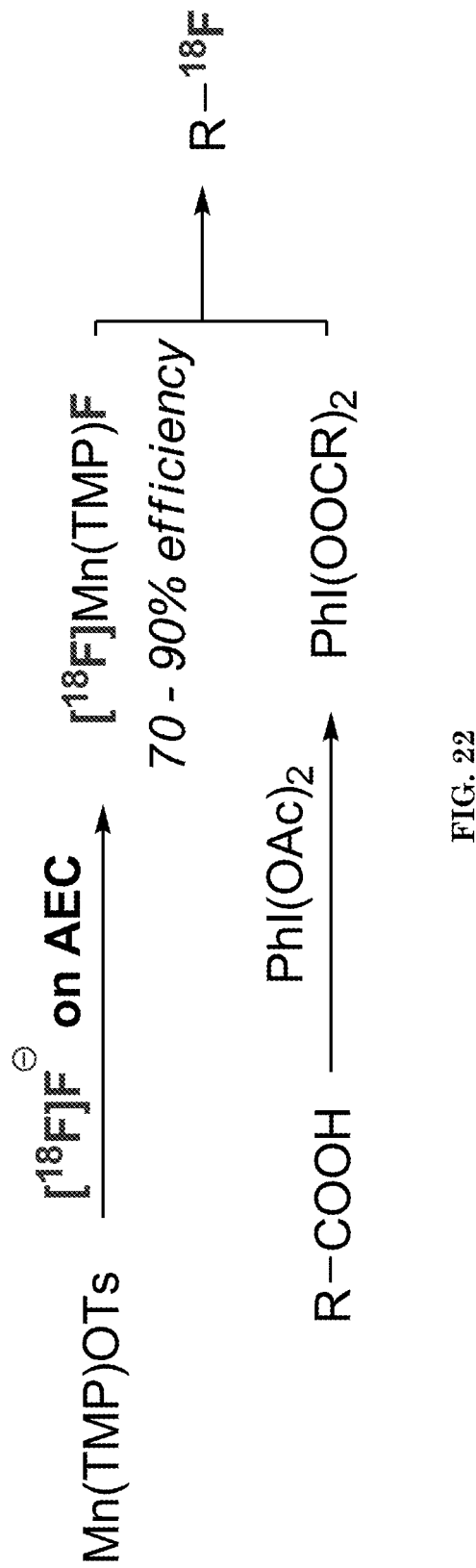
FIG. 22 illustrates a general schematic representation of the azeotropic drying-free method of labeling.

FIG. 22 illustrates a general schematic representation of the azeotropic drying-free method of labeling. The iodine (III) dicarboxylate was synthesized as previously described, [37], namely, a mixture of iodosobenzene diacetate (1 g, 3.1 mmol) and corresponding carboxylic acid (6.2 mmol) was dissolved in chlorobenzene (12 mL). The flask was then placed in a water bath (50-55° C.) and the solvent was removed slowly with reduced pressure. After complete evaporation of the solvent and the acetic acid, the crude mixture was washed with hexanes and used without further purifications. A portion of aqueous [$^{18}$F]fluoride solution (40-50 μL, 4-5 mCi) obtained from the cyclotron was loaded on to a Chromafix PS-HCO$_3$ IEX cartridge, which had been previously washed with 5.0 mg/mL K$_2$CO$_3$ in Milli-Q water followed by 10 mL of Milli-Q water. Then, the cartridge loaded with [$^{18}$F]fluoride was washed with 15 mL Milli-Q water followed by 5 mL of anhydrous acetonitrile. [$^{18}$F] fluoride was slowly released using 0.8 mL methanol solution of Mn(TMP)OTs. Methanol was then removed by a stream of N$_2$ and the resulting solid was redissolved by 0.6 mL dichloromethane. The obtained dichloromethane solution of [$^{18}$F]Mn(TMP)F was added to a 4 mL vial containing 0.1 mmol iodine(III) dicarboxylate and a stir bar (2×5 mm). The vial was capped and stirred at 50° C. for 10 min. After 10 minutes, the radio-labeled compound was isolated by semi-prep HPLC. (Phenomenex Gemini-NX 5µ C18 110A, 250× 10.0 mm, gradient: 0-40.0 min, 65:35 H$_2$O:MeCN to 25:75 H$_2$O:MeCN, 4.0 mL/min; 40.0 min-60.0 min, 25:75 H$_2$O:MeCN, 4.0 mL/min). The absorbance of the $^{18}$F-19 at 254 nm was 224.1, corresponding to 0.269 nmol. The radioactivity of the labeled product was 480 µCi (@EOB). Therefore, the specific activity (SA) was 1.78 Ci/µmol (@EOB).

TABLE 2

Data for standard curve of UV absorbance vs. amount of compound 19

| nmol 19 | UV Absorbance |
|---|---|
| 1.44 | 1333.51 |
| 2.88 | 2544.14 |
| 5.76 | 5070 |
| 11.52 | 9716 |

Figure 23:
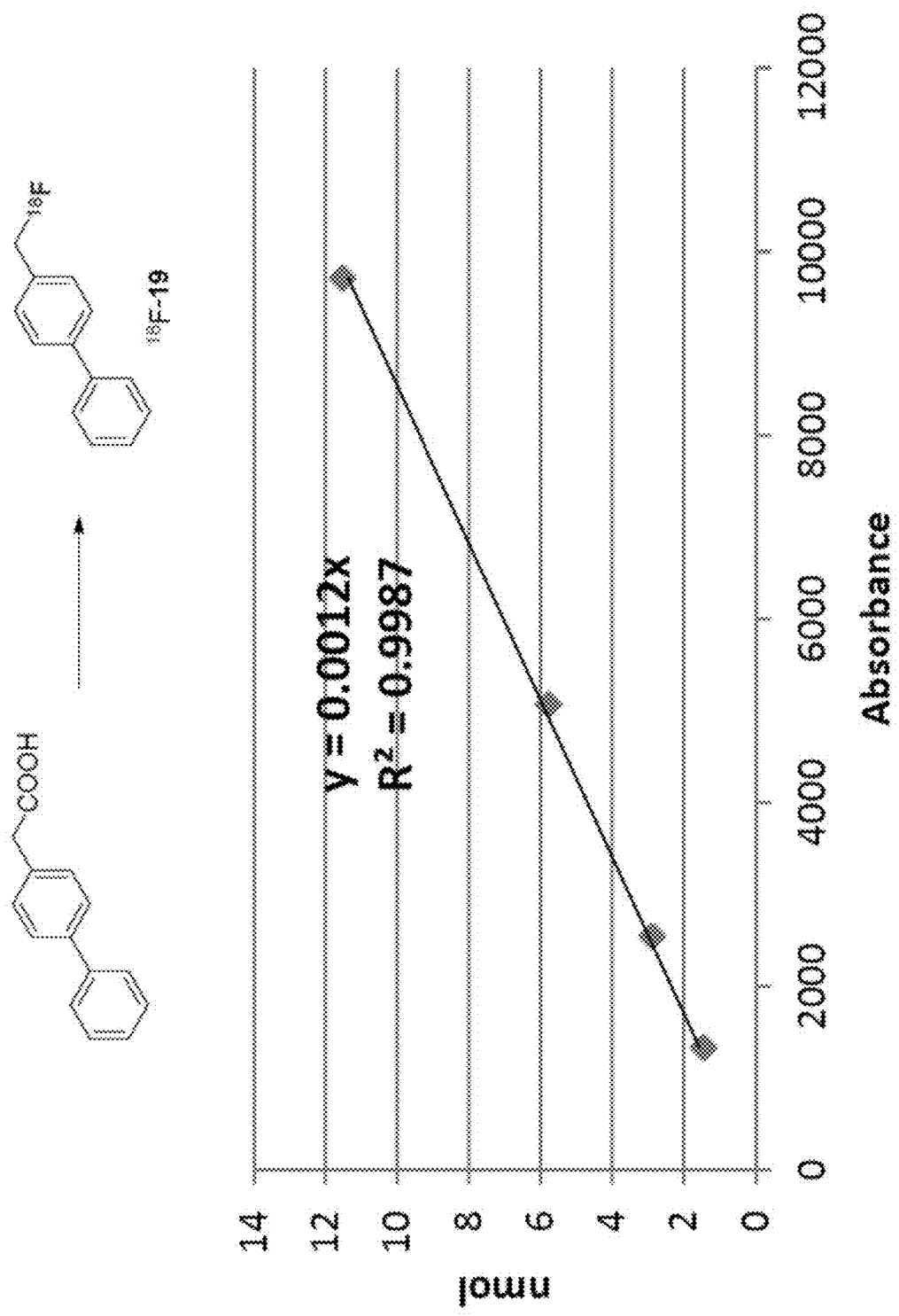
FIG. 23 illustrates a standard curve of UV absorbance vs. amount of compound ¹⁸F-19.

FIG. 23 illustrates standard curve of UV absorbance vs. amount of $^{18}$F-19. The UV standard curve was performed with the $^{19}$F version of compound 19. However, the $^{19}$F- and $^{18}$F-versions of compound 19 have the similar UV-vis spectra.

REFERENCES

[1] a) B. E. Smart, J. Fluorine Chem. 2001, 109, 3-11; b) P. Jeschke, ChemBioChem 2004, 5, 570-589; c) K. Muller, C. Faeh, F. Diederich, Science 2007, 317, 1881-1886; d) S. Purser, P. R. Moore, S. Swallow, V. Gouverneur, Chem. Soc. Rev. 2008, 37, 320-330; e) D. O'Hagan, Chem. Soc. Rev. 2008, 37, 308-319; f) P. W. Miller, N. J. Long, R. Vilar, A. D. Gee, Angew. Chem. Int. Ed. 2008, 47, 8998-9033; g) S. M. Ametamey, M. Honer, P. A. Schubiger, Chem. Rev. 2008, 108, 1501-1516; h) J. M. Hooker, Curr. Opin. Chem. Biol. 2010, 14, 105-111.

[2] a) J. Emsley, Chem. Soc. Rev. 1980, 9, 91-124; b) T. Furuya, A. S. Kamlet, T. Ritter, Nature 2011, 473, 470-477.

[3] a) C. Hollingworth, V. Gouverneur, Chem. Commun. 2012, 48, 2929-2942; b) T. Liang, C. N. Neumann, T. Ritter, Angew. Chem. Int. Ed. 2013; c) J. Wu, Tetrahedron Lett. 2014, 55, 4289-4294; d) M. G. Campbell, T. Ritter, Org. Process Res. Dev. 2014, 18, 474-480; e) A. F. Brooks, J. J. Topczewski, N. Ichiishi, M. S. Sanford, P. J. H. Scott, Chem. Sci. 2014, 5, 4545-4553; f) M. G. Campbell, T. Ritter, Chem. Rec. 2014, 14, 482-491.

[4] a) R. E. Banks, S. N. Mohialdinkhaffaf, G. S. Lal, I. Sharif, R. G. Syvret, J. Chem. Soc., Chem. Commun. 1992, 595-596; b) L. Hintermann, A. Togni, Angew. Chem. Int. Ed. 2000, 39, 4359-+; c) N. Shibata, E. Suzuki, Y. Takeuchi, J. Am. Chem. Soc. 2000, 122, 10728-10729; d) P. P. Tang, T. Furuya, T. Ritter, J. Am. Chem. Soc. 2010, 132, 12150-12154; e) V. Rauniyar, A. D. Lackner, G. L. Hamilton, F. D. Toste, Science 2011, 334, 1681-1684; f) S. Bloom, C. R. Pitts, D. C. Miller, N. Haselton, M. G. Holl, E. Urheim, T. Lectka, Angew. Chem. Int. Ed. 2012, 51, 10580-10583; g) A. R. Mazzotti, M. G. Campbell, P. Tang, J. M. Murphy, T. Ritter, J. Am. Chem. Soc. 2013, 135, 14012-14015; h) S. Bloom, J. L. Knippel, T. Lectka, Chem. Sci. 2014, 5, 1175-1178; i) C. W. Kee, K. F. Chin, M. W. Wong, C. H. Tan, Chem. Commun. 2014, 50, 8211-8214; j) J. B. Xia, C. Zhu, C. Chen, Chem. Commun. 2014, 50, 11701-11704; k) J.-B. Xia, C. Zhu, C. Chen, J. Am. Chem. Soc. 2013, 135, 17494-17500; l) C. R. Pitts, S. Bloom, R. Woltornist, D. J. Auvenshine, L. R. Ryzhkov, M. A. Siegler, T. Lectka, J. Am. Chem. Soc. 2014, 136, 9780-9791.

[5] a) T. Umemoto, K. Tomita, Tetrahedron Lett. 1986, 27, 3271-3274; b) K. L. Hull, W. Q. Anani, M. S. Sanford, J. Am. Chem. Soc. 2006, 128, 7134-7135; c) X. Wang, T.-S. Mei, J.-Q. Yu, J. Am. Chem. Soc. 2009, 131, 7520-+; d) Y. D. Ye, M. S. Sanford, J. Am. Chem. Soc. 2013, 135, 4648-4651; e) P. S. Fier, J. Luo, J. F. Hartwig, J. Am. Chem. Soc. 2013, 135, 2552-2559.

[6] a) Y. Hamashima, K. Yagi, H. Takano, L. Tamas, M. Sodeoka, J. Am. Chem. Soc. 2002, 124, 14530-14531; b) D. D. Steiner, N. Mase, C. F. Barbas, Angew. Chem. Int. Ed. 2005, 44, 3706-3710; c) T. D. Beeson, D. W. C. MacMillan, J. Am. Chem. Soc. 2005, 127, 8826-8828; d) M. Althaus, C. Becker, A. Togni, A. Mezzetti, Organometallics 2007, 26, 5902-5911; e) O. Lozano, G. Blessley, T. M. del Campo, A. L. Thompson, G. T. Giuffredi, M. Bettati, M. Walker, R. Borman, V. Gouverneur, Angew. Chem. Int. Ed. 2011, 50, 8105-8109; f) M. Rueda-Becerril, C. C. Sazepin, J. C. T. Leung, T. Okbinoglu, P. Kennepohl, J. F. Paquin, G. M. Sammis, J. Am. Chem. Soc. 2012, 134, 4026-4029; g) S. D. Halperin, H. Fan, S. Chang, R. E. Martin, R. Britton, Angew. Chem. Int. Ed. 2014, 53, 4690-4693.

[7] a) D. A. Watson, M. Su, G. Teverovskiy, Y. Zhang, J. Garcia-Fortanet, T. Kinzel, S. L. Buchwald, Science 2009, 325, 1661-1664; b) A. Casitas, M. Canta, M. Sola, M. Costas, X. Ribas, J. Am. Chem. Soc. 2011, 133, 19386-19392; c) E. Lee, A. S. Kamlet, D. C. Powers, C. N. Neumann, G. B. Boursalian, T. Furuya, D. C. Choi, J. M. Hooker, T. Ritter, Science 2011, 334, 639-642; d) E. Lee, J. M. Hooker, T. Ritter, J. Am. Chem. Soc. 2012, 134, 17456-17458; e) P. S. Fier, J. F. Hartwig, J. Am. Chem. Soc. 2012, 134, 10795-10798; f) Y. Ye, S. D. Schimler, P. S. Hanley, M. S. Sanford, J. Am. Chem. Soc. 2013, 135, 16292-16295; g) P. S. Fier, J. F. Hartwig, Science 2013, 342, 956-960; h) T. Truong, K. Klimovica, O. Daugulis, J. Am. Chem. Soc. 2013, 135, 9342-9345; i) N. Ichiishi, A. F. Brooks, J. J. Topczewski, M. E. Rodnick, M. S. Sanford, P. J. H. Scott, Org. Lett. 2014, 16, 3224-3227; j) M. Tredwell, S. M. Preshlock, N. J. Taylor, S. Gruber, M. Huiban, J. Passchier, J. Mercier, C. Genicot, V. Gouverneur, Angew. Chem. Int. Ed. 2014, 53, 7751-7755.

[8] a) D. S. Laitar, P. Muller, T. G. Gray, J. P. Sadighi, Organometallics 2005, 24, 4503-4505; b) B. C. Gorske, C. T. Mbofana, S. J. Miller, Org. Lett. 2009, 11, 4318-4321.

[9] a) A. Hazari, V. Gouverneur, J. M. Brown, Angew. Chem. Int. Ed. 2009, 48, 1296-1299; b) M. H. Katcher, A. G. Doyle, J. Am. Chem. Soc. 2010, 132, 17402-17404; c) C. Hollingworth, A. Hazari, M. N. Hopkinson, M. Tredwell, E. Benedetto, M. Huiban, A. D. Gee, J. M. Brown, V. Gouverneur, Angew. Chem. Int. Ed. 2011, 50, 2613-2617; d) J. J. Topczewski, T. J. Tewson, H. M. Nguyen, J. Am. Chem. Soc. 2011, 133, 19318-19321; e) A. M. Lauer, J. Wu, Org. Lett. 2012, 14, 5138-5141; f) E. Benedetto, M.

Tredwell, C. Hollingworth, T. Khotavivattana, J. M. Brown, V. Gouverneur, *Chem. Sci.* 2013, 4, 89-96; g) Z. Zhang, F. Wang, X. Mu, P. Chen, G. Liu, *Angew. Chem. Int. Ed.* 2013, 52, 7549-7553; h) M.-G. Braun, A. G. Doyle, *J. Am. Chem. Soc.* 2013, 135, 12990-12993; i) M.-G. Braun, A. G. Doyle, *J. Am. Chem. Soc.* 2013, 135, 12990-12993.

[10] a) S. Bruns, G. Haufe, *J. Fluorine Chem.* 2000, 104, 247-254; b) Y. Hamashima, M. Sodeoka, *Synlett* 2006, 1467-1478; c) C. Bobbio, V. Gouverneur, *Org. Biomol. Chem.* 2006, 4, 2065-2075; d) M. Althaus, A. Togni, A. Mezzetti, *J. Fluorine Chem.* 2009, 130, 702-707; e) J. A. Kalow, A. G. Doyle, *J. Am. Chem. Soc.* 2010, 132, 3268-+; f) T. J. A. Graham, R. F. Lambert, K. Ploessl, H. F. Kung, A. G. Doyle, *J. Am. Chem. Soc.* 2014, 136, 5291-5294.

[11] a) J. G. Macneil, D. J. Burton, *J. Fluorine Chem.* 1991, 55, 225-227; b) M. Huiban, M. Tredwell, S. Mizuta, Z. Wan, X. Zhang, T. L. Collier, V. Gouverneur, J. Passchier, *Nat. Chem.* 2013, 5, 941-944; c) T. Ruhl, W. Rafique, V. T. Lien, P. J. Riss, *Chem. Commun.* 2014, 50, 6056-6059; d) D. van der Born, C. Sewing, J. D. M. Herscheid, A. D. Windhorst, R. V. A. Orru, D. J. Vugts, *Angew. Chem. Int. Ed.* 2014, 53, 11046-11050.

[12] K. B. McMurtrey, J. M. Racowski, M. S. Sanford, *Org. Lett.* 2012, 14, 4094-4097.

[13] H. Dang, M. Mailig, G. Lalic, *Angew. Chem. Int. Ed.* 2014, 53, 6473-6476.

[14] W. Liu, X. Y. Huang, M. J. Cheng, R. J. Nielsen, W. A. Goddard, J. T. Groves, *Science* 2012, 337, 1322-1325.

[15] a) W. Liu, J. T. Groves, *Angew. Chem. Int. Ed.* 2013, 52, 6024-6027; b) W. Liu, X. Huang, J. T. Groves, *Nat. Protoc.* 2013, 8, 2348-2354.

[16] X. Y. Huang, W. Liu, H. Ren, R. Neelamegam, J. M. Hooker, J. T. Groves, *J. Am. Chem. Soc.* 2014, 136, 6842-6845.

[17] a) M. Komuro, T. Higuchi, M. Hirobe, *J. Pharmacobio-Dyn.* 1992, 15, S89-S89; b) S. Tangestaninejad, V. Mirkhani, *J. Chem. Res.* 1998, 820-821.

[18] a) V. Grakauskas, *J. Org. Chem.* 1969, 34, 2446-2450; b) T. B. Patrick, K. K. Johri, D. H. White, *J. Org. Chem.* 1983, 48, 4158-4159.

[19] a) F. Yin, Z. T. Wang, Z. D. Li, C. Z. Li, *J. Am. Chem. Soc.* 2012, 134, 10401-10404; b) M. Rueda-Becerril, O. Mahe, M. Drouin, M. B. Majewski, J. G. West, M. O. Wolf, G. M. Sammis, J. F. Paquin, *J. Am. Chem. Soc.* 2014, 136, 2637-2641; c) J. C. T. Leung, C. Chatalova-Sazepin, J. G. West, M. Rueda-Becerril, J. F. Paquin, G. M. Sammis, *Angew. Chem. Int. Ed.* 2012, 51, 10804-10807; d) Y. Qiao, L. Zhu, B. R. Ambler, R. A. Altman, *Curr. Top. Med. Chem.* 2014, 14, 966-978; e) S. Mizuta, I. S. R. Stenhagen, M. O'Duill, J. Wolstenhulme, A. K. Kirjavainen, S. J. Forsback, M. Tredwell, G. Sandford, P. R. Moore, M. Huiban, S. K. Luthra, J. Passchier, O. Solin, V. Gouverneur, *Org. Lett.* 2013, 15, 2648-2651.

[20] R. Franz, *J. Fluorine Chem.* 1980, 15, 423-434.

[21] a) J. T. Groves, W. J. Kruper, R. C. Haushalter, *J. Am. Chem. Soc.* 1980, 102, 6375-6377; b) J. T. Groves, M. K. Stern, *J. Am. Chem. Soc.* 1987, 109, 3812-3814; c) J. T. Groves, *J. Porphyrins Phthalocyanines* 2000, 4, 350-352; d) C. M. Che, V. K. Y. Lo, C. Y. Zhou, J. S. Huang, *Chem. Soc. Rev.* 2011, 40, 1950-1975.

[22] M. Komuro, Y. Nagatsu, T. Higuchi, M. Hirobe, *Tetrahedron Lett.* 1992, 33, 4949-4952.

[23] J. Shi, X. Y. Huang, J. P. Wang, R. Li, *J. Phys. Chem. A* 2010, 114, 6263-6272.

[24] L. Li, M. N. Hopkinson, R. L. Yona, R. Bejot, A. D. Gee, V. Gouverneur, *Chem. Sci.* 2011, 2, 123-131.

[25] L. Mathew, J. Warkentin, *Can. J. Chem.* 1988, 66, 11-16.

[26] a) J. S. Lindsey, R. W. Wagner, *J. Org. Chem.* 1989, 54, 828-836; b) A. D. Adler, Shergali. W, F. R. Longo, *J. Am. Chem. Soc.* 1964, 86, 3145-&.

[27] a) A. D. Adler, F. R. Longo, F. Kampas, J. Kim, *Journal of Inorganic & Nuclear Chemistry* 1970, 32, 2443-&; b) J. T. Groves, W. J. Kruper, R. C. Haushalter, *J. Am. Chem. Soc.* 1980, 102, 6375-6377.

[28] A. Essersi, R. Touati, H. B. Ben, *Lett. Org. Chem.* 2010, 7, 69-72.

[29] S. B. Daniels, E. Cooney, M. J. Sofia, P. K. Chakravarty, J. A. Katzenellenbogen, *J. Biol. Chem.* 1983, 258, 5046-5053.

[30] a) J. C. Roberts, K. Selby, *J. Chem. Soc.* 1951, 2335-2339; b) R. H. Prager, K. Schafer, *Aust. J. Chem.* 1997, 50, 813-823.

[31] P. L. Liu, L. Huang, M. M. Faul, *Tetrahedron Lett.* 2007, 48, 7380-7382.

[32] E. Hermann Rempfler, B. Rolf Schurter, B. Werner Fory, Vol. 06206518, JP 51-139627 (December, 1976); JP 51-142536 (December, 1976); JP 51-142537 (December, 1976); U.S. Pat. No. 4,046,553 (September, 1977) Takahashi et al. 546/291 X; U.S. Pat. No. 4,133,675 (January, 1979) Schurter et al. 546/283 X; U.S. Pat. No. 4,233,054 (November, 1980) Szczepanski et al. 71/70; U.S. Pat. No. 4,233,055 (November, 1980) Martin 71/76; U.S. Pat. No. 4,233,056 (November, 1980) Maier 71/86; U.S. Pat. No. 4,233,306 (November, 1980) Boger et al. 424/263; U.S. Pat. No. 4,233,308 (November, 1980) Kunz et al. 424/279; U.S. Pat. No. 4,244,962 (January, 1981) Hubele et al. 424/267; U.S. Pat. No. 4,253,866 (March, 1981) Schurter et al. 71/94, US, 1982.

[33] C. J. Roxburgh, C. R. Ganellin, A. J. Thorpe, *Synlett* 2007, 1211-1214.

[34] N. Hirokichi Harada, Vol. 05545342, U.S. Pat. No. 3,812,116 (May, 1974) Takano et al. 260/243 C, US, 1977.

[35] Y. Xiong, M. Zhao, C. Wang, H. W. Chang, S. Q. Peng, *J. Med. Chem.* 2007, 50, 3340-3353.

[36] a) Z. S. Yang, J. X. Wang, Y. Zhou, H. P. Zuo, Y. Li, *Bioorg. Med. Chem.* 2006, 14, 8043-8049; b) Z. S. Yang, W. L. Zhou, Y. Sui, J. X. Wang, J. M. Wu, Y. Zhou, Y. Zhang, P. L. He, J. Y. Han, W. Tang, W. Li, J. P. Zuo, *J. Med. Chem.* 2005, 48, 4608-4617.

[37] a) D. N. Zalatan, J. Du Bois, *J. Am. Chem. Soc.* 2009, 131, 7558-+; b) J. E. Leffler, D. C. Ward, Burdurog. A, *J. Am. Chem. Soc.* 1972, 94, 5339-&; c) P. J. Stang, M. Boehshar, H. Wingert, T. Kitamura, *J. Am. Chem. Soc.* 1988, 110, 3272-3278.

[38] M. J. Frisch, G. W. Trucks, H. B. Schlegel, G. E. Scuseria, M. A. Robb, J. R. Cheeseman, J. A. Montgomery, T. Vreven, K. N. Kudin, J. C. Burant, J. M. Millam, S. S. Iyengar, J. Tomasi, V. Barone, B. Mennucci, M. Cossi, G. Scalmani, N. Rega, G. A. Petersson, H. Nakatsuji, M. Hada, M. Ehara, K. Toyota, R. Fukuda, J. Hasegawa, M. Ishida, T. Nakajima, Y. Honda, O. Kitao, H. Nakai, M. Klene, X. Li, J. E. Knox, H. P. Hratchian, J. B. Cross, V. Bakken, C. Adamo, J. Jaramillo, R. Gomperts, R. E. Stratmann, O. Yazyev, A. J. Austin, R. Cammi, C. Pomelli, J. W. Ochterski, P. Y. Ayala, K. Morokuma, G. A. Voth, P. Salvador, J. J. Dannenberg, V. G. Zakrzewski, S. Dapprich, A. D. Daniels, M. C. Strain, O. Farkas, D. K. Malick, A. D. Rabuck, K. Raghavachari, J. B. Foresman, J. V. Ortiz, Q. Cui, A. G. Baboul, S.

Clifford, J. Cioslowski, B. B. Stefanov, G. Liu, A. Liashenko, P. Piskorz, I. Komaromi, R. L. Martin, D. J. Fox, T. Keith, A. Laham, C. Y. Peng, A. Nanayakkara, M. Challacombe, P. M. W. Gill, B. Johnson, W. Chen, M. W. Wong, C. Gonzalez, J. A. Pople, Gaussian 09 (Revision C.01), Gaussian Inc., Wallingford, C T, 2010.

[39] F. Neese, *J. Am. Chem. Soc.* 2006, 128, 10213-10222.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

Any single embodiment herein may be supplemented with one or more element from any one or more other embodiment herein.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of targeted fluorination of a compound containing a carboxyl group, the method comprising combining the compound containing a carboxyl group, a nucleophilic fluoride source, a solvent and an iodine (III) oxidant to form a mono-fluoro-aryl iodine-(III) carboxylate and then combining the mono-fluoro-aryl iodine-(III) carboxylate with a manganese catalyst.

2. The method of claim 1, wherein the manganese catalyst is a manganese porphyrin or a manganese salen.

3. The method of claim 1 further comprising maintaining the mono-fluoro-aryl iodine-(III) carboxylate at a temperature from 25° C. to 80° C.

4. The method of claim 1, wherein the nucleophilic fluoride source is trialkyl amine trihydrofluoride.

5. The method of claim 4, wherein the trialkyl amine trihydrofluoride is triethylamine trihydrofluoride.

6. The method of claim 1, wherein the step of combining is performed under an inert atmosphere.

7. The method of claim 1, wherein the nucleophilic fluoride source is [$^{18}$F]-fluoride.

8. The method of claim 1, wherein prior to the step of mixing, the method comprises obtaining an aqueous [$^{18}$F] fluoride solution from a cyclotron, loading the aqueous [$^{18}$F] fluoride solution onto an ion exchange cartridge and releasing the [$^{18}$F] fluoride from the ion exchange cartridge with an alkaline solution.

* * * * *